US012646589B2

(12) United States Patent
Kyriazopoulou Panagiotopou et al.

(10) Patent No.: US 12,646,589 B2
(45) Date of Patent: Jun. 2, 2026

(54) ARTIFICIAL INTELLIGENCE-BASED EPIGENETICS

(71) Applicant: Illumina, Inc., San Diego, CA (US)

(72) Inventors: Sofia Kyriazopoulou Panagiotopou, Redwood City, CA (US); Kai-How Farh, San Mateo, CA (US)

(73) Assignee: Illumina, Inc., San Diego, CA (US)

( * ) Notice: Subject to any disclaimer, the term of this patent is extended or adjusted under 35 U.S.C. 154(b) by 1116 days.

(21) Appl. No.: 17/642,942

(22) PCT Filed: Sep. 18, 2020

(86) PCT No.: PCT/US2020/051639
§ 371 (c)(1),
(2) Date: Mar. 14, 2022

(87) PCT Pub. No.: WO2021/055857
PCT Pub. Date: Mar. 25, 2021

(65) Prior Publication Data
US 2022/0406411 A1     Dec. 22, 2022

Related U.S. Application Data

(60) Provisional application No. 62/903,700, filed on Sep. 20, 2019.

(51) Int. Cl.
*G16B 40/20*          (2019.01)
*G06F 18/2137*     (2023.01)
(Continued)

(52) U.S. Cl.
CPC ......... *G16B 40/20* (2019.02); *G06F 18/2137* (2023.01); *G06N 3/063* (2013.01); *G16B 30/00* (2019.02)

(58) Field of Classification Search
CPC ........ G16B 40/20; G16B 30/00; G16B 20/20; G16B 40/10; G16B 40/00; G06F 18/2137; G06N 3/063
See application file for complete search history.

(56) References Cited

U.S. PATENT DOCUMENTS

| | | | |
|---|---|---|---|
| 6,060,033 | A | 5/2000 | Cheng |
| 6,269,934 | B2 | 8/2001 | Baker |

(Continued)

FOREIGN PATENT DOCUMENTS

| | | |
|---|---|---|
| CA | 2894317 A1 | 12/2016 |
| CN | 103679185 A | 3/2014 |

(Continued)

OTHER PUBLICATIONS

Gandolfi, F., Tramontano, A. A computational approach for the functional classification of the epigenome. Epigenetics & Chromatin 10, 26 (2017). https://doi.org/10.1186/s13072-017-0131-7 (Year: 2017).*

(Continued)

*Primary Examiner* — Sun M Li
(74) *Attorney, Agent, or Firm* — Fletcher Yoder, P.C.

(57)          ABSTRACT

An artificial intelligence-based system comprises an input preparation module that accesses a sequence database and generates an input base sequence. The input base sequence comprises a target base sequence with target bases, wherein the target base sequence is flanked by a right base sequence with downstream context bases, and a left base sequence with upstream context bases. A sequence-to-sequence model processes the input base sequence and generates an alternative representation of the input base sequence. An output module processes the alternative representation of the input base sequence and produces at least one per-base output for each of the target bases in the target base sequence. The (Continued)

Input Base Sequence 2602     Sequence-to-Sequence Epigenetic Model 2700 output 2704 alternative representation 2702 per-base output specifies, for a corresponding target base, signal levels of a plurality of epigenetic tracks.

24 Claims, 36 Drawing Sheets

(51) Int. Cl.
| | | |
|---|---|---|
| *G06N 3/063* | (2023.01) | |
| *G16B 30/00* | (2019.01) | |

(56) References Cited

U.S. PATENT DOCUMENTS

| | | | |
|---|---|---|---|
| 8,762,072 | B2 | 6/2014 | Janevski et al. |
| 10,068,557 | B1 | 9/2018 | Engel et al. |
| 10,185,803 | B2 | 1/2019 | Frey et al. |
| 10,216,895 | B2 | 2/2019 | Liu |
| 10,410,118 | B2 | 9/2019 | Xiong et al. |
| 10,423,861 | B2 | 9/2019 | Gao et al. |
| 10,540,591 | B2 | 1/2020 | Gao et al. |
| 10,558,915 | B2 | 2/2020 | Gao et al. |
| 10,770,169 | B2 | 9/2020 | Vaske et al. |
| 10,793,895 | B2* | 10/2020 | Locke ................... C12Q 1/6874 |
| 11,288,576 | B2 | 3/2022 | Dutta et al. |
| 11,315,016 | B2 | 4/2022 | Sundaram et al. |
| 11,443,832 | B2* | 9/2022 | Israeli ................... G06N 3/0418 |
| 11,861,491 | B2 | 1/2024 | Kyriazopoulou Panagiotopoulou et al. |
| 2002/0055100 | A1 | 5/2002 | Kawashima et al. |
| 2003/0187587 | A1 | 10/2003 | Swindells et al. |
| 2006/0228728 | A1 | 10/2006 | Cox et al. |
| 2007/0166754 | A1 | 7/2007 | Mohanlal |
| 2011/0004110 | A1 | 1/2011 | Shusterman |
| 2011/0294681 | A1 | 12/2011 | Hinds et al. |
| 2013/0110407 | A1 | 5/2013 | Baccash et al. |
| 2013/0203053 | A1 | 8/2013 | Princen et al. |
| 2013/0296175 | A1 | 11/2013 | Rafnar et al. |
| 2013/0332081 | A1 | 12/2013 | Reese et al. |
| 2014/0129152 | A1 | 5/2014 | Beer et al. |
| 2014/0304204 | A1 | 10/2014 | Cameron et al. |
| 2015/0324519 | A1 | 11/2015 | Liu |
| 2015/0337388 | A1 | 11/2015 | Garner et al. |
| 2016/0004814 | A1 | 1/2016 | Stamatoyannopoulos |
| 2016/0068915 | A1 | 3/2016 | Kennedy et al. |
| 2016/0085910 | A1 | 3/2016 | Bruand et al. |
| 2016/0132637 | A1 | 5/2016 | Varadan et al. |
| 2016/0140289 | A1 | 5/2016 | Gibiansky et al. |
| 2016/0145516 | A1 | 5/2016 | Scott |
| 2016/0196479 | A1 | 7/2016 | Chertok |
| 2016/0201564 | A1 | 7/2016 | Oba |
| 2016/0201565 | A1 | 7/2016 | Grose et al. |
| 2016/0275239 | A1* | 9/2016 | Devogelaere ........ C12Q 1/6874 |
| 2016/0357903 | A1* | 12/2016 | Shendure ............... G16B 30/00 |
| 2016/0364522 | A1 | 12/2016 | Frey et al. |
| 2016/0364545 | A1 | 12/2016 | Das et al. |
| 2016/0371431 | A1 | 12/2016 | Haque et al. |
| 2017/0151679 | A1 | 6/2017 | Wong et al. |
| 2017/0169313 | A1 | 6/2017 | Choi |
| 2017/0199961 | A1 | 7/2017 | Yelensky et al. |
| 2017/0286594 | A1 | 10/2017 | Reid et al. |
| 2017/0344698 | A1* | 11/2017 | Griffin ................... G16B 20/00 |
| 2018/0107927 | A1 | 4/2018 | Frey |
| 2018/0197067 | A1 | 7/2018 | Mody et al. |
| 2018/0322327 | A1 | 11/2018 | Smith et al. |
| 2018/0330824 | A1 | 11/2018 | Athey et al. |
| 2018/0350451 | A1 | 12/2018 | Ohnemus et al. |
| 2019/0060428 | A1 | 2/2019 | Fritsch |
| 2019/0114511 | A1 | 4/2019 | Gao et al. |
| 2019/0114544 | A1 | 4/2019 | Sundaram et al. |
| 2019/0180844 | A1* | 6/2019 | Jung ...................... G06N 3/045 |
| 2019/0206521 | A1 | 7/2019 | Walpole et al. |
| 2019/0219599 | A1 | 7/2019 | O'Bryant et al. |
| 2019/0220704 | A1 | 7/2019 | Schulz-Trieglaff et al. |
| 2019/0232592 | A1 | 8/2019 | Tran et al. |
| 2019/0236447 | A1 | 8/2019 | Cohen et al. |
| 2019/0259499 | A1 | 8/2019 | Hong et al. |
| 2019/0266491 | A1 | 8/2019 | Gao et al. |
| 2019/0266493 | A1 | 8/2019 | Gao et al. |
| 2020/0005899 | A1* | 1/2020 | Nicula ................... G16B 40/20 |
| 2020/0065675 | A1 | 2/2020 | Sundaram et al. |
| 2020/0098465 | A1 | 3/2020 | Jiang et al. |
| 2020/0227137 | A1 | 7/2020 | Sanborn |
| 2020/0243167 | A1 | 7/2020 | Will et al. |
| 2020/0279157 | A1 | 9/2020 | Gao et al. |
| 2020/0342955 | A1* | 10/2020 | Guo ...................... G16B 20/20 |
| 2020/0370124 | A1 | 11/2020 | Hall et al. |
| 2020/0411199 | A1 | 12/2020 | Shrager et al. |
| 2021/0020293 | A1 | 1/2021 | Richards |
| 2021/0027855 | A1* | 1/2021 | Zhou ...................... G16B 20/00 |
| 2022/0130489 | A1* | 4/2022 | Jung ...................... G16B 20/20 |
| 2023/0004749 | A1* | 1/2023 | Jaganathan ............ G16B 40/20 |
| 2024/0011074 | A1* | 1/2024 | Locke .................. C12Q 1/6806 |

FOREIGN PATENT DOCUMENTS

| | | | | |
|---|---|---|---|---|
| CN | 105378104 | A | 3/2016 | |
| CN | 106575321 | A | 4/2017 | |
| CN | 110010201 | A | 7/2019 | |
| JP | 2002505741 | A | 2/2002 | |
| JP | 2003527698 | A | 9/2003 | |
| JP | 2007052774 | A | 3/2007 | |
| JP | 2008216557 | A | 9/2008 | |
| JP | 2012032163 | A | 2/2012 | |
| JP | 2012504761 | A | 2/2012 | |
| JP | 2015501974 | A | 1/2015 | |
| JP | 2017111830 | A | 6/2017 | |
| JP | 2017520821 | A | 7/2017 | |
| JP | 2017168866 | A | 9/2017 | |
| JP | 2018504784 | A | 2/2018 | |
| JP | 2018527647 | A | 9/2018 | |
| RU | 2470998 | C2 | 12/2012 | |
| WO | 1997005552 | A1 | 2/1997 | |
| WO | 199854669 | A1 | 12/1998 | |
| WO | 2010/038173 | A1 | 4/2010 | |
| WO | 2011/139345 | A2 | 11/2011 | |
| WO | 2013/070634 | A1 | 5/2013 | |
| WO | 2015/173222 | A1 | 11/2015 | |
| WO | 2016/061396 | A1 | 4/2016 | |
| WO | 2016/145516 | A1 | 9/2016 | |
| WO | 2016/201049 | A2 | 12/2016 | |
| WO | 2016/201564 | A1 | 12/2016 | |
| WO | 2016/209999 | A1 | 12/2016 | |
| WO | 2017/172958 | A1 | 10/2017 | |
| WO | 2019/079180 | A1 | 4/2019 | |
| WO | 2019/079182 | A1 | 4/2019 | |
| WO | 2019079166 | A1 | 4/2019 | |
| WO | 2019079198 | A1 | 4/2019 | |
| WO | WO-2019084559 | A1 * | 5/2019 | ............ G16B 40/20 |
| WO | 2019/136284 | A1 | 7/2019 | |
| WO | 2019/140402 | A1 | 7/2019 | |
| WO | WO-2019191123 | A1 * | 10/2019 | ............ G16B 25/10 |

OTHER PUBLICATIONS

Martin J. Aryee, Andrew E. Jaffe, Hector Corrada-Bravo, Christine Ladd-Acosta, Andrew P. Feinberg, Kasper D. Hansen, Rafael A. Irizarry, Minfi: a flexible and comprehensive Bioconductor package for the analysis of Infinium DNA methylation microarrays, Bio, vol. 30, Issue 10, May 2014, p. 1363-1369 (Year: 2014).*

Jaganathan K, Kyriazopoulou Panagiotopoulou S, McRae JF, Darbandi SF, Knowles D, Li Yi, Kosmicki JA, Arbelaez J, Cui W, Schwartz GB, Chow ED, Kanterakis E, Gao H, Kia A, Batzoglou S, Sanders SJ, Farh KK. Predicting Splicing from Primary Sequence with Deep Learning. Cell. Jan. 24, 2019;176(3):535-548.e24. (Year: 2019).*

D. Ravi et al., "Deep Learning for Health Informatics," in IEEE Journal of Biomedical and Health Informatics, vol. 21, No. 1, pp. 4-21, Jan. 2017, doi: 10.1109/JBHI.2016.2636665. (Year: 2017).*

F. Celesti, A. Celesti, J. Wan and M. Villari, "Why Deep Learning Is Changing the Way to Approach NGS Data Processing: A Review," in IEEE Reviews in Biomedical Engineering, vol. 11, pp. 68-76, 2018, doi: 10.1109/RBME.2018.2825987. (Year: 2018).*

(56) References Cited

OTHER PUBLICATIONS

Bhande A., "What is underfitting and overfitting in machine learning and how to deal with it", Medium, Mar. 11, 2018, 10 pages.

Bi Y., et al., "Tree-Based Position Weight Matrix Approach to Model Transcription Factor Binding Site Profiles", PLoS One 6(9), Sep. 2, 2011, 14 pages.

Caron, et al., "NCBoost classifies pathogenic non-coding variants in Mendelian diseases through supervised learning on purifying selection signals in humans", Genome Biology, Feb. 11, 2019, 22 pages.

Chang C-Y, et al., "Oversampling to Overcome Overfitting: Exploring the Relationship between Data Set Composition, Molecular Descriptors, and Predictive Modeling Methods", J. Chem. Inf. Model, Mar. 2, 2013, 958-971.

Chen H., "A Computational Approach for Modeling the Allele Frequency Spectrum of Populations with Arbitrarily Varying Size", Genomics Proteomics and Bioinformatics, vol. 17, No. 6, Dec. 1, 2019, 635-644.

Chen, et al., "DeepLab: Semantic Image Segmentation with Deep Convolutional Nets, Atreus Convolution, and Fully Connected CRFs", IEEE Transactions on Pattern Analysis and Machine Intelligence, vol. 40, No. 4, Apr. 2018, pp. 834-848.

Despois J., "Memorizing is not learning!—6 tricks to prevent overfitting in machine learnin", Mar. 20, 2018, 17 pages.

Douville, et al., "Assessing the Pathogenicity of Insertion and Deletion Variants with the Variant Effect Scoring Tool (VEST-Indel)", Human Mutation, Oct. 7, 2015, 28-35.

Eigen, "Eigen is a spectral approach to the functional annotation of genetic variants in coding and noncoding regions", Columbia University, Dec. 19, 2018.

Flygare, et al., "The VAAST Variant Prioritizer (VVP): ultrafast, easy to use whole genome variant prioritization tool", BMC Bioinformatics, Feb. 20, 2018, 13 pages.

Fu, et al., "Noncoding variants functional prioritization methods based on predicted regulatory factor binding sites.", Current Genomics, 2017, vol. 18, No. 4, Aug. 1, 2017, pp. 322-331.

Gao T., "Identifying translation initiation sites in prokaryotes using support vector machine", Journal of Theoretical Biology, Oct. 17, 2010, 644-649.

Geeks for Geeks, "Underfitting and Overfitting in Machine Learning", https://www.geeksforgeeks.org/underfitting-and-overfitting-in-machine-learning/, Aug. 26, 2019, 2 pages.

Karczewski K., et al., "The Genome Aggregation Database (gnomAD)", MacArthur Lab, Mar. 4, 2019, 19 Pages.

Karczewski K., et al., "The mutational constraint spectrum quantified from variation in 141,456 humans", Nature, MacMillan Journals Ltd., etc., London, vol. 581, No. 7809;, 2020, 1-24.

Karydis, et al., "Learning Hierarchical Motif Embeddings for Protein Engineering", Massachusetts Institute of Technology, 2017, 2017, 79 pages.

Korhonen J., et al., "Fast motif matching revisited: high-order PWMs, SNPs and indels", Bioinformatics, Dec. 5, 2016, 514-521.

Krizhevsky A., et al., "ImageNet Classification with Deep Convolutional Neural Networks", Advances in neural information processing systems, 2012, 1097-1105.

Lanchantin, et al., "Prototype Matching Networks for Large-Scale Multi-label Genomic Sequence Classification", arXiv:1710.11238., 2017, Oct. 30, 2017.

Li G., et al., "Classification of Genetic Mutations for Cancer Treatment with Machine Learning Approaches", International Journal of Design, Analysis and Tools for Intergrated Circuits and Systems, Oct. 1, 2018, 63-67.

Lin, et al., "Computational identification and characterization of primate-specific microRNAs in human genome", Computational Biology and Chemistry, Aug. 1, 2010, 232-241.

Martin-Navarro A., et al., "Machine learning classifier for identification of damaging missense mutations exclusive to human mitochondrial DNA-encoded polypeptides", BMC Bioinformatics, Mar. 7, 2017, 12 pages.

Prakash, V.J., et al., "A Survey on Semi-Supervised Learning Techniques", International Journal of Computer Trends and Technology (IJCTT), Feb. 1, 2014, 25-29 pages.

Reed S., et al., "Training Deep Neural Networks on Noisy Labels with Bootstrapping", Cornell University, Apr. 15, 2015, 11 Pages.

Stanescu, et al., "An Empirical Study of Ensemble-Based Semi-Supervised Learning Approaches for Imbalanced Splice Site Datasets", BMC Systems Biology, Sep. 1, 2015, 12 pages.

Stanescu, A., et al., "Ensemble-based semi-supervised learning approaches for imbalanced splice site datasets", 2014 IEEE International Conference on Bioinformatics and Biomedicine, Nov. 2, 2014, 432-437.

Van Der Velde , et al., "GAVIN: Gene-Aware Variant INterpretation for medical sequencing", Genome Biology, Jan. 16, 2017, 10 pages.

Vikram S., et al., "SSCM: A method to analyze and predict the pathogenicity of sequence variants", bioRxiv, Jun. 26, 2015, 30 Pages.

Wang, et al., "MISCORE: Mismatch-Based Matrix Similarity Scores for DNA Motif Detection", In International Conference on Neural Information Processing, 2008, Nov. 25, 2008, pp. 478-485.

Wong S., et al., "Understanding Data Augmentation for Classification: When to Warp?", IEEE Explore, Nov. 30, 2016, 6 pages.

Zhang Y., et al., "Discerning novel splice junctions derived from RNA-seq alignment: a deep learning approach", BMC Genomics, Dec. 27, 2018, 13 Pages.

Zhang, J., et al., "PSFM-DBT: Identifying DNA-Binding Proteins by Combing Position Specific Frequency Matrix and Distance-Bigram Transformation", Int J Moi Sci 18(9) pii: E1856. doi: 10.3390/ijms18091856., Aug. 25, 2017.

Jaganathan et al, Predicting Splicing from Primary Sequence with Deep-Learning, Cell, vol. 176, No. 3, Jan. 1, 2019, 40 pages.

Gandolfi et al, A Computational Approach for the Functional Classification-of the Epigenome, Epigenetics & Chromatin, vol. 10, No. 1, May 15, 2017, 21 pages.

PCT/US2020/051639—International Search Report and Written Opinion dated Jan. 12, 2021, 13 pages.

PCT/US2020/051639—Article 34 Amendments in response to Written Opinion filed Sep. 28, 2021, 14 pages.

PCT/US2020/051639—2nd Article 34 Amendment in response to Written Opinion filed Dec. 21, 2021, 12 pages.

PCT/US2020/051639—International Preliminary Report on Patentability dated Jan. 20, 2022, 19 pages.

Holder et al, "Machine learning for epigenetics and future medical applications", Epigenetics, vol. 12, No. 7, May 19, 2017, 10 pages.

Gehring et al, "Convolutional Sequence to Sequence Learning", Jul. 25, 2017, 15 pages.

ChIP-seq Analysis, BaRC Hot Topics, Bioinformatics and Research Computing, Whitehead Institute, Feb. 23, 2016, 30 pages.

Kimura, Histone modifications for human epigenome analysis, Journal of Human Genetics (2013) 58, pp. 439-445.

Furey, ChIP-seq and Beyond: new and improved methodologies to detect and characterize protein-DNA interactions, Nat Rev Genet. Dec. 2012 13(12): 840-852.

Bailey et al, Practical Guidelines for the Comprehensive Analysis of ChIP-seq Data. PLOS Computational Biology, vol. 9, Issue 11, Nov. 1, 2013.

Rehm, H., et al., "ClinGen—the Clinical Genome Resource", N. Engl. J. Med., 2015, pp. 2235-2242.

Rehm, "Evolving health care through personal genomics", Nature Reviews Genetics, 2017, pp. 259-267.

Reich, et al., "On the allelic spectrum of human disease", Trends in Genetics, 2001, pp. 502-510.

Rentzsch, P., et al., "CADD: predicting the deleterious of variants throughout the human genome", Nucleic Acids Research (1), Sep. 14, 2018, pp. 1-9.

Reva, B., et al., "Predicting the functional impact of protein mutations: application to cancer genomics", Nucleic Acids Res., 2011, 14 pages.

Richards, S., et al., "Standards and guidelines for the interpretation of sequence variants: a joint consensus recommendation of the American College of Medical Genetics and Genomics and the Association for Molecular Pathology", Genet. Med., 2015, pp. 405-424.

(56) References Cited

OTHER PUBLICATIONS

Ritchie, et al., "Functional annotation of noncoding sequence variants", Nature Methods, Feb. 2, 2014, pp. 294-296.

Samocha, K., et al., "A framework for the interpretation of de novo mutation in human disease", Science, 2013, pp. 1578-1582.

Sanders, S., et al., "De novo mutations revealed by whole-exome sequencing are strongly associated with autism", Nature, 2012, pp. 237-241.

Schrago, et al., "Timing the origin of New World monkeys", Molecular Biology, Jun. 27, 2003, pp. 1620-1625.

Schubach, et al., "Imbalance-Aware Machine Learning for Predicting Rare and Common Disease-Associated Non-Coding Variants", Scientific Reports, Jun. 7, 2017, 12 pages.

Schwarz, et al., "MutationTaster evaluates disease-causing potential of sequence alterations", Nature Methods, 2010, pp. 575-576.

Shen, et al., "Structure of a eukaryotic voltage-gated sodium channel at near-atomic resolution", Science, 2017, 19 pages.

Sherry, et al., "dbSNP—the NCBI database of genetic variation", Nucleic Acids Research, 2001, pp. 308-311.

Shihab, et al., "An integrative approach to predicting the functional effects of non-coding and coding sequence variation", Bioinformatics, Jan. 11, 2015, pp. 1536-1543.

Shihab, H., et al., "Predicting the functional, molecular, and phenotypic consequences of amino acid substitutions using hidden Markov models", Human Mutat., 2013, pp. 57-65.

Sittig, et al., "Genetic background limits generalizability of genotype-phenotype relationships", Neuron, Sep. 8, 2016, pp. 1253-1259.

Smedley, et al., "A whole-genome analysis framework for effective identification of pathogenic regulatory variants in mendelian disease", AJ Human Genetics, 2016, pp. 595-606.

Srivastava, et al., "Highway Networks", The Swiss AI Lab, Nov. 3, 2015, 6 pages.

Stenson, P., et al., "The Human Gene Mutation Database: building a comprehensive mutation repository for clinical and molecular genetics, diagnostic testing and personalized genomic medicine", Hum. Genet., 2014, pp. 109.

Sundaram, et al., "Predicting the clinical impact of human mutation with deep neural networks", Nature Genetics, Aug. 2018, pp. 1161-1170.

Szegedy, et al., "Going deeper with convolutions", Sep. 17, 2014, 12 pages.

Takahata, "Allelic genealogy and human evolution", Molecular Biology and Evolution, 1993, pp. 2-22.

The 1000 Genomes Project Consort, "A global reference for human genetic variation", Nature, Oct. 1, 2015, pp. 68-74.

Torng, et al., "3D deep convolutional neural networks for amino acid environment similarity analysis", BMC Bioinformatics, 2017, 23 pages.

Tyner, et al., "The UCSC Genome Browser database: 2017 update", Nucleic Acids Res, 2017, pp. D626-D634.

UNIPROTKB—P04217 (A1BG_HUMAN), "retrieved from https://www.uniprot.org/uniprot/P04217" Mar. 13, 2019, 12 pages.

Van Den Oord, A., "WaveNet: A generative Model for raw audio", Sep. 19, 2016, 15 pages.

Vissers, L., et al., "Genetic studies in intellectual disability and related disorders", Nat. Rev. Genet., 2016, pp. 9-18.

Wang, et al., "Protein secondary structure prediction using deep convolutional neural fields", Scientific Reports, Jan. 11, 2016, 1 page.

Waterston, et al., "Initial sequence of the chimpanzee genome and comparison with the human genome—The Chimpanzee Sequencing and Analysis Consortium" Nat., Sep. 1, 2005 pp. 69-87.

Wei, Q., et al., "Prediction of phenotypes of missense mutations in human proteins from biological assemblies", Proteins 81(2), Feb. 2013, pp. 199-213.

Wei, et al., "The Role of Balanced Training and Testing Data Sets for Binary Classifiers in Bioinformatics", PLoS One, Jul. 9, 2013, 12 pages.

Whiffin, et al., "Using high-resolution variant frequencies to empower clinical genome interpretation", Genetics in Medicine, Oct. 2017, pp. 1151-1158.

Wolterink, et al., "Dilated Convolutional Neural Networks for Cardiovascular MR Segmentation in Congenital Heart Disease", Apr. 21, 2017, 9 pages.

Worley, et al., "The common marmoset genome provides insight into primate biology and evolution", Nature Genetics, 2014, pp. 850-857.

Wu, J., "Introduction to Convolutional Neural Networks", National Key Lab for Novel Software Technology, May 1, 2017, 31 pages.

Xiong, et al., "The human splicing code reveals new insights into the genetic determinants of disease", Science, Dec. 18, 2014, pp. 1-10.

Yu, et al., "Multi-scale context aggregation by dilated convolutions", Apr. 30, 2016, 13 pages.

Yue, et al., "Deep Learning for Genomics: A Concise Overview", School of Computer Science, May 8, 2018, 40 pages.

Yuen, et al., "Genome-wide characteristics of de novo mutations in autism", Genomic Medicine, Jun. 13, 2016, 10 pages.

Zhou, et al., "Predicting effects of noncoding variants with deep learning-based sequence model", Nature Methods, Oct. 2015, pp. 931-934.

Zhu, X., et al., "One gene, many neuropsychiatric disorders: lessons from Mendelian diseases", Nat. Neurosci., 2014, pp. 773-781.

Zou, J., et al., "A primer on deep learning in genomics", Nature Genetics, Nov. 26, 2018, 7 pages.

DbSNP re2241788, (retrieved on Mar. 13, 2019) from the internet <https://www.ncbi.nlm.nih.gov/snp/re2241788>, Oct. 2, 2018; email to Roland Dunbrack from Sikander Mohammed Khan dated Feb. 3, 2019 in re Question about Paper entitled "The Role of Balanced Training and Testing Data Sets for Binary Classifiers in Bioinformatics"; 3 pgs.

"Large-scale discovery of novel genetic causes of developmental disorders—Deciphering Developmental Disorders Study", Nature, vol. 519, Mar. 12, 2015, 15 pgs.

"Evolutionary and Biomedical Insights from the Rhesus Macaque Genome", Rhesus Macaque Genome Sequencing and Analysis Consortium, Science, Apr. 13, 2007, pp. 222-234.

Adzhubei, et al., "A method and server for predicting damaging missense mutations", Nature Methods, 2010, pp. 248-249.

Alberts, B., et al., "How Cells Read the Genome: From DNA to Protein", Molecular biology of the cell, 6th Edition, 2015, 3 pgs.

Alipanahi, et al., "Predicting the sequence specificities of DNA- and RNA-binding proteins by deep learning", Computational Biology, Aug. 2015, 9 pgs.

Angermueller, et al., "Accurate prediction of single-cell DNA methylation states using deep learning", Apr. 11, 2017, 33 pgs.

Angermueller, et al., "Deep learning for computational biology", Molecular Systems Biology, Jun. 6, 2016, 16 pgs.

Arik, et al., "Deep Voice: Real-time Neural Text-to-Speech", International Conference on Machine Learning, Feb. 24, 2017, 17 pgs.

Asthana, et al., "A limited role for balancing selection", Trends in Genetics, Jan. 2005, pp. 30-32.

Bahar, "Proteins Change Through Evolutionary Processes", Proteins Evolve, Chapter 7, 2017, pp. 165-166.

Bamshad, et al., "Exome sequencing as a tool for Mendelian Disease Gene Discovery", Nature Reviews Genetics, Nov. 1, 2011, pp. 745-755.

Bazykin, et al., "Extensive parallelism in protein evolution", Biology Direct, Aug. 16, 2007, 13 pgs.

Bell, et al., "Carrier testing for severe childhood recessive diseases by next-generation sequencing", Science Translational Medicine, 2011, 28 pgs.

Brandon, et al., "Targeting the mouse genome: a compendium of knockouts (Part II)", Current Biology, 1995, pp. 758-765.

Brookes, A., "The essence of SNPs", Gene 234, 1999, pp. 177-186.

Carter, H., et al., "Cancer-Specific High-Throughput Annotation of Somatic Mutations: Computational Prediction of Driver Missense Mutations", Cancer Res, Aug. 4, 2009, pp. 6660-6667.

Carter, et al., "Identifying Mendelian disease genes with the variant effect scoring tool", BMC Genomics, 2013, 13 pgs.

(56)                    References Cited

OTHER PUBLICATIONS

Chen, K., et al., "Selene: a PyTorch-based deep learning library for sequence-level data", http://dx.doi.prg/10.1101/438291., Oct. 10, 2018, pp. 1-15.
Ching, et al., "Opportunities and Obstacles for Deep Learning in Biology and Medicine", May 26, 2017, pp. 1-47.
Ching, T., et al., "Opportunities and obstacles for deep learning in biology and medicine", "https://doi.org/10.1101/142760.", Jan. 19, 2018, 123 pgs.
Choi, et al., "Predicting the functional effect of amino acid substitutions and indels", PLoS One, 2012, 13 pgs.
Chun, et al., "Identification of deleterious mutations within three human genomes", Genome Research, 2009, pp. 1553-1561.
Davydov, et al., "Identifying a high fraction of the human genome to be under selective constraint using GERP++", PLoS Comput Biol., 2010, 13 pgs.
De Ligt, J., et al., "Diagnostic exome sequencing in persons with severe intellectual disability", N. Engl. J. Med., 2012, pp. 1921-1929.
De Manuel, et al., "Chimpanzee genomic diversity reveals ancient admixture with bonobos", Science, Oct. 28, 2016, pp. 477-481.
De Rubeis, S., et al., "Synaptic, transcriptional and chromatin genes disrupted in autism", Nature, 2014, pp. 209-215.
Dong, et al., "Comparison and integration of deleteriousness prediction methods for nonsynonymous SNVs in whole exome sequencing studies", Human Molecular Genetics, 2015, pp. 2125-2137.
Duggirala, R., et al., "Genome Mapping and Genomics in Human and Non-Human Primates Springer", vol. 5, 2015, pp. 1-305.
Epi, K., et al., "De novo mutations in the classic epileptic encephalopathies Nature", 2013, pp. 217-221.
Estrada, A., et al., "Impending extinction crisis of the world's primates: why primates matter", Sci Adv., 2017, 17 pgs.
Euroepinomics-Res Consortium, et al., "De novo mutations in synaptic transmission genes including DNM1 cause epileptic encephalopathies", The American Journal of Human Genetics, Oct. 2, 2014, pp. 360-370.
Famiglietti, M., et al., "Genetic variations and diseases in UniProtKB/Swiss-Prot: the ins and outs of expert manual curation", Human mutat., 2014, pp. 927-935.
Gilissen, C., et al., "Genome sequencing identifies major causes of severe intellectual disability", Nature, 2014, pp. 344-347.
Goodfellow, et al., "Convolutional Networks—Chapter 9", http://www.deeplearningbook.org/contents/convnets.html, Oct. 14, 2017, 41 pages.
Grantham, R., "Amino acid difference formula to help explain protein evolution", Science, 1974, pp. 862-864.
Grimm, D., "The evaluation of tools used to predict the impact of missense variants is hindered by two types of circularity", Human. Mutat., 2015, pp. 513-523.
Grob, C., et al., "Predicting variant deleteriousness in non-human species Applying the CADD approach in mouse", 2018, pp. 1-11.
Gu, et al., "Recent Advances in Convolutional Neural Networks", Nanyang Technological University, Singapore, Jan. 5, 2017, 37 pages.
Gulko, et al., "A method for calculating probabilities of fitness consequences for point mutations across the human genome", Nature Genetics, Jan. 19, 2015, pp. 276-283.
Harpak, et al., "Mutation rate variation is a primary determinant of the distribution of allele frequencies in humans", PLoS Genetics, Dec. 15, 2016, 22 pages.
He, K., et al., "Deep Residual Learning for Image Recognition", Microsoft Research, Dec. 2015, 12 pages.
He, K., et al., "Identity mappings in deep residual networks. in 14th European Conference on Computer Vision—ECCV 2016", Lecture Notes in Computer Science, 2016, pp. 630-645.
Hefferman, et al., "Improving prediction of secondary structure, local backbone angles, and solvent accessible surface area of proteins by iterative deep learning", Scientific Reports, Jun. 22, 2015, 11 pages.

Henikoff, et al., "Amino Acid Substitution Matrices from Protein Blocks", PNAS USA, 1992, pp. 10915-10919.
Horaitis, O., et al., "A database of locus-specific databases", Nat. Genet., 2007.
Huang, G., et al., "Densely Connected Convolutional Networks", Aug. 27, 2017, 9 pages.
Ioannidis, et al., "REVEL: An Ensemble Method for Predicting the Pathogenicity of Rare Missense Variants", American Journal of Human Genetics, Oct. 5, 2016, pp. 877-885.
Ioffe, et al., "Batch Normalization: Accelerating Deep Network Training by Reducing Internal Covariate Shift", arXiv:1502.03167 [cs.LG], Feb. 11, 2015, 11 pages.
Ionita-Laza, I., et al., A spectral approach integrating functional genomic annotations for coding and noncoding variants:, Nat. Genet., 2016, pp. 214-220.
Iossifov, I., et al., "De novo gene disruptions in children on the autistic spectrum", Neuron, 2012, pp. 285-299.
Iossifov, I., et al., "The contribution of de novo coding mutations to autism spectrum disorder", Nature, 2014, pp. 216-221.
Jagadeesh, et al., "M-CAP eliminates a majority of variants of uncertain significance in clinical exomes at high sensitivity", Nature Genetics, Oct. 24, 2016, pp. 1581-1586.
Jain, S., et al., "Recovering true classifier performance in positive-unlabeled learning", Thirty-First AAAI Conference on Artificial Intelligence, 2017, pp. 2066-2072.
Joosten, et al., "A series of PDB related databases for everyday needs", Nucleic Acids Research, 2011, pp. 411-419.
Kabsch, W., et al., "Dictionary of protein secondary structure: pattern recognition of hydrogen-bonded and geometrical features", Biopolymers, 1983, pp. 2577-2637.
Kent, W., et al., "The human genome browser at UCSC", Genome Res., 2002, pp. 996-1006.
Kircher, et al., "A general framework for estimating the relative pathogenicity of human genetic variants", Nature Genetics, 2014, pp. 310-315.
Klein, et al., "The molecular descent of the major histocompatibility complex", Annual Review of Immunology, 1993, pp. 269-295.
Landrum, et al., ClinVar: public archive of interpretations of clinically relevant variants:, Nucleic Acids Research, Nov. 17, 2015, D862-D868.
Lecun, Y., et al., "Gradient based learning applied to document recognition", Proc. IEEE, 1998, pp. 2278-2324.
Lee, et al., "A method to predict the impact of regulatory variants from DNA sequence", Nature Genetics, Jun. 15, 2015, pp. 955-961.
Leffler, et al., "Multiple instances of ancient balancing selection shared between humans and chimpanzees", Science, Feb. 14, 2013, 12 pages.
Leffler, et al., "Revisiting an old riddle: what determines genetic diversity levels within species?", PLoS Biol., 2012, 9 pages.
Lek, M., et al., "Analysis of protein-coding genetic variation in 60,706 humans", Genet. Med. Nature, Aug. 18, 2016, pp. 285-291.
Lelieveld, S., et al., "Meta-analysis of 2,104 trios provides support for 10 new genes for intellectual disability", Nat. Neurosci, 2016, pp. 1194-1196.
Leung, M., et al., "Deep Learning of the tissue-regulated splicing code", Bioinformatics, Jul. 23, 2014, pp. 121-129.
Leung, M., et al., "Inference of the Human Polyadenylation Code", bioRxiv, 2017, 13 pages.
Leung, M., et al., "Machine Learning in Genomic Medicine: A Review of Computational Problems and Data Sets", IEEE, Jan. 2016, pp. 176-197.
Li, B., et al., "Automated inference of molecular mechanisms of disease from amino acid substitutions", Bioinformatics, 2009, pp. 2744-2750.
Li, Y., et al., "FoldingZero: Protein Folding from Scratch in Hydrophobic-Polar Model", Dec. 3, 2018, pp. 1-10.
Li, W., et al., "Nonrandomness of point mutation as reflected in nucleotide substitutions in pseudogenes and its evolutionary implications", J. Molec. Evol., 1984, pp. 58-71.
Libbrecht, et al., "Machine learning in genetics and genomics", Nature Reviews Genetics, Jun. 2015, pp. 321-332.
Lieschke, et al., "Animal models of human disease: zebrafish swim into view", Nature Reviews Genetics, May 2007, pp. 353-367.

(56) References Cited

OTHER PUBLICATIONS

Liu, et al., "dbNSFP: A lightweight database of human nonsynonymous SNPs and their functional predictions", Human Mutation, Apr. 21, 2011, pp. 894-899.

Liu, X., et al., "dbNSFPv3.0: a one-stop database of functional predictions and annotations for human nonsynonymous and splice-site SNVs", Human Mutat., 2016, pp. 235-241.

Locke, D., et al., "Comparative and demographic analysis of orang-utan genomes", Nature, 2011, pp. 529-533.

Lu, Q., et al., "A statistical framework to predict functional non-coding regions in the human genome through integrated analysis of annotation data", Sci Rep. 2015, 13 pgs.

Macarthur, D., et al., "Guidelines for investigating causality of sequence variants in human disease", Nature, 2014, pp. 469-476.

Mallick, S, et al., "The Simons Genome Diversity Project: 300 genomes from 142 diverse populations", Nature, 2016, pp. 201-206.

McRae, et al., "Prevalence and architecture of de novo mutations in developmental disorders", Nature 542 (7642), Jun. 25, 2018, pp. 433-439.

Min, et al., "Deep learning in bioinformatics", Briefings in Bioinformatics, Jul. 25, 2016, pp. 851-869.

Nakamura, et al., "Clinical spectrum of SCN2A mutations expanding to Ohtahara syndrome", Neurology, 2013, pp. 992-998.

Neale, B., et al., "Patterns and rates of exonic de novo mutations in autism spectrum disorders", Nature, 2012, pp. 242-245.

Ng, et al., "Predicting deleterious amino acid substitutions", Genome Res., 2001, pp. 863-874.

Ohta, T., et al., "Slightly deleterious mutant substitutions in evolution", Nature, 1973, pp. 96-98.

O'Roak, B., et al., "Sporadic autism exomes reveal a highly interconnected protein network of de novo mutations", Nature, 2012, pp. 246-250.

Park, Y., et al., "Deep learning for regulatory genomics", News and Views, 2015, 2 pages.

Payandeh, et al., "The crystal structure of a voltage-gated sodium channel", Nature, 2011, pp. 353-358.

Piqueras, L., "Autoregressive Model Based on a Deep Convolutional Neural Network for Audio Generation", Master of Science Thesis, Dec. 7, 2016, 58 pages.

Prado-Martinez, et al., "Great ape genetic diversity and population history", Nature, Jul. 25, 2013, pp. 471-475.

Quang, D., et al., "DANN: a deep learning approach for annotating the pathogenicity of genetic variants", Bioinformatics, 2015, pp. 761-763.

Quang, et al., "DanQ: a hybrid convolutional and recurrent deep neural network for quantifying the function of DNA sequences", Nucleic Acids Research, Apr. 15, 2016, 6 pgs.

Rauch, A., et al., "Range of genetic mutations associated with severe non-syndromic sporadic intellectual disability: an exome sequencing study", Lancet, 2012, pp. 1674-1682.

* cited by examiner

Convolutional Neural Network

Training Convolutional Neural Network

FIG. 4

Non-Linear Layers of Convolutional Neural Networks

| 0 | 76 | 0 | 100 |
|---|---|---|---|
| 21 | 40 | 0 | 0 |
| 0 | 1 | 44 | 0 |
| 23 | 41 | 64 | 221 |

0,0

| -21 | 76 | -43 | 100 |
|---|---|---|---|
| 21 | 40 | -10 | -90 |
| -35 | 1 | 44 | -19 |
| 23 | 41 | 64 | 221 |

ReLU Activation Function

FIG. 5

Sub-Sampling Layers of Convolutional Neural Networks

Feature Map

Max Pooling

Average Pooling

Convolution Layers of Convolutional Neural Networks

Residual Connections used in Convolutional Neural Networks

Residual Block and Skip-Connections used in
Convolutional Neural Networks

Batch Normalization Forward Pass with Convolutional Neural Networks $$\mu_{\mathcal{B}} = \frac{1}{n} \sum_{i=1}^{n} x_i^{(\ell-1)}$$

$$\sigma_{\mathcal{B}}^2 = \frac{1}{n} \sum_{i=1}^{n} \left( x_i^{(\ell-1)} - \mu_{\mathcal{B}} \right)^2$$

$$\hat{x}^{(\ell-1)} = \frac{x^{(\ell-1)} - \mu_{\mathcal{B}}}{\sqrt{\sigma_{\mathcal{B}}^2 + \epsilon}}$$

$$x^{(\ell)} = \gamma^{(\ell)} \hat{x}^{(\ell-1)} + \beta^{(\ell)}$$

FIG. 12

Batch Normalization – Inference with Convolutional
Neural Networks $$\hat{x}^{(\ell-1)} = \frac{x^{(\ell-1)} - \mu_D}{\sqrt{\sigma_D^2 + \epsilon}}$$

$$x_i^{(\ell)} = \gamma^{(\ell)}\hat{x}_i^{(\ell-1)} + \beta^{(\ell)}$$

FIG. 13

Batch Normalization Backward Pass with
Convolutional Neural Networks $$\nabla_{\gamma^{(\ell)}} \mathcal{L} = \sum_{i=1}^{n} \left( \nabla_{x^{(\ell+1)}} \mathcal{L} \right)_i \cdot \hat{x}_i^{(\ell)}$$

$$\nabla_{\beta^{(\ell)}} \mathcal{L} = \sum_{i=1}^{n} \left( \nabla_{x^{(\ell+1)}} \mathcal{L} \right)_i$$

FIG. 14

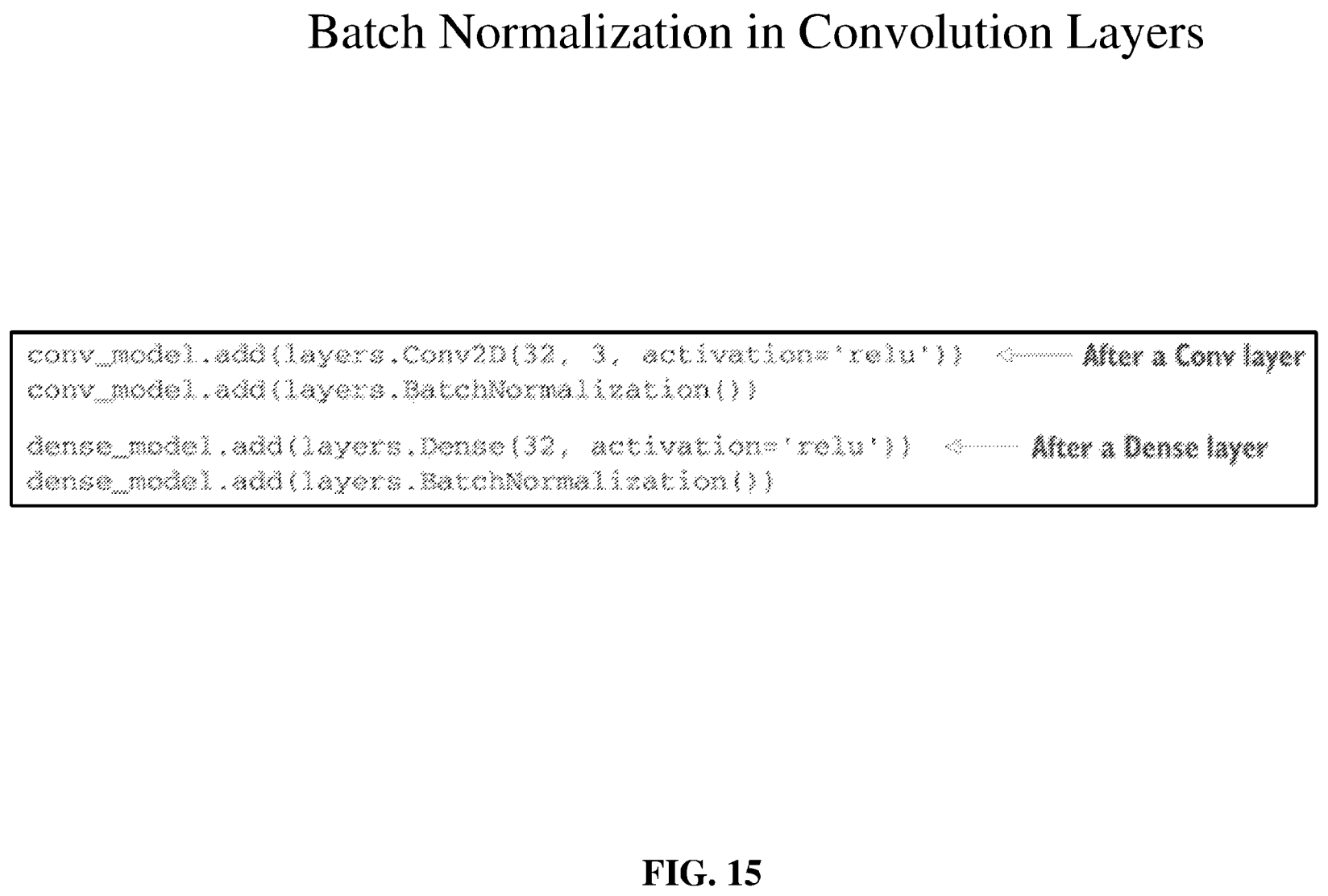

Batch Normalization in Convolution Layers

```
conv_model.add(layers.Conv2D(32, 3, activation='relu'))    <——— After a Conv layer
conv_model.add(layers.BatchNormalization())

dense_model.add(layers.Dense(32, activation='relu'))    <——— After a Dense layer
dense_model.add(layers.BatchNormalization())
```

FIG. 15

Global Average Pooling (GAP) in Convolutional Neural Networks

Model

Residual Block (RB) (N, W, D)

N: Number of Convolution Filters
W: Convolution Window Size
D: Atrous Convolution Rate Model80

Model10000

$C^u$: 5000, $C^d$: 5000

|   | A | C | G | T | T | T | G | C | A | C | A | C | G | ? | G | T | A | T | A | T |
|---|---|---|---|---|---|---|---|---|---|---|---|---|---|---|---|---|---|---|---|---|
| A | 1 | 0 | 0 | 0 | 0 | 0 | 0 | 0 | 1 | 0 | 1 | 0 | 0 | 0 | 0 | 0 | 1 | 0 | 1 | 0 |
| C | 0 | 1 | 0 | 0 | 0 | 0 | 0 | 1 | 0 | 1 | 0 | 1 | 0 | 0 | 0 | 0 | 0 | 0 | 0 | 0 |
| G | 0 | 0 | 1 | 0 | 0 | 0 | 1 | 0 | 0 | 0 | 0 | 0 | 1 | 0 | 1 | 0 | 0 | 0 | 0 | 0 |
| T | 0 | 0 | 0 | 1 | 1 | 1 | 0 | 0 | 0 | 0 | 0 | 0 | 0 | 0 | 0 | 1 | 0 | 1 | 0 | 1 |
| N | 0 | 0 | 0 | 0 | 0 | 0 | 0 | 0 | 0 | 0 | 0 | 0 | 0 | 0 | 0 | 0 | 0 | 0 | 0 | 0 |

One-hot Encoding

Expression outliers

- GTEx: RNA-seq and WGS across >500 individuals in 48 tissues.

- Expression outliers: Singleton non-coding variants within 1.5Kb from TSS that are associated with extreme under-expression (z-score < -1.5) across >1 tissues.
  - 1490 variants

- Negative set: Singleton variants not associated with under-expression (matched for AF, nearest gene expression levels etc).

ARTIFICIAL INTELLIGENCE-BASED EPIGENETICS

PRIORITY DATA

This application claims priority to or the benefit of U.S. Provisional Patent Application No. 62/903,700, titled, "ARTIFICIAL INTELLIGENCE-BASED EPIGEN-ETICS," filed Sep. 20, 2019.

INCORPORATIONS

The following are incorporated by reference for all purposes as if fully set forth herein:

PCT Patent Application No. PCT/US18/55915, titled "Deep Learning-Based Splice Site Classification," by Kishore Jaganathan, Kai-How Farh, Sofia Kyriazopoulou Panagiotopoulou and Jeremy Francis McRae, filed on Oct. 15, 2018, subsequently published as PCT Publication No. WO 2019/079198;

PCT Patent Application No. PCT/US18/55919, titled "Deep Learning-Based Aberrant Splicing Detection," by Kishore Jaganathan, Kai-How Farh, Sofia Kyriazopoulou Panagiotopoulou and Jeremy Francis McRae, filed on Oct. 15, 2018, subsequently published as PCT Publication No. WO 2019/079200;

PCT Patent Application No. PCT/US18/55923, titled "Aberrant Splicing Detection Using Convolutional Neural Networks (CNNs)," by Kishore Jaganathan, Kai-How Farh, Sofia Kyriazopoulou Panagiotopoulou and Jeremy Francis McRae, filed Oct. 15, 2018, subsequently published as PCT Publication No. WO 2019/079202;

U.S. patent application Ser. No. 16/160,978, titled "Deep Learning-Based Splice Site Classification," by Kishore Jaganathan, Kai-How Farh, Sofia Kyriazopoulou Panagiotopoulou and Jeremy Francis McRae, filed Oct. 15, 2018;

U.S. patent application Ser. No. 16/160,980, titled "Deep Learning-Based Aberrant Splicing Detection," by Kishore Jaganathan, Kai-How Farh, Sofia Kyriazopoulou Panagiotopoulou and Jeremy Francis McRae, filed Oct. 15, 2018;

U.S. patent application Ser. No. 16/160,984, titled "Aberrant Splicing Detection Using Convolutional Neural Networks (CNNs)," by Kishore Jaganathan, Kai-How Farh, Sofia Kyriazopoulou Panagiotopoulou and Jeremy Francis McRae, filed Oct. 15, 2018;

Document 1—S. Dieleman, H. Zen, K. Simonyan, O. Vinyals, A. Graves, N. Kalchbrenner, A. Senior, and K. Kavukcuoglu, "WAVENET: A GENERATIVE MODEL FOR RAW AUDIO," arXiv:1609.03499, 2016;

Document 2—S. Ö. Arik, M. Chrzanowski, A. Coates, G. Diamos, A. Gibiansky, Y. Kang, X. Li, J. Miller, A. Ng, J. Raiman, S. Sengupta and M. Shoeybi, "DEEP VOICE: REAL-TIME NEURAL TEXT-TO-SPEECH," arXiv:1702.07825, 2017;

Document 3—F. Yu and V. Koltun, "MULTI-SCALE CONTEXT AGGREGATION BY DILATED CON-VOLUTIONS," arXiv:1511.07122, 2016;

Document 4—K. He, X. Zhang, S. Ren, and J. Sun, "DEEP RESIDUAL LEARNING FOR IMAGE REC-OGNITION," arXiv:1512.03385, 2015;

Document 5—R. K. Srivastava, K. Greff, and J. Schmidhuber, "HIGHWAY NETWORKS," arXiv: 1505.00387, 2015;

Document 6—G. Huang, Z. Liu, L. van der Maaten and K. Q. Weinberger, "DENSELY CONNECTED CON-VOLUTIONAL NETWORKS," arXiv:1608.06993, 2017;

Document 7—C. Szegedy, W. Liu, Y. Jia, P. Sermanet, S. Reed, D. Anguelov, D. Erhan, V. Vanhoucke, and A. Rabinovich, "GOING DEEPER WITH CONVOLU-TIONS," arXiv: 1409.4842, 2014;

Document 8—S. Ioffe and C. Szegedy, "BATCH NOR-MALIZATION: ACCELERATING DEEP NETWORK TRAINING BY REDUCING INTERNAL COVARI-ATE SHIFT," arXiv: 1502.03167, 2015;

Document 9—J. M. Wolterink, T. Leiner, M. A. Viergever, and I. Išgum, "DILATED CONVOLUTIONAL NEU-RAL NETWORKS FOR CARDIOVASCULAR MR SEGMENTATION IN CONGENITAL HEART DIS-EASE," arXiv:1704.03669, 2017;

Document 10—L. C. Piqueras, "AUTOREGRESSIVE MODEL BASED ON A DEEP CONVOLUTIONAL NEURAL NETWORK FOR AUDIO GENERATION," Tampere University of Technology, 2016;

Document 11—J. Wu, "Introduction to Convolutional Neural Networks," Nanjing University, 2017;

Document 12—I. J. Goodfellow, D. Warde-Farley, M. Mirza, A. Courville, and Y. Bengio, "CONVOLU-TIONAL NETWORKS", Deep Learning, MIT Press, 2016; and Document 13—J. Gu, Z. Wang, J. Kuen, L. Ma, A. Shahroudy, B. Shuai, T. Liu, X. Wang, and G. Wang, "RECENT ADVANCES IN CONVOLUTIONAL NEURAL NETWORKS," arXiv:1512.07108, 2017.

Document 1 describes deep convolutional neural network architectures that use groups of residual blocks with convolution filters having same convolution window size, batch normalization layers, rectified linear unit (abbreviated ReLU) layers, dimensionality altering layers, atrous convolution layers with exponentially growing atrous convolution rates, skip connections, and a softmax classification layer to accept an input sequence and produce an output sequence that scores entries in the input sequence. The technology disclosed uses neural network components and parameters described in Document 1. In one implementation, the technology disclosed modifies the parameters of the neural network components described in Document 1. For instance, unlike in Document 1, the atrous convolution rate in the technology disclosed progresses non-exponentially from a lower residual block group to a higher residual block group. In another example, unlike in Document 1, the convolution window size in the technology disclosed varies between groups of residual blocks.

Document 2 describes details of the deep convolutional neural network architectures described in Document 1.

Document 3 describes atrous convolutions used by the technology disclosed. As used herein, atrous convolutions are also referred to as "dilated convolutions". Atrous/dilated convolutions allow for large receptive fields with few train-able parameters. An atrous/dilated convolution is a convolution where the kernel is applied over an area larger than its length by skipping input values with a certain step, also called atrous convolution rate or dilation factor. Atrous/dilated convolutions add spacing between the elements of a convolution filter/kernel so that neighboring input entries (e.g., nucleotides, amino acids) at larger intervals are considered when a convolution operation is performed. This enables incorporation of long-range contextual dependencies in the input. The atrous convolutions conserve partial convolution calculations for reuse as adjacent nucleotides are processed.

Document 4 describes residual blocks and residual connections used by the technology disclosed.

Document 5 describes skip connections used by the technology disclosed. As used herein, skip connections are also referred to as "highway networks".

Document 6 describes densely connected convolutional network architectures used by the technology disclosed.

Document 7 describes dimensionality altering convolution layers and modules-based processing pipelines used by the technology disclosed. One example of a dimensionality altering convolution is a 1×1 convolution.

Document 8 describes batch normalization layers used by the technology disclosed.

Document 9 also describes atrous/dilated convolutions used by the technology disclosed.

Document 10 describes various architectures of deep neural networks that can be used by the technology disclosed, including convolutional neural networks, deep convolutional neural networks, and deep convolutional neural networks with atrous/dilated convolutions.

Document 11 describes details of a convolutional neural network that can be used by the technology disclosed, including algorithms for training a convolutional neural network with subsampling layers (e.g., pooling) and fully-connected layers.

Document 12 describes details of various convolution operations that can be used by the technology disclosed.

Document 13 describes various architectures of convolutional neural networks that can be used by the technology disclosed.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep learning-based techniques for training deep convolutional neural networks.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Machine Learning

In machine learning input variables are used to predict an output variable. The input variables are often called features and are denoted by $X=(X_1, X_2, \ldots, X_k)$, where each $X_i$, $i \in 1, \ldots, k$ is a feature. The output variable is often called the response or dependent variable and is denoted by the variable $Y_i$. The relationship between Y and the corresponding X can be written in a general form:

$$Y = f(X) + \in$$

In the equation above, $f$ is a function of the features $(X_1, X_2, \ldots, X_k)$ and $\in$ is the random error term. The error term is independent of X and has a mean value of zero.

In practice, the features X are available without having Y or knowing the exact relation between X and Y. Since the error term has a mean value of zero, the goal is to estimate $f$.

$$\hat{Y} = \hat{f} = (X)$$

In the equation above, $\hat{f}$ is the estimate of $\in$, which is often considered a black box, meaning that only the relation between the input and output of $\hat{f}$ is known, but the question why it works remains unanswered.

The function $\hat{f}$ is found using learning. Supervised learning and unsupervised learning are two ways used in machine learning for this task. In supervised learning, labeled data is used for training. By showing the inputs and the corresponding outputs (=labels), the function $\hat{f}$ is optimized such that it approximates the output. In unsupervised learning, the goal is to find a hidden structure from unlabeled data. The algorithm has no measure of accuracy on the input data, which distinguishes it from supervised learning.

Neural Networks

The single layer perceptron (SLP) is the simplest model of a neural network. It comprises one input layer and one activation function as shown in FIG. 1. The inputs are passed through the weighted graph. The function $f$ uses the sum of the inputs as argument and compares this with a threshold $\theta$.

FIG. 2 shows one implementation of a fully connected neural network with multiple layers. A neural network is a system of interconnected artificial neurons (e.g., $a_1$, $a_2$, $a_3$) that exchange messages between each other. The illustrated neural network has three inputs, two neurons in the hidden layer and two neurons in the output layer. The hidden layer has an activation function $f$ (•) and the output layer has an activation function g(•). The connections have numeric weights (e.g., $w_{11}$, $w_{21}$, $w_{12}$, $w_{31}$, $w_{22}$, $w_{32}$, $v_{11}$, $v_{22}$) that are tuned during the training process, so that a properly trained network responds correctly when fed an image to recognize. The input layer processes the raw input, the hidden layer processes the output from the input layer based on the weights of the connections between the input layer and the hidden layer. The output layer takes the output from the hidden layer and processes it based on the weights of the connections between the hidden layer and the output layer. The network includes multiple layers of feature-detecting neurons. Each layer has many neurons that respond to different combinations of inputs from the previous layers. These layers are constructed so that the first layer detects a set of primitive patterns in the input image data, the second layer detects patterns of patterns and the third layer detects patterns of those patterns.

Genetic variations can help explain many diseases. Every human being has a unique genetic code and there are lots of genetic variants within a group of individuals. Most of the deleterious genetic variants have been depleted from genomes by natural selection. It is important to identify which genetics variations are likely to be pathogenic or deleterious. This will help researchers focus on the likely pathogenic genetic variants and accelerate the pace of diagnosis and cure of many diseases.

Modeling the properties and functional effects (e.g., pathogenicity) of variants is an important but challenging task in the field of genomics. Despite the rapid advancement of functional genomic sequencing technologies, interpretation of the functional consequences of non-coding variants remains a great challenge due to the complexity of cell type-specific transcription regulation systems. In addition, a limited number of non-coding variants have been functionally validated by experiments.

Previous efforts on interpreting genomic variants have mainly concentrated on variants in the coding regions. However, the non-coding variants also play an important role in complex diseases. Identifying the pathogenic functional non-coding variants from the massive neutral ones can be important in genotype-phenotype relationship research and precision medicine.

Furthermore, most of the known pathogenic non-coding variants reside in the promoter regions or conserved sites, causing ascertainment bias in the training set because easy or obvious cases known for pathogenic tendencies are likely to be enriched in labeled data sets relative to the entire population of the pathogenic non-coding variants. If left unaddressed, this bias in the labeled pathogenic data would lead to unrealistic model performance, as a model could achieve relatively high test set performance simply by predicting that all core variants are pathogenic and all others are benign. However, in the clinic, such a model would incorrectly classify pathogenic, non-core variants as benign at an unacceptably high rate.

Advances in biochemical technologies over the past decades have given rise to next generation sequencing (NGS) platforms that quickly produce genomic data at much lower costs than ever before. Such overwhelmingly large volumes of sequenced DNA remain difficult to annotate. Supervised machine learning algorithms typically perform well when large amounts of labeled data are available. In bioinformatics and many other data-rich disciplines, the process of labeling instances is costly; however, unlabeled instances are inexpensive and readily available. For a scenario in which the amount of labeled data is relatively small and the amount of unlabeled data is substantially larger, semi-supervised learning represents a cost-effective alternative to manual labeling.

An opportunity arises to construct deep learning-based pathogenicity classifiers that accurately predict pathogenicity of non-coding variants. Databases of pathogenic non-coding variants that are free from human ascertainment bias may result.

BRIEF DESCRIPTION OF THE DRAWINGS

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

Figure 4:
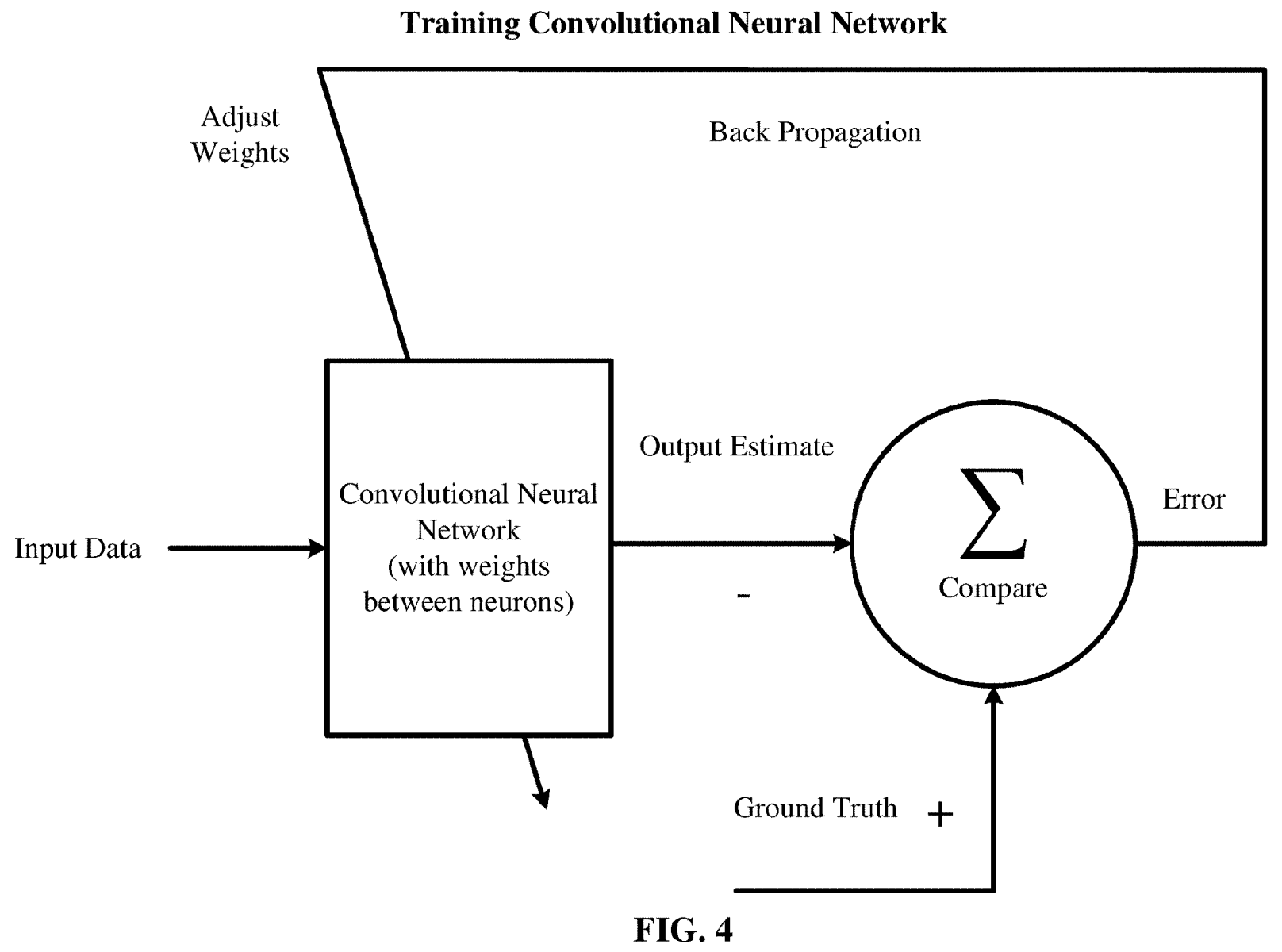

FIG. 4 depicts a block diagram of training a convolutional neural network in accordance with one implementation of the technology disclosed.

FIG. 5 shows one implementation of a ReLU non-linear layer in accordance with one implementation of the technology disclosed.

FIG. 12 shows the batch normalization forward pass.

FIG. 13 illustrates the batch normalization transform at test time.

FIG. 14 shows the batch normalization backward pass.

FIG. 15 depicts use of a batch normalization layer with convolutional or densely connected layer.

FIG. 25 illustrates a one-hot encoder.

DETAILED DESCRIPTION

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

Residual Connections

Figure 1:
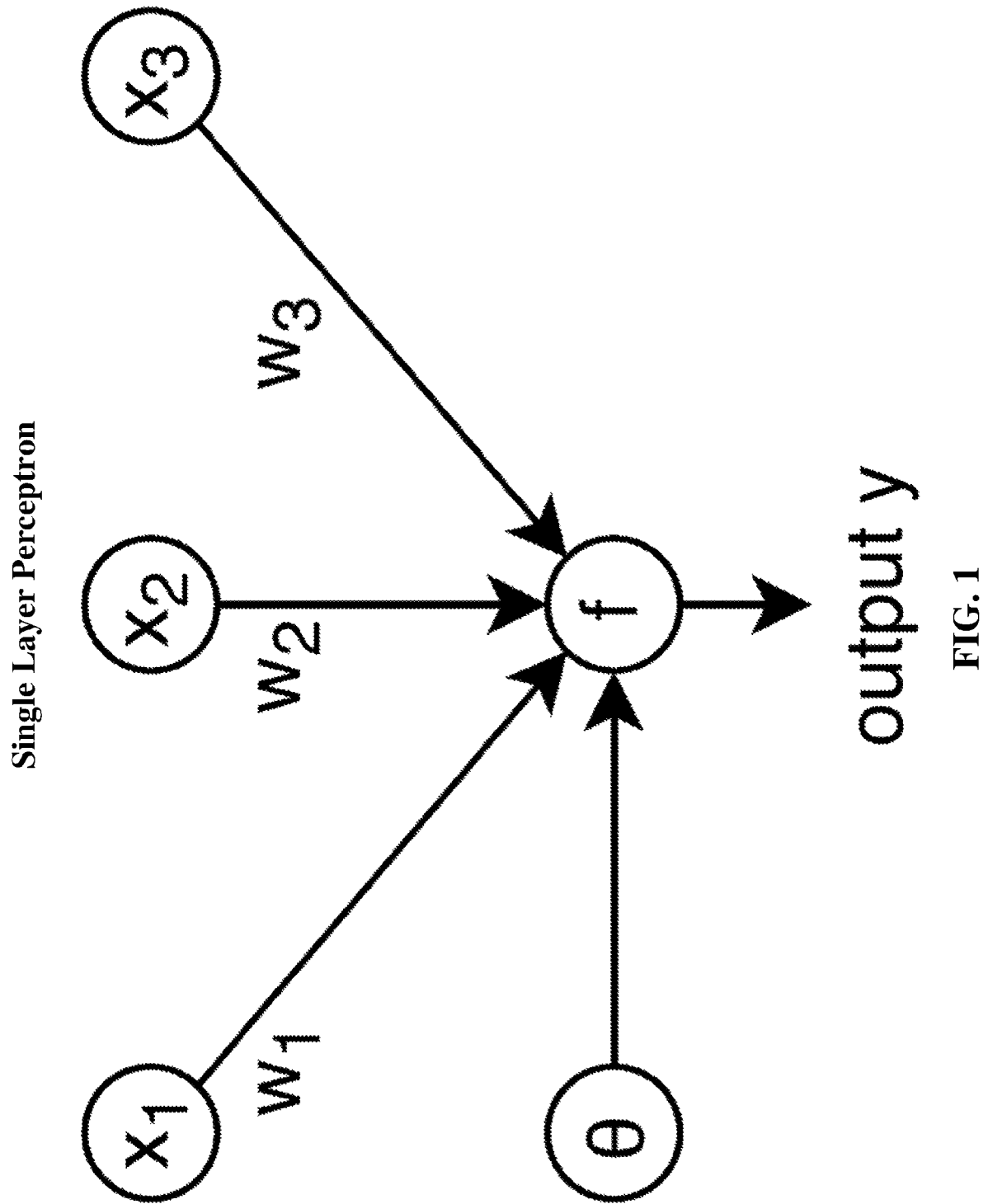
FIG. 1 shows a single layer perceptron (SLP).
Figure 2:
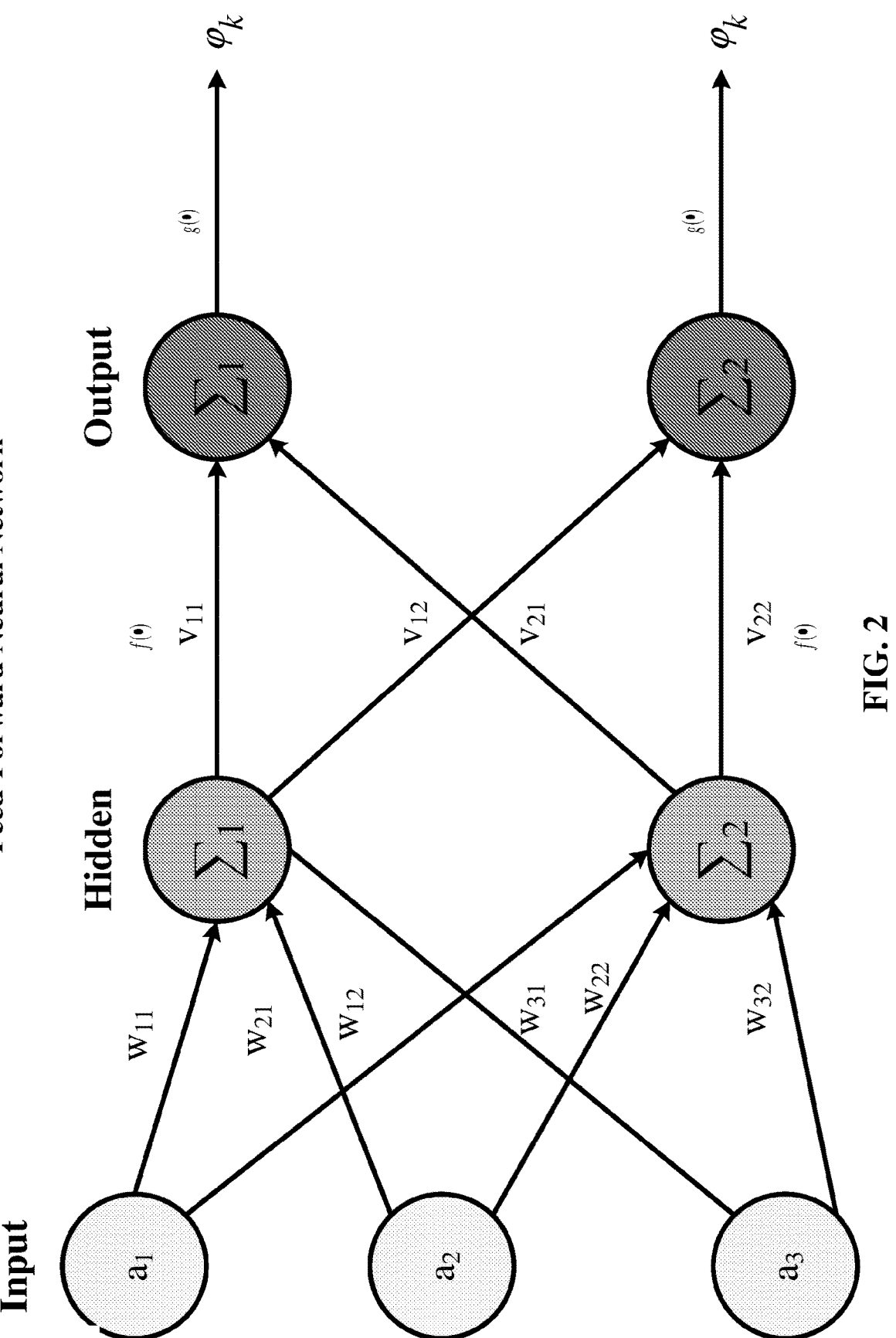
FIG. 2 shows one implementation of a feed-forward neural network with multiple layers.
Figure 3:
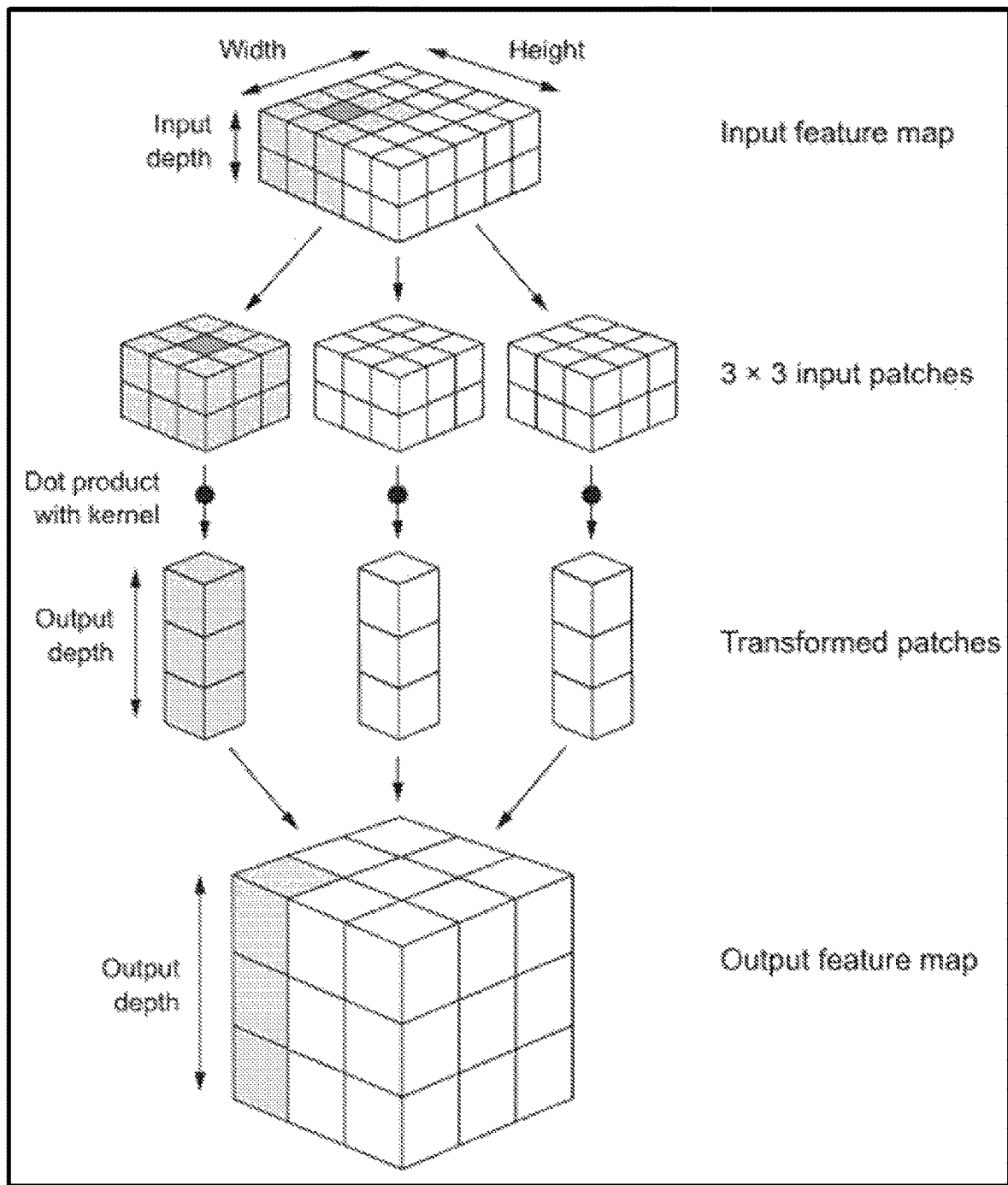
FIG. 3 depicts one implementation of workings of a convolutional neural network.
Figure 6:
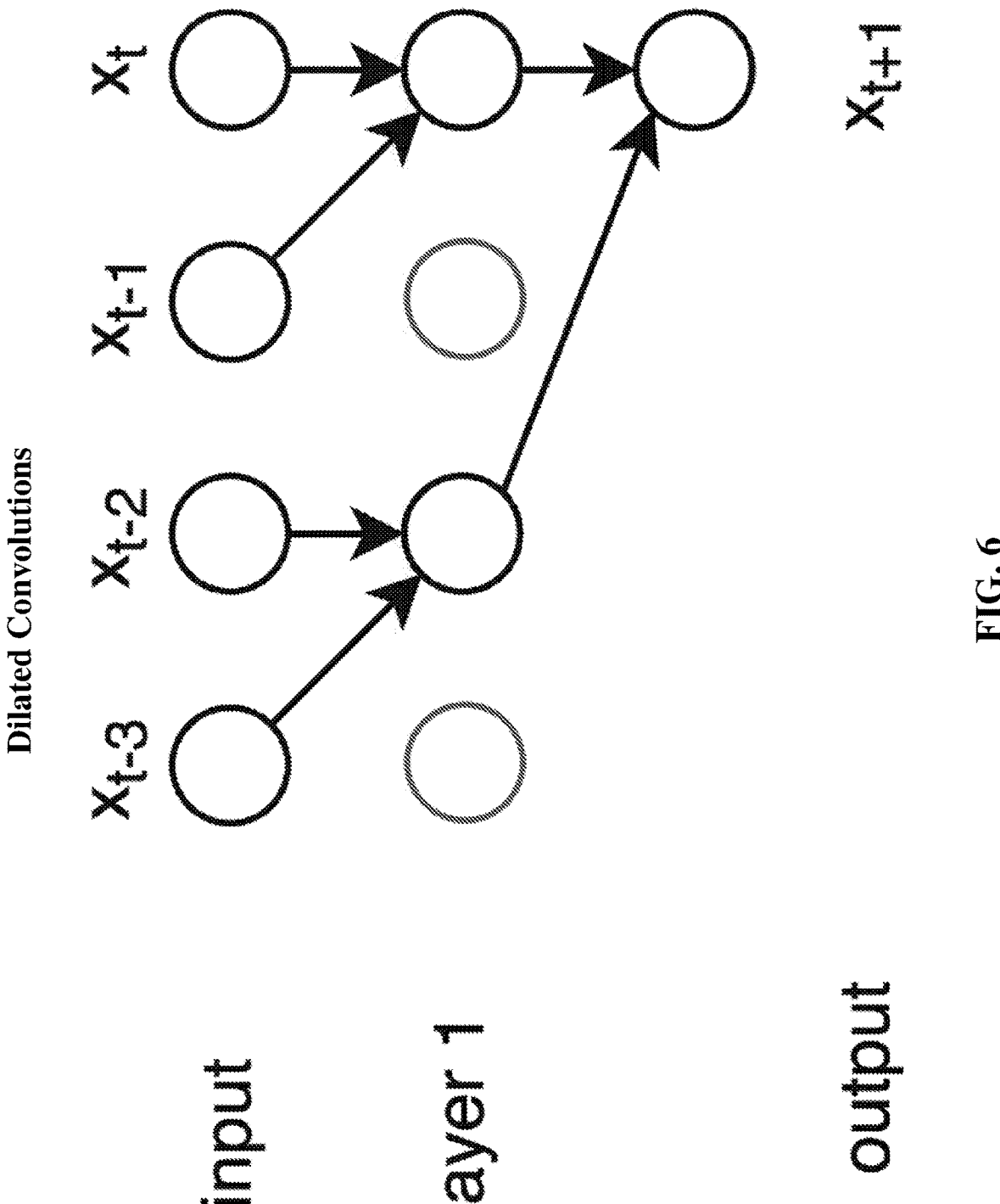
FIG. 6 illustrates dilated convolutions.
Figure 7:
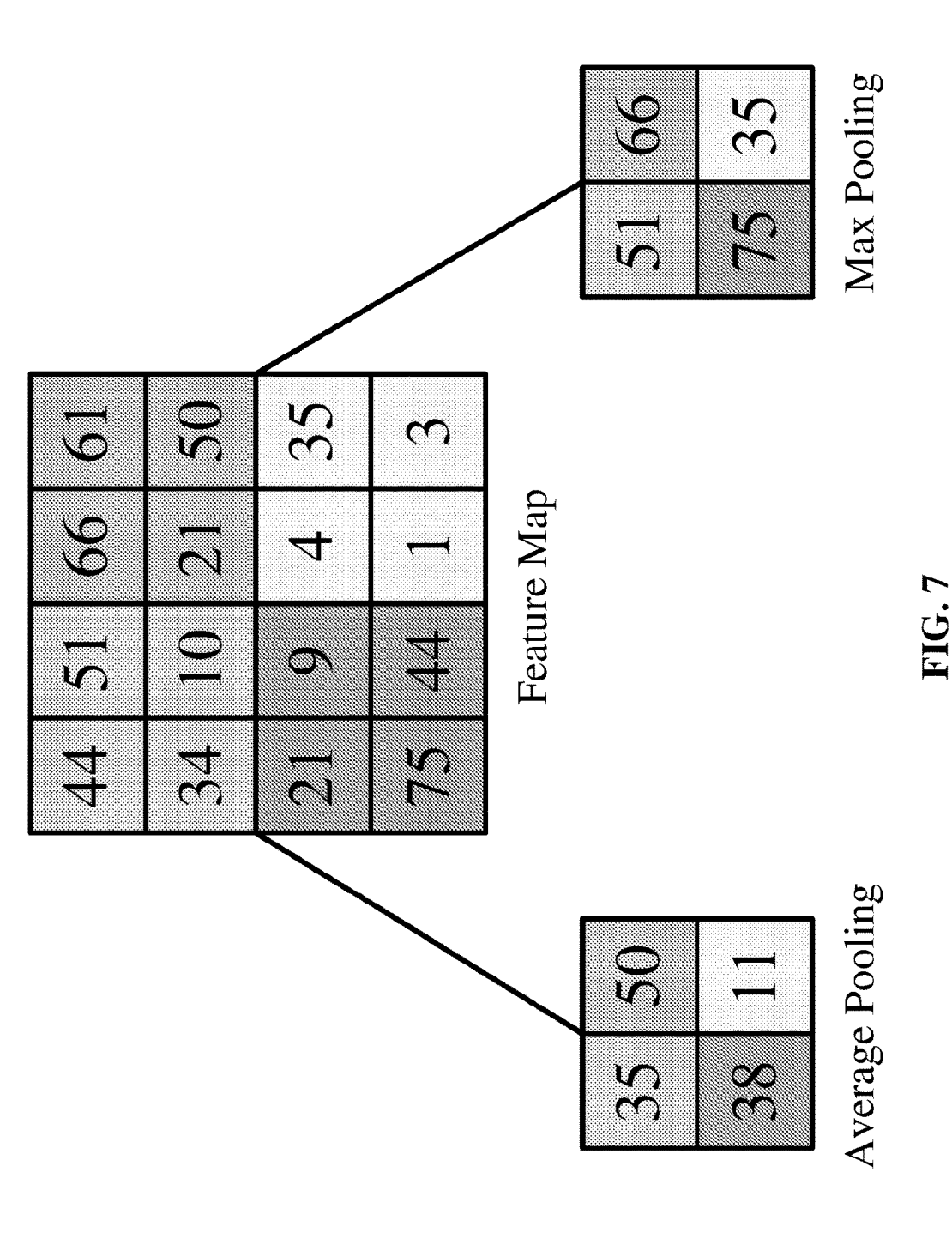
FIG. 7 is one implementation of sub-sampling layers (average/max pooling) in accordance with one implementation of the technology disclosed.
Figure 8:
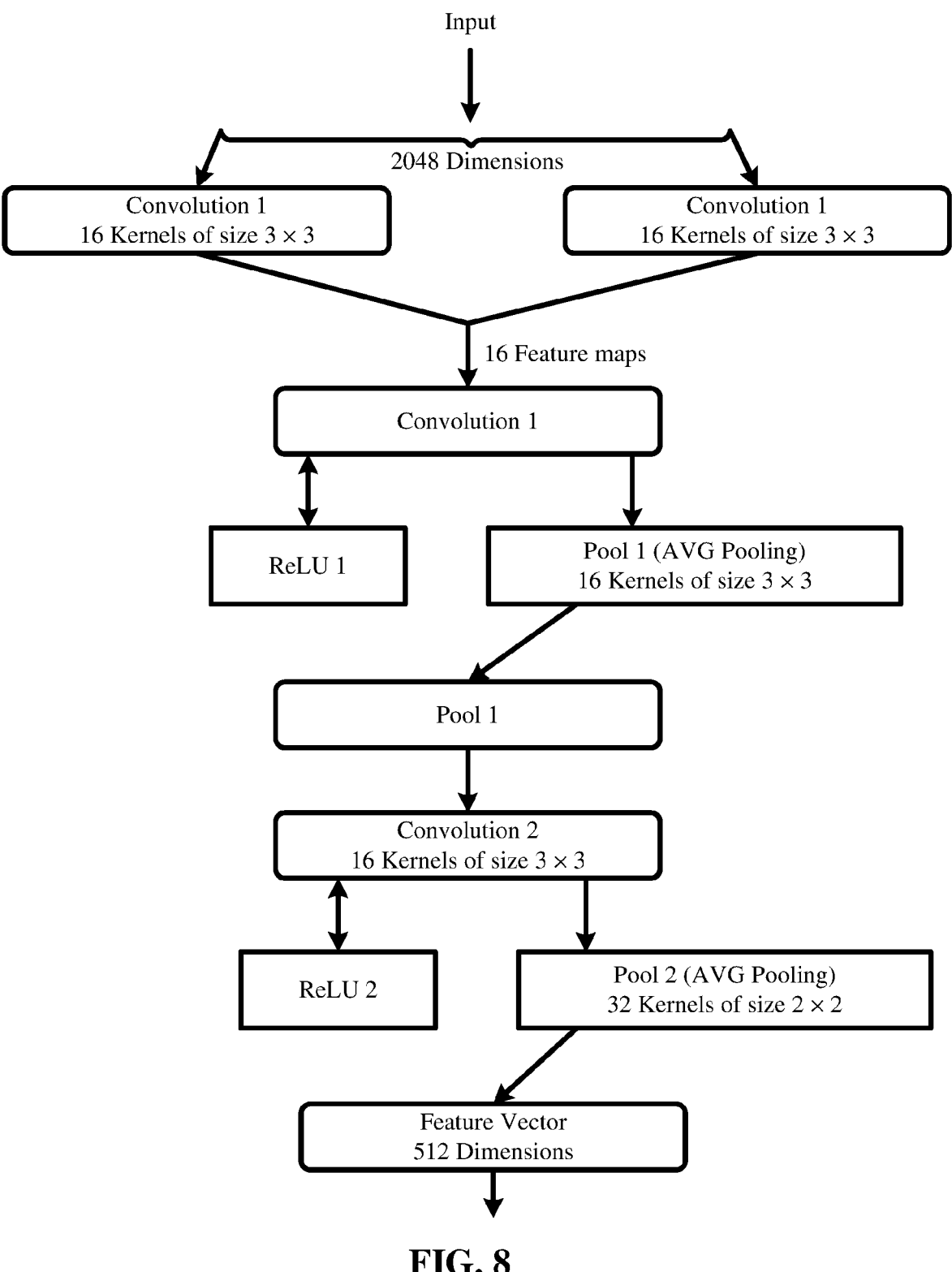
FIG. 8 depicts one implementation of a two-layer convolution of the convolution layers.
Figure 9:
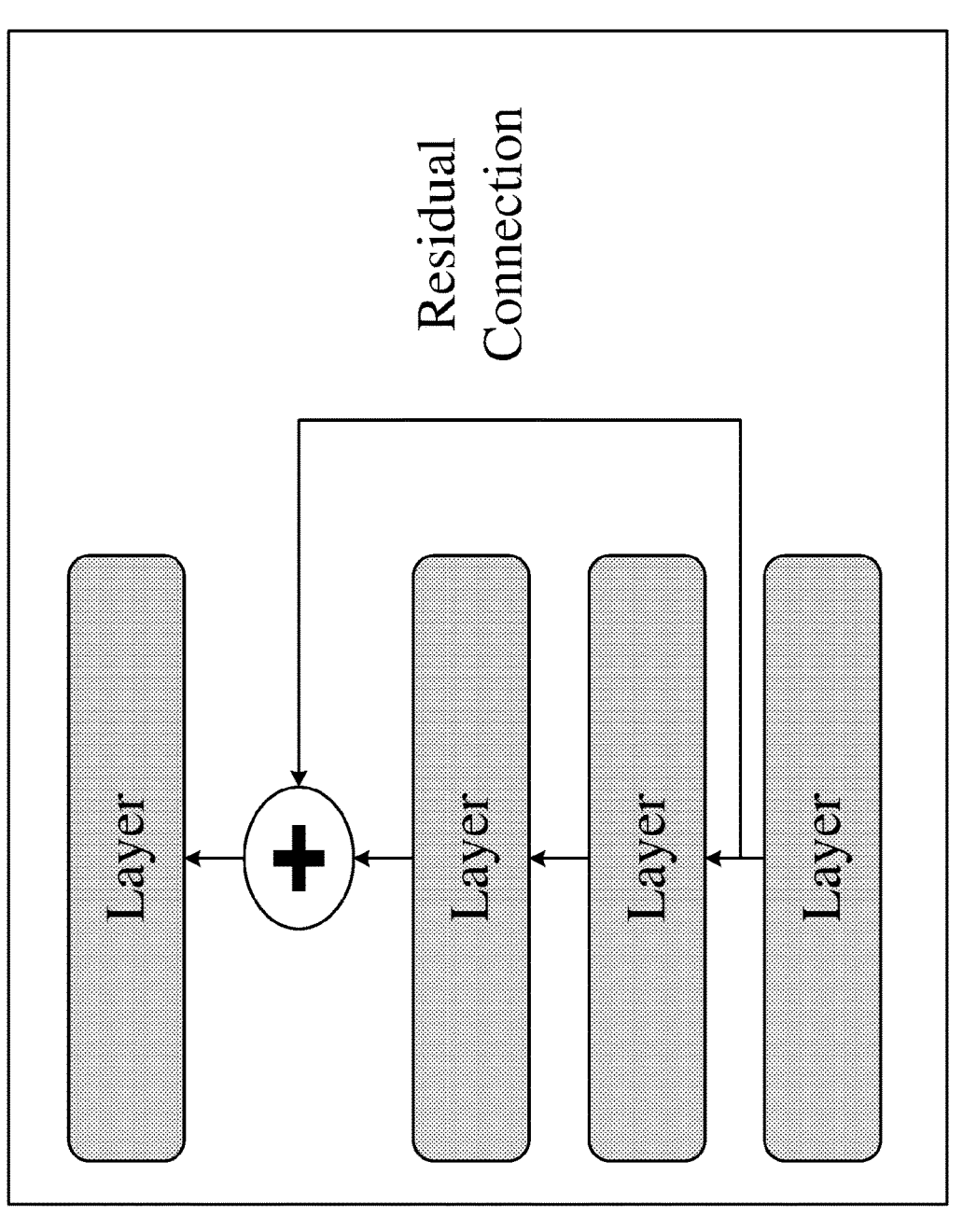
FIG. 9 depicts a residual connection that reinjects prior information downstream via feature-map addition.

FIG. 9 depicts a residual connection that reinjects prior information downstream via feature-map addition. A residual connection comprises reinjecting previous representations into the downstream flow of data by adding a past output tensor to a later output tensor, which helps prevent information loss along the data-processing flow. Residual connections tackle two common problems that plague any large-scale deep-learning model: vanishing gradients and representational bottlenecks. In general, adding residual connections to any model that has more than 10 layers is likely to be beneficial. As discussed above, a residual connection comprises making the output of an earlier layer available as input to a later layer, effectively creating a shortcut in a sequential network. Rather than being concatenated to the later activation, the earlier output is summed with the later activation, which assumes that both activations are the same size. If they are of different sizes, a linear transformation to reshape the earlier activation into the target shape can be used.

Residual Learning and Skip-Connections

Figure 10:
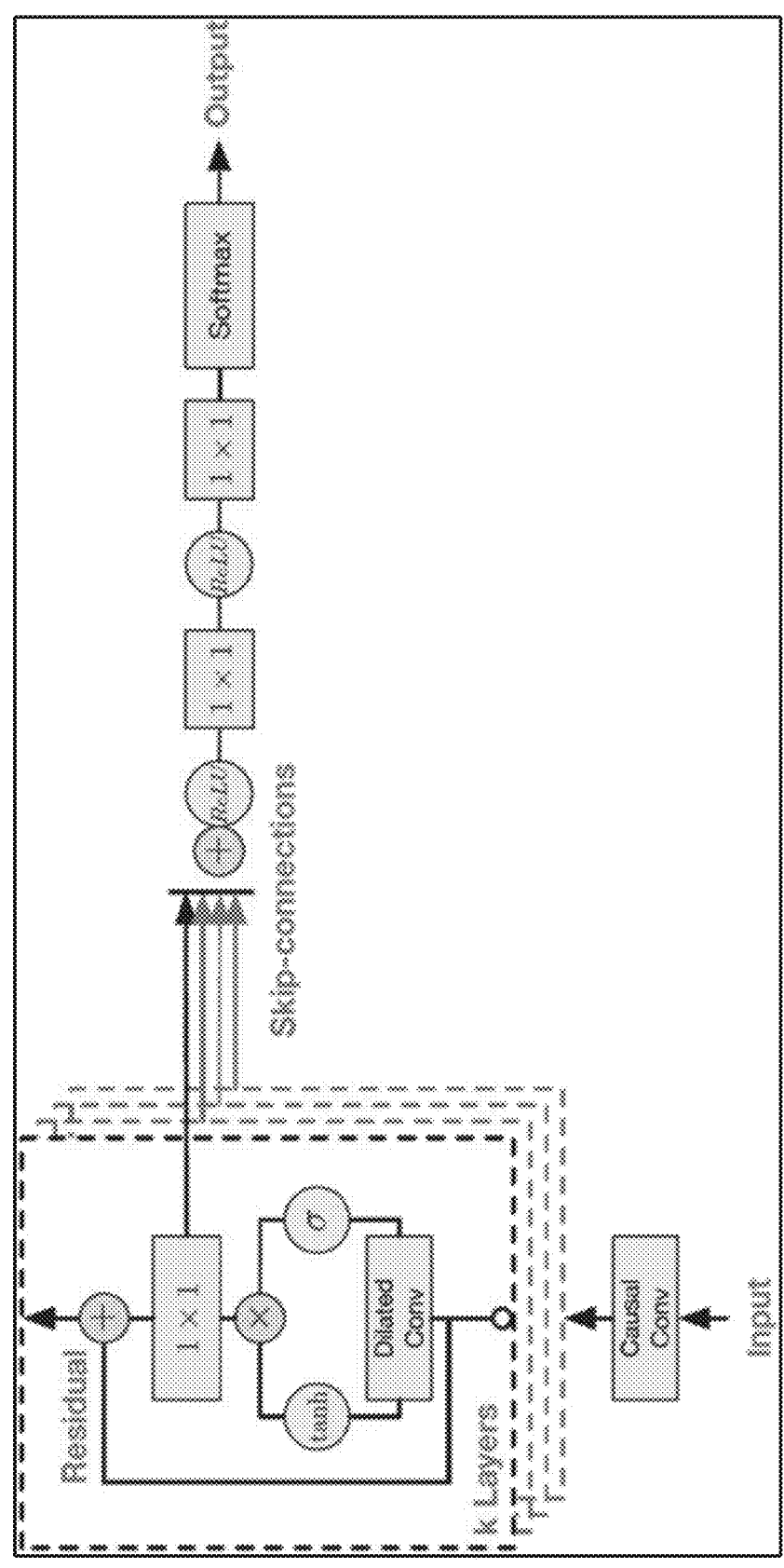
FIG. 10 depicts one implementation of residual blocks and skip-connections.

FIG. 10 depicts one implementation of residual blocks and skip-connections. The main idea of residual learning is that the residual mapping is much easier to be learned than the original mapping. Residual network stacks a number of residual units to alleviate the degradation of training accuracy. Residual blocks make use of special additive skip connections to combat vanishing gradients in deep neural networks. At the beginning of a residual block, the data flow is separated into two streams: the first carries the unchanged input of the block, while the second applies weights and non-linearities. At the end of the block, the two streams are merged using an element-wise sum. The main advantage of such constructs is to allow the gradient to flow through the network more easily.

Benefited from residual network, deep convolutional neural networks (CNNs) can be easily trained and improved accuracy has been achieved for image classification and object detection. Convolutional feed-forward networks connect the output of the $l^{th}$ layer as input to the $(l+1)^{th}$ layer, which gives rise to the following layer transition: $x_l=H_l(x_{l-1})$. Residual blocks add a skip-connection that bypasses the non-linear transformations with an identify function: $x_l=H_l(x_{l-1})+x_{l-1}$. An advantage of residual blocks is that the gradient can flow directly through the identity function from later layers to the earlier layers. However, the identity function and the output of $H_1$ are combined by summation, which may impede the information flow in the network.

WaveNet

The WaveNet is a deep neural network for generating raw audio waveforms. The WaveNet distinguishes itself from other convolutional networks since it is able to take relatively large 'visual fields' at low cost. Moreover, it is able to add conditioning of the signals locally and globally, which allows the WaveNet to be used as a text to speech (TTS) engine with multiple voices, is the TTS gives local conditioning and the particular voice the global conditioning.

Figure 11:
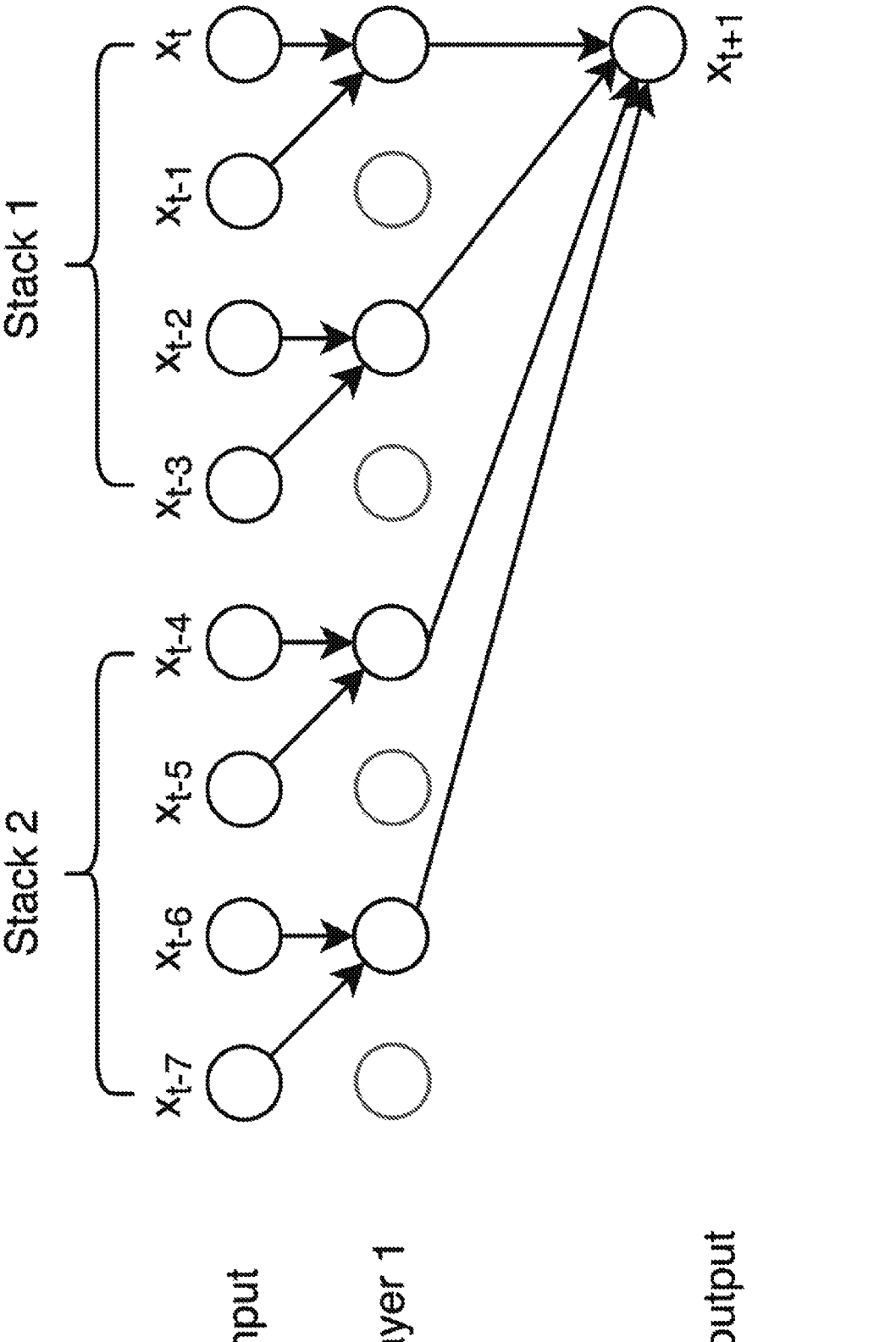
FIG. 11 shows one implementation of stacked dilated convolutions.

The main building blocks of the WaveNet are the causal dilated convolutions. As an extension on the causal dilated convolutions, the WaveNet also allows stacks of these convolutions, as shown in FIG. 11. To obtain the same receptive field with dilated convolutions in this figure, another dilation layer is required. The stacks are a repetition of the dilated convolutions, connecting the outputs of dilated convolution layer to a single output. This enables the WaveNet to get a large 'visual' field of one output node at a relatively low computational cost. For comparison, to get a visual field of 512 inputs, a fully convolutional network (FCN) would require 511 layers. In the case of a dilated convolutional network, we would need eight layers. The stacked dilated convolutions only need seven layers with two stacks or six layers with four stacks. To get an idea of the differences in computational power required for covering the same visual field, the following table shows the number of weights required in the network with the assumption of one filter per layer and a filter width of two. Furthermore, it is assumed that the network is using binary encoding of the 8 bits.

| Network type | No. stacks | No. weights per channel | Total No. of weights |
|---|---|---|---|
| FCN | 1 | $2.6 \cdot 10^5$ | $2.6 \cdot 10^6$ |
| WN | 1 | 1022 | 8176 |
| WN | 2 | 1022 | 8176 |
| WN | 4 | 508 | 4064 |

The WaveNet adds a skip connection before the residual connection is made, which bypasses all the following residual blocks. Each of these skip connections is summed before passing them through a series of activation functions and convolutions. Intuitively, this is the sum of the information extracted in each layer.

Batch Normalization

Batch normalization is a method for accelerating deep network training by making data standardization an integral part of the network architecture. Batch normalization can adaptively normalize data even as the mean and variance change over time during training. It works by internally maintaining an exponential moving average of the batchwise mean and variance of the data seen during training. The main effect of batch normalization is that it helps with gradient propagation—much like residual connections—and thus allows for deep networks. Some very deep networks can only be trained if they include multiple Batch Normalization layers.

Batch normalization can be seen as yet another layer that can be inserted into the model architecture, just like the fully connected or convolutional layer. The BatchNormalization layer is typically used after a convolutional or densely connected layer. It can also be used before a convolutional or densely connected layer. Both implementations can be used by the technology disclosed and are shown in FIG. 15. The BatchNormalization layer takes an axis argument, which specifies the feature axis that should be normalized.

This argument defaults to −1, the last axis in the input tensor. This is the correct value when using Dense layers, Conv1D layers, RNN layers, and Conv2D layers with data format set to "channels_last". But in the niche use case of Conv2D layers with data format set to "channels_first", the features axis is axis 1; the axis argument in BatchNormalization can be set to 1.

Batch normalization provides a definition for feed-forwarding the input and computing the gradients with respect to the parameters and its own input via a backward pass. In practice, batch normalization layers are inserted after a convolutional or fully connected layer, but before the outputs are fed into an activation function. For convolutional layers, the different elements of the same feature map—i.e. the activations—at different locations are normalized in the same way in order to obey the convolutional property. Thus, all activations in a mini-batch are normalized over all locations, rather than per activation.

The internal covariate shift is the major reason why deep architectures have been notoriously slow to train. This stems from the fact that deep networks do not only have to learn a new representation at each layer, but also have to account for the change in their distribution.

The covariate shift in general is a known problem in the deep learning domain and frequently occurs in real-world problems. A common covariate shift problem is the difference in the distribution of the training and test set which can lead to suboptimal generalization performance. This problem is usually handled with a standardization or whitening preprocessing step. However, especially the whitening operation is computationally expensive and thus impractical in an online setting, especially if the covariate shift occurs throughout different layers.

The internal covariate shift is the phenomenon where the distribution of network activations change across layers due to the change in network parameters during training. Ideally, each layer should be transformed into a space where they have the same distribution but the functional relationship stays the same. In order to avoid costly calculations of covariance matrices to decorrelate and whiten the data at every layer and step, we normalize the distribution of each input feature in each layer across each mini-batch to have zero mean and a standard deviation of one.

Forward Pass

During the forward pass, the mini-batch mean and variance are calculated. With these mini-batch statistics, the data is normalized by subtracting the mean and dividing by the standard deviation. Finally, the data is scaled and shifted with the learned scale and shift parameters. The batch normalization forward pass $f_{BN}$ is depicted in FIG. 12.

In FIG. 12, $\mu_\beta$ is the batch mean and $\sigma_\beta^2$ is the batch variance, respectively. The learned scale and shift parameters are denoted by $\gamma$ and $\beta$, respectively. For clarity, the batch normalization procedure is described herein per activation and omit the corresponding indices.

Since normalization is a differentiable transform, the errors are propagated into these learned parameters and are thus able to restore the representational power of the network by learning the identity transform. Conversely, by learning scale and shift parameters that are identical to the corresponding batch statistics, the batch normalization transform would have no effect on the network, if that was the optimal operation to perform. At test time, the batch mean and variance are replaced by the respective population statistics since the input does not depend on other samples from a mini-batch. Another method is to keep running averages of the batch statistics during training and to use these to compute the network output at test time. At test time, the batch normalization transform can be expressed as illustrated in FIG. 13. In FIG. 13, $\mu_D$ and $$\sigma_D^2$$

denote the population mean and variance, rather than the batch statistics, respectively.

Backward Pass

Since normalization is a differentiable operation, the backward pass can be computed as depicted in FIG. 14.

Figure 16:
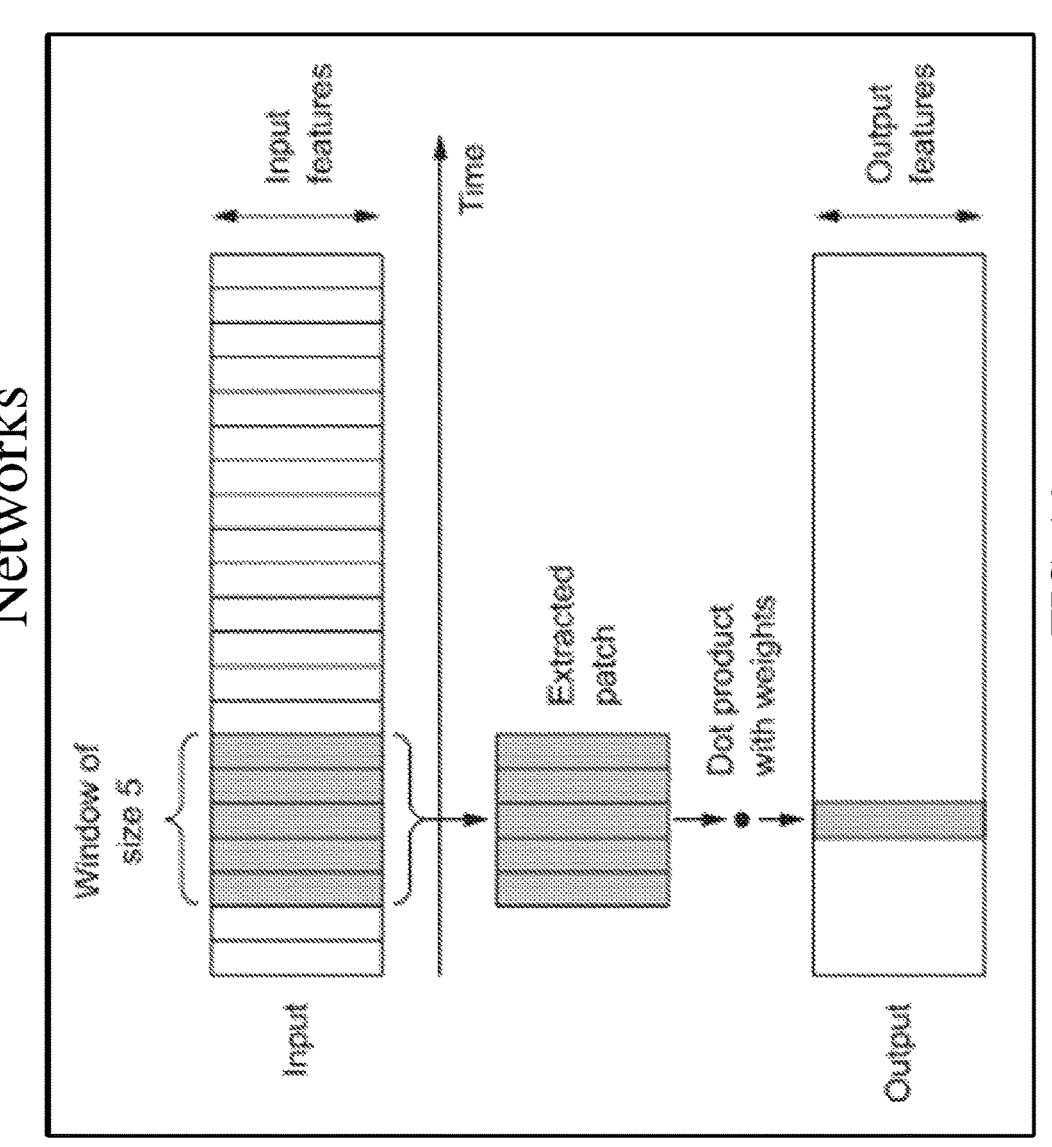
FIG. 16 shows one implementation of 1D convolution.

1D Convolution 1D convolutions extract local 1D patches or subsequences from sequences, as shown in FIG. 16. 1D convolution obtains each output timestep from a temporal patch in the input sequence. 1D convolution layers recognize local patterns in a sequence. Because the same input transformation is performed on every patch, a pattern learned at a certain position in the input sequences can be later recognized at a different position, making 1D convolution layers translation invariant for temporal translations. For instance, a 1D convolution layer processing sequences of bases using convolution windows of size 5 should be able to learn bases or base sequences of length 5 or less, and it should be able to recognize the base motifs in any context in an input sequence. A base-level 1D convolution is thus able to learn about base morphology.

Global Average Pooling

Figure 17:
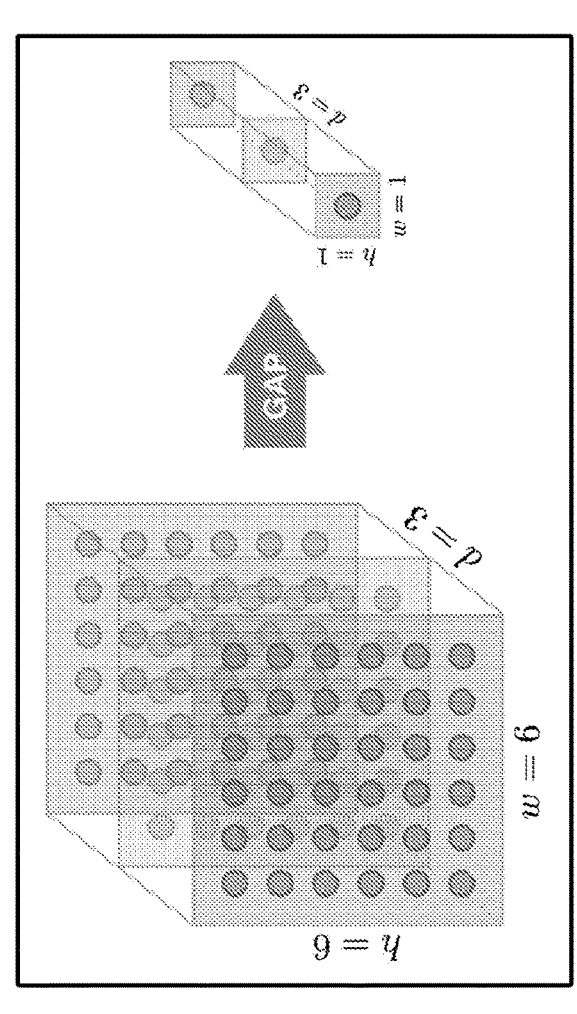
FIG. 17 illustrates how global average pooling (GAP) works.
Figure 17:
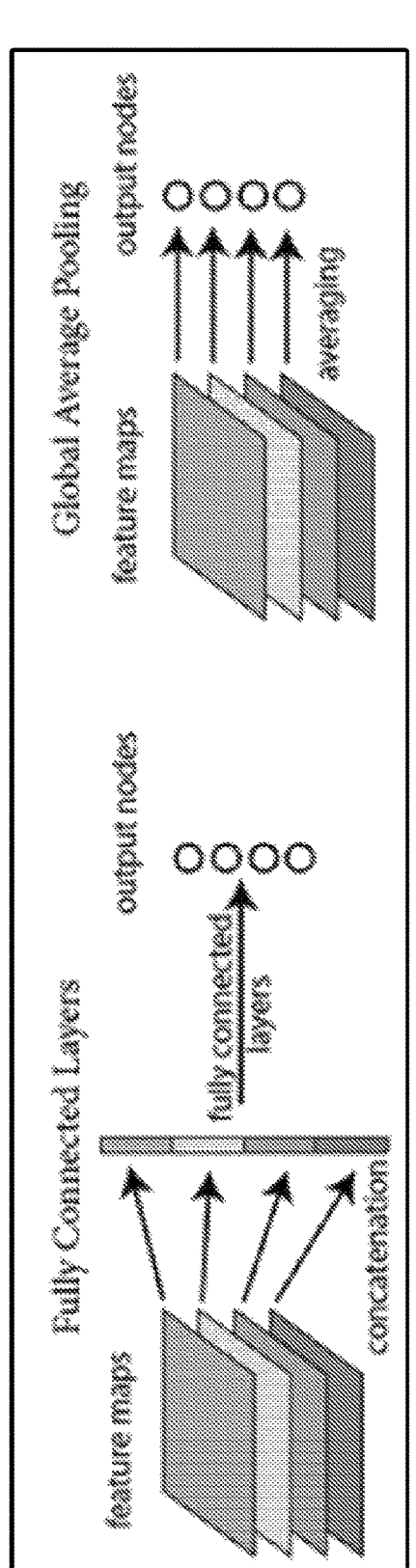

FIG. 17 illustrates how global average pooling (GAP) works. Global average pooling can be use used to replace fully connected (FC) layers for classification, by taking the spatial average of features in the last layer for scoring. The reduces the training load and bypasses overfitting issues. Global average pooling applies a structural prior to the model and it is equivalent to linear transformation with predefined weights. Global average pooling reduces the number of parameters and eliminates the fully connected layer. Fully connected layers are typically the most parameter and connection intensive layers, and global average pooling provides much lower-cost approach to achieve similar results. The main idea of global average pooling is to generate the average value from each last layer feature map as the confidence factor for scoring, feeding directly into the softmax layer.

Global average pooling have three benefits: (1) there are no extra parameters in global average pooling layers thus overfitting is avoided at global average pooling layers; (2) since the output of global average pooling is the average of the whole feature map, global average pooling will be more robust to spatial translations; and (3) because of the huge number of parameters in fully connected layers which usually take over 50% in all the parameters of the whole network, replacing them by global average pooling layers can significantly reduce the size of the model, and this makes global average pooling very useful in model compression.

Global average pooling makes sense, since stronger features in the last layer are expected to have a higher average value. In some implementations, global average pooling can be used as a proxy for the classification score. The feature maps under global average pooling can be interpreted as confidence maps, and force correspondence between feature maps and the categories. Global average pooling can be particularly effective if the last layer features are at a sufficient abstraction for direct classification; however, global average pooling alone is not enough if multilevel features should be combined into groups like parts models, which is best performed by adding a simple fully connected layer or other classifier after the global average pooling.

Deep Learning in Genomics

Genetic variations can help explain many diseases. Every human being has a unique genetic code and there are lots of genetic variants within a group of individuals. Most of the deleterious genetic variants have been depleted from genomes by natural selection. It is important to identify which genetics variations are likely to be pathogenic or deleterious. This will help researchers focus on the likely pathogenic genetic variants and accelerate the pace of diagnosis and cure of many diseases.

Modeling the properties and functional effects (e.g., pathogenicity) of variants is an important but challenging task in the field of genomics. Despite the rapid advancement of functional genomic sequencing technologies, interpretation of the functional consequences of variants remains a great challenge due to the complexity of cell type-specific transcription regulation systems.

Regarding pathogenicity classifiers, deep neural networks are a type of artificial neural networks that use multiple nonlinear and complex transforming layers to successively model high-level features. Deep neural networks provide feedback via backpropagation which carries the difference between observed and predicted output to adjust parameters. Deep neural networks have evolved with the availability of large training datasets, the power of parallel and distributed computing, and sophisticated training algorithms. Deep neural networks have facilitated major advances in numerous domains such as computer vision, speech recognition, and natural language processing.

Convolutional neural networks (CNNs) and recurrent neural networks (RNNs) are components of deep neural networks. Convolutional neural networks have succeeded particularly in image recognition with an architecture that comprises convolution layers, nonlinear layers, and pooling layers. Recurrent neural networks are designed to utilize sequential information of input data with cyclic connections among building blocks like perceptrons, long short-term memory units, and gated recurrent units. In addition, many other emergent deep neural networks have been proposed for limited contexts, such as deep spatio-temporal neural networks, multi-dimensional recurrent neural networks, and convolutional auto-encoders.

The goal of training deep neural networks is optimization of the weight parameters in each layer, which gradually combines simpler features into complex features so that the most suitable hierarchical representations can be learned from data. A single cycle of the optimization process is organized as follows. First, given a training dataset, the forward pass sequentially computes the output in each layer and propagates the function signals forward through the network. In the final output layer, an objective loss function measures error between the inferenced outputs and the given labels. To minimize the training error, the backward pass uses the chain rule to backpropagate error signals and compute gradients with respect to all weights throughout the neural network. Finally, the weight parameters are updated using optimization algorithms based on stochastic gradient descent. Whereas batch gradient descent performs parameter updates for each complete dataset, stochastic gradient descent provides stochastic approximations by performing the updates for each small set of data examples. Several optimization algorithms stem from stochastic gradient descent. For example, the Adagrad and Adam training algorithms perform stochastic gradient descent while adaptively modifying learning rates based on update frequency and moments of the gradients for each parameter, respectively.

Another core element in the training of deep neural networks is regularization, which refers to strategies intended to avoid overfitting and thus achieve good generalization performance. For example, weight decay adds a penalty term to the objective loss function so that weight parameters converge to smaller absolute values. Dropout randomly removes hidden units from neural networks during training and can be considered an ensemble of possible subnetworks. To enhance the capabilities of dropout, a new activation function, maxout, and a variant of dropout for recurrent neural networks called rnnDrop have been proposed. Furthermore, batch normalization provides a new regularization method through normalization of scalar features for each activation within a mini-batch and learning each mean and variance as parameters.

Given that sequenced data are multi- and high-dimensional, deep neural networks have great promise for bioinformatics research because of their broad applicability and enhanced prediction power. Convolutional neural networks have been adapted to solve sequence-based problems in genomics such as motif discovery, pathogenic variant identification, and gene expression inference. Convolutional neural networks use a weight-sharing strategy that is especially useful for studying DNA because it can capture sequence motifs, which are short, recurring local patterns in DNA that are presumed to have significant biological functions. A hallmark of convolutional neural networks is the use of convolution filters. Unlike traditional classification approaches that are based on elaborately-designed and manually-crafted features, convolution filters perform adaptive learning of features, analogous to a process of mapping raw input data to the informative representation of knowledge. In this sense, the convolution filters serve as a series of motif scanners, since a set of such filters is capable of recognizing relevant patterns in the input and updating themselves during the training procedure. Recurrent neural networks can capture long-range dependencies in sequential data of varying lengths, such as protein or DNA sequences.

Therefore, a powerful computational model for predicting the pathogenicity of variants can have enormous benefits for both basic science and translational research.

Particular Implementations

We describe systems, methods, and articles of manufacture for artificial intelligence-based epigenetics. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

In one implementation, the sequence-to-sequence epigenetic model and/or the pathogenicity determiner is a convolutional neural network. In another implementation, the sequence-to-sequence epigenetic model and/or the pathogenicity determiner is a recurrent neural network. In yet another implementation, the sequence-to-sequence epigenetic model and/or the pathogenicity determiner is a residual neural network with residual bocks and residual connections. In a further implementation, the sequence-to-sequence epigenetic model and/or the pathogenicity determiner is a combination of a convolutional neural network and a recurrent neural network.

One skilled in the art will appreciate that the sequence-to-sequence epigenetic model and/or the pathogenicity determiner can use various padding and striding configurations. It can use different output functions (e.g., classification or regression) and may or may not include one or more fully-connected layers. It can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous SGD. It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tan h)), batch normalization layers, regularization layers, dropout, pooling layers (e.g., max or average pooling), global average pooling layers, and attention mechanisms.

Promoter Sequence

Figure 25B:
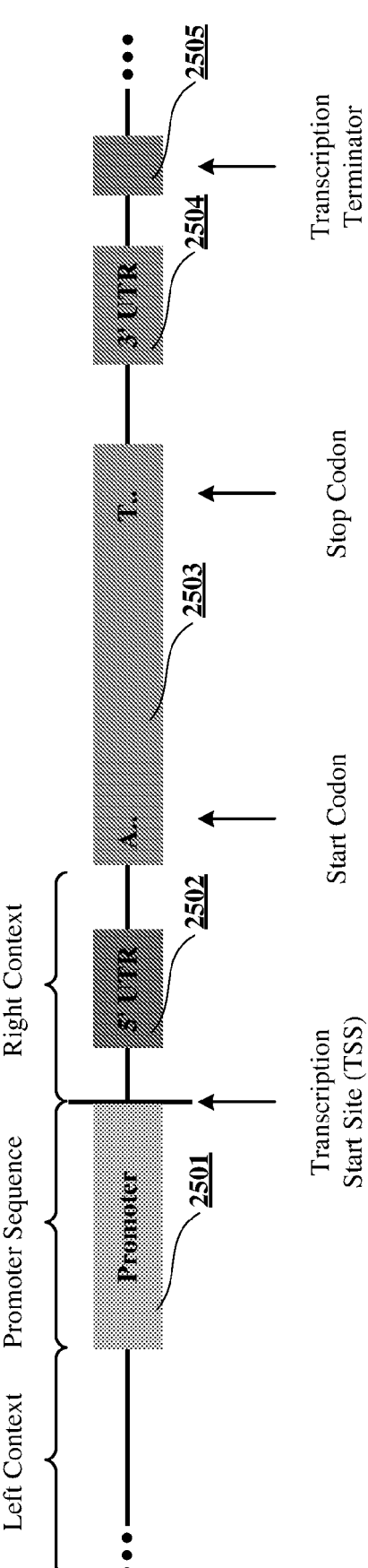
FIG. 25B shows an example promoter sequence of a gene.

FIG. 25B shows an example promoter sequence 2501 of a gene. The input to the pathogenicity classifiers are promoter sequences, which are regulatory regions located upstream (towards the 5' region) of the gene, adjacent to the transcription start site (TSS). They do not code for proteins and instead provide an initiation and control point for regulated gene transcription.

In one implementation, the length of the promoter sequences is 3001 bases. In other implementations, the length can be decreased or increased, for instance from 200 to 20,000 bases, or it can be adapted to specific promoter regions (e.g., be centered at the TSS). The promoter sequences are flanked by right and left context that extends outside the promoter region, including into the gene sequence that follows the promoter region (e.g., 5' UTR regions 2502, start and stop codons 2503, 3' UTR regions 2504, transcription terminator 2505). The flanking context can be 100 to 5000 bases. Typically, the upstream and downstream flanking contexts are equal, but that is not essential.

The promoter sequences contain reference bases from one or more reference genome databases. The reference bases are one-hot encoded to conserve the position-specific information of each individual base in the promoter sequences. In one-hot encoding, each reference base is encoded with a binary vector of four bits, with one of the bits being hot (i.e., 1) while others being off (i.e., 0). For instance, as shown in FIG. 25, T=(1, 0, 0, 0), G=(0, 1, 0, 0), C=(0, 0, 1, 0), and A=(0, 0, 0, 1). In some implementations, an undetermined base is encoded as N=(0, 0, 0, 0). FIG. 25B shows an example promoter sequence (in yellow) with reference bases represented using one-hot encoding. When the pathogenicity classifiers, as convolutional neural networks, receive the one-hot encoded reference bases, they are able to preserve the spatial locality relationships within the promoter sequences.

Sequence-to-Sequence Epigenetic Model

Figure 26:
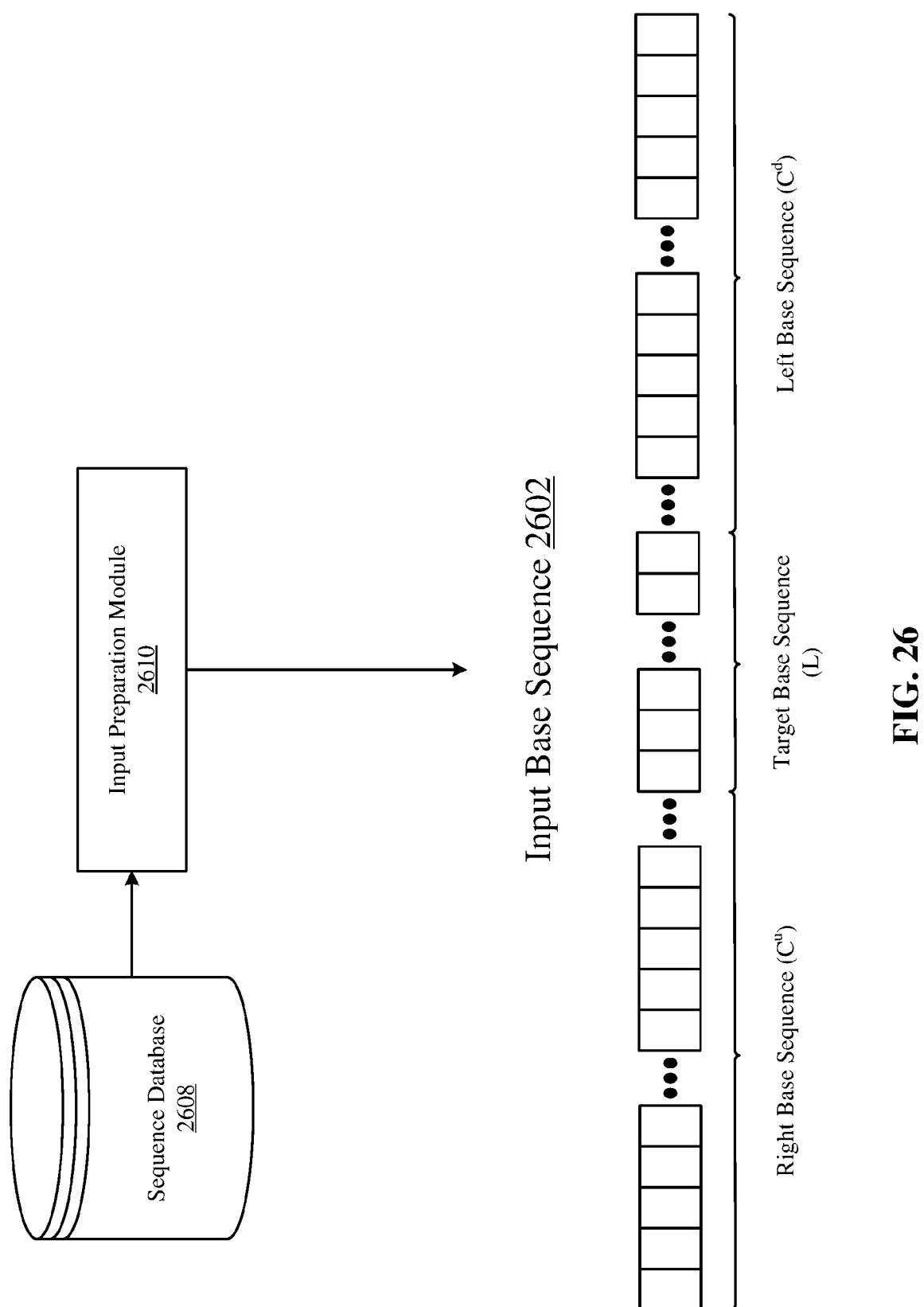
FIG. 26 shows an input preparation module that accesses a sequence database and generates an input base sequence.

FIG. 26 shows an input preparation module 2610 that accesses a sequence database 2608 and generates an input base sequence 2602. The input base sequence 2602 comprises (i) a target base sequence with target bases. The target base sequence is flanked by (ii) a right base sequence with downstream context bases, and (iii) a left base sequence with upstream context bases. In some implementations, the target base sequence is the promoter sequence 2501.

Figure 27:
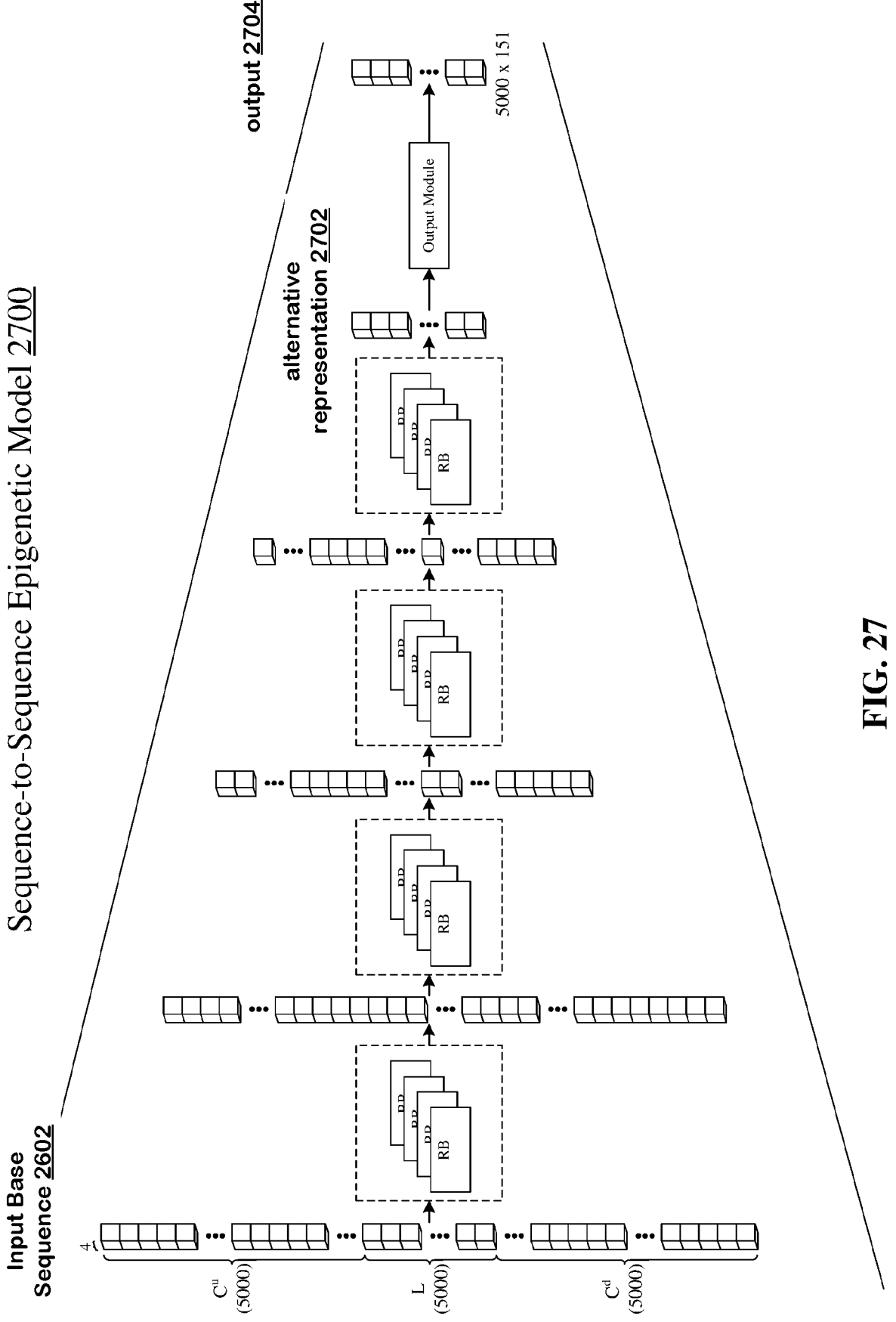
FIG. 27 shows an example of a sequence-to-sequence epigenetic model.

FIG. 27 shows an example of a sequence-to-sequence epigenetic model 2700.

The sequence-to-sequence model 2700 processes the input base sequence 2602 and generates an alternative representation 2702 of the input base sequence 2602. An output module processes the alternative representation 2702 of the input base sequence 2602 and produces an output 2704 that has at least one per-base output for each of the target bases in the target base sequence, wherein the per-base output specifies, for a corresponding target base, signal levels of a plurality of epigenetic tracks. Details of the sequence-to-sequence model 2700 are described in FIGS. 19, 20, 21, 22, 23, and 24.

Epigenetic Tracks and their Signal Levels

The plurality of epigenetic tracks includes deoxyribonucleic acid (DNA) methylation changes (e.g., CpG), histone modifications, noncoding ribonucleic acid (ncRNA) expression, and chromatin structural changes (e.g., nucleosome positioning). The plurality of epigenetic tracks includes deoxyribonuclease (DNase) tracks. The plurality of epigenetic tracks includes histone 3 lysine 27 acetylation (H3K27ac) tracks. A combination of these epigenetic tracks across different tissues, cell types, and cell lines produces over a thousand different epigenetic tracks and our sequence-to-sequence model 2700 can produce an output that specifies signals levels for each of a thousand epigenetic tracks for each base in the input base sequence.

In one implementation, our sequence-to-sequence model 2700 produces an output that specifies signals levels for each one of 151 epigenetic tracks for each base in the input base sequence. These 151 epigenetic tracks are produced as cell type and cell line combination of the following epigenetic signals: GM12878 Roadmap tracks (DNase, H2A.Z, H3K27ac, H3K27me3, H3K36me3, H3K4me1, H3K4me2, H3K4me3, H3K79me2, H3K9ac, H3K9me3, H4K20me1).

For training purposes, ground truth signal levels of epigenetic tracks are obtained from sources like the Roadmap Epigenomics Project (https://egg2.wustl.edu/roadmap/webportal/index.html) and/or the ENCODE (https://www.encodeproject.org/). In one implementation, the epigenetic tracks are Genome-wide signal coverage tracks found here https://egg2.wustl.edu/roadmap/webportal/processed data.html#ChipSeq_DNaseSeq, which is incorporated by reference herein. In some implementations, the epigenetic tracks are −log 10(p-value) signal tracks found here https://egg2.wustl.edu/roadmap/data/byFileType/signal/consolidated/macs2signal/pval/, which is incorporated by reference herein. In other implementations, the epigenetic tracks are Fold-enrichment signal tracks found here https://egg2.wustl.edu/roadmap/data/byFileType/signal/consolidated/macs2signal/foldChange/, which is incorporated by reference herein.

In one implementation, we used the signal processing engine of the MACSv2.0.10 peak caller to generate genome-wide signal coverage tracks (https://github.com/taoliu/MACS/, incorporated by reference herein). Whole cell extract was used as a control for signal normalization for the histone ChIP-seq coverage. Each DNase-seq dataset was normalized using simulated background datasets generated by uniformly distributing equivalent number of reads across the mappable genome.

In one implementation, we generated two types of tracks that use different statistics based on a Poisson background model to represent per-base signal scores. Briefly, reads are extended in the 5' to 3' direction by the estimated fragment length. At each base, the observed counts of ChIP-seq/DNaseI-seq extended reads overlapping the base are compared to corresponding dynamic expected background counts (local) estimated from the control dataset. local is defined as max(BG, 1K, 5K, 10K) where BG is the expected counts per base assuming a uniform distribution of control reads across all mappable bases in the genome and 1K, 5K, 10K are expected counts estimated from the 1 kb, 5 kb and 10 kb window centered at the base. local is adjusted for the ratio of the sequencing depth of ChIP-seq/DNase-seq dataset relative to the control dataset. The two types of signal score statistics computed per base are as follows.

(1) Fold-enrichment ratio of ChIP-seq or DNase counts relative to expected background counts local. These scores provide a direct measure of the effect size of enrichment at any base in the genome.

(2) Negative log 10 of the Poisson p-value of ChIP-seq or DNase counts relative to expected background counts local. These signal confidence scores provide a measure of statistical significance of the observed enrichment.

Additional information about the how signal levels such as p-values, fold enrichment values, etc. are measured using ChIP-seq or DNase and peak calling can be found in Appendix B, which is bodily incorporated in the Priority Provisional Application No. 62/903,700.

Per-Track Processors

Figure 28:
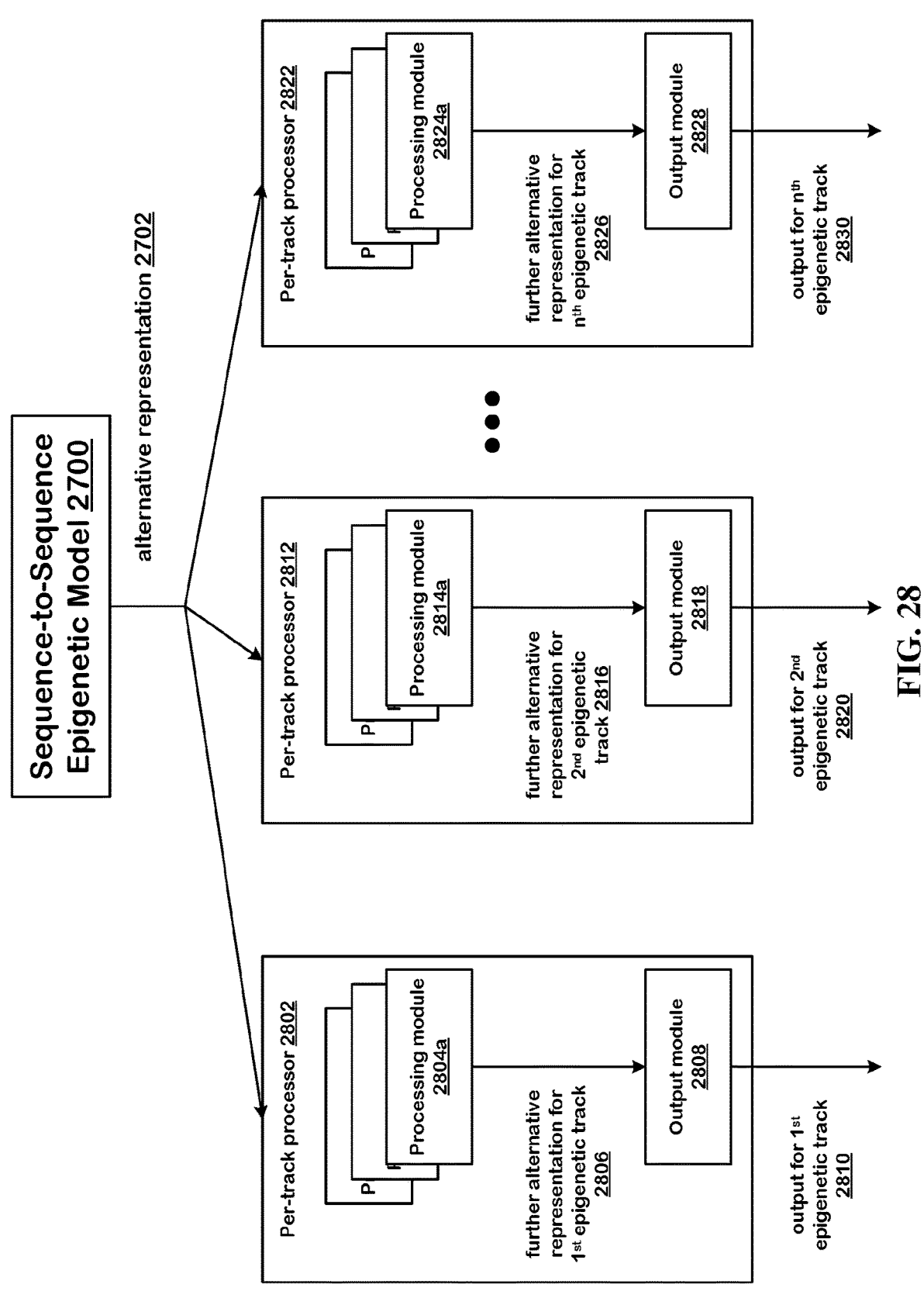
FIG. 28 shows per-track processors of the sequence-to-sequence model.

FIG. 28 shows per-track processors of the sequence-to-sequence model 2700. In one implementation, the sequence-to-sequence model 2700 has a plurality of per-track processors 2802, 2812, and 2822 corresponding to a respective epigenetic track in a plurality of epigenetic tracks. Each per-track processor further comprises at least one processing module 2804a, 2814a, and 2824a (e.g., multiple residual blocks in each per-track processor) and an output module 2808, 2818, and 2828 (e.g., a linear module, a rectified linear unit (ReLU) module). The sequence-to-sequence model processes an input base sequence and generates an alternative representation 2702 of the input base sequence. Each per-track processor's processing module processes the alternative representation and generates a further alternative representation 2806, 2816, and 2826 that is specific to a particular per-track processor. Each per-track processor's output module processes the further alternative representation generated by its corresponding processing module and produces, as output 2810, 2820, and 2830, a signal level for a corresponding epigenetic track and for each base in the input base sequence.

Position-Wise Comparison

Figure 29:
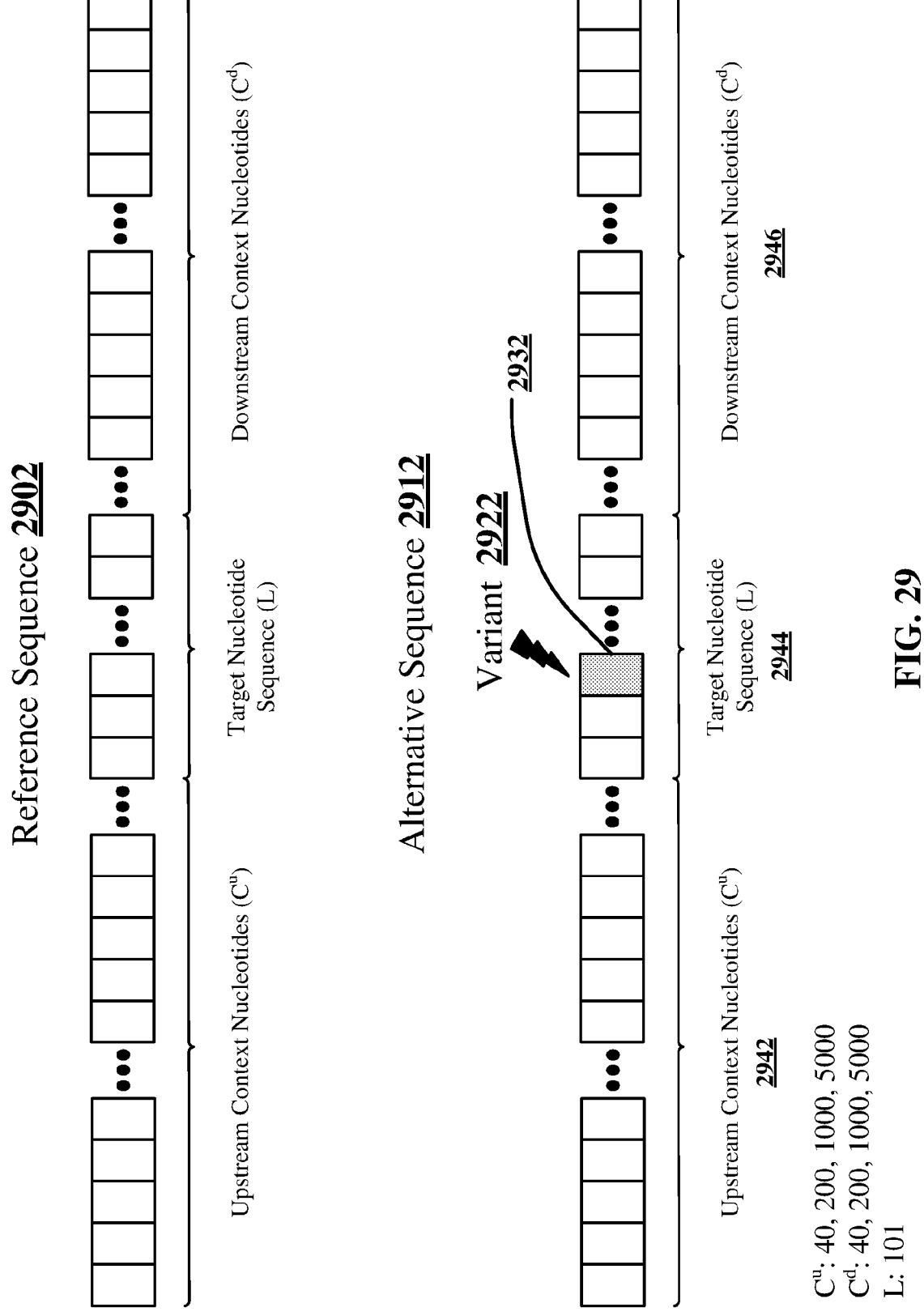
FIG. 29 depicts a reference sequence and an alternative sequence.
Figure 30:
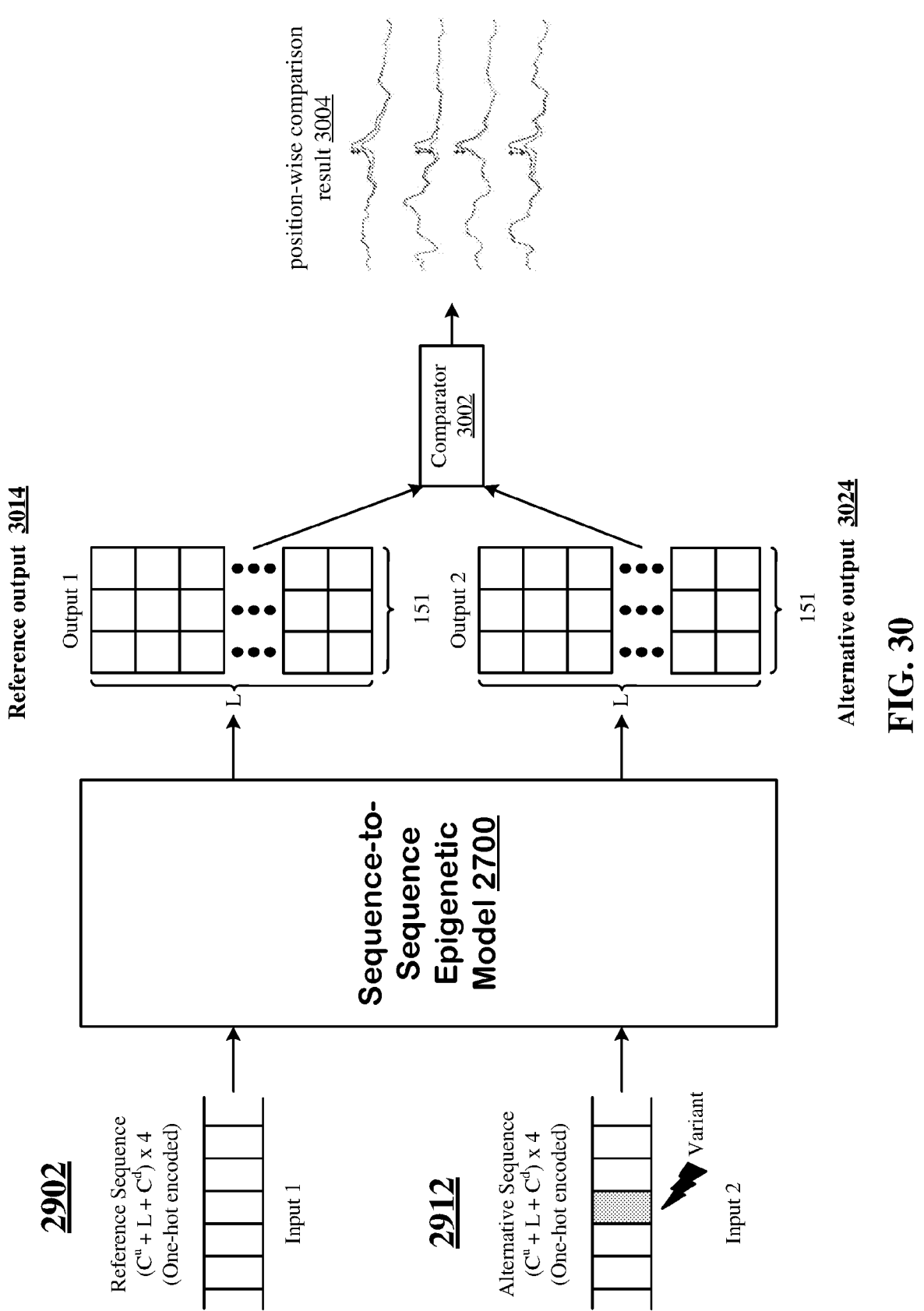
FIG. 30 illustrates one implementation of generating a position-wise comparison result using the sequence-to-sequence model 2700.
Figure 31:
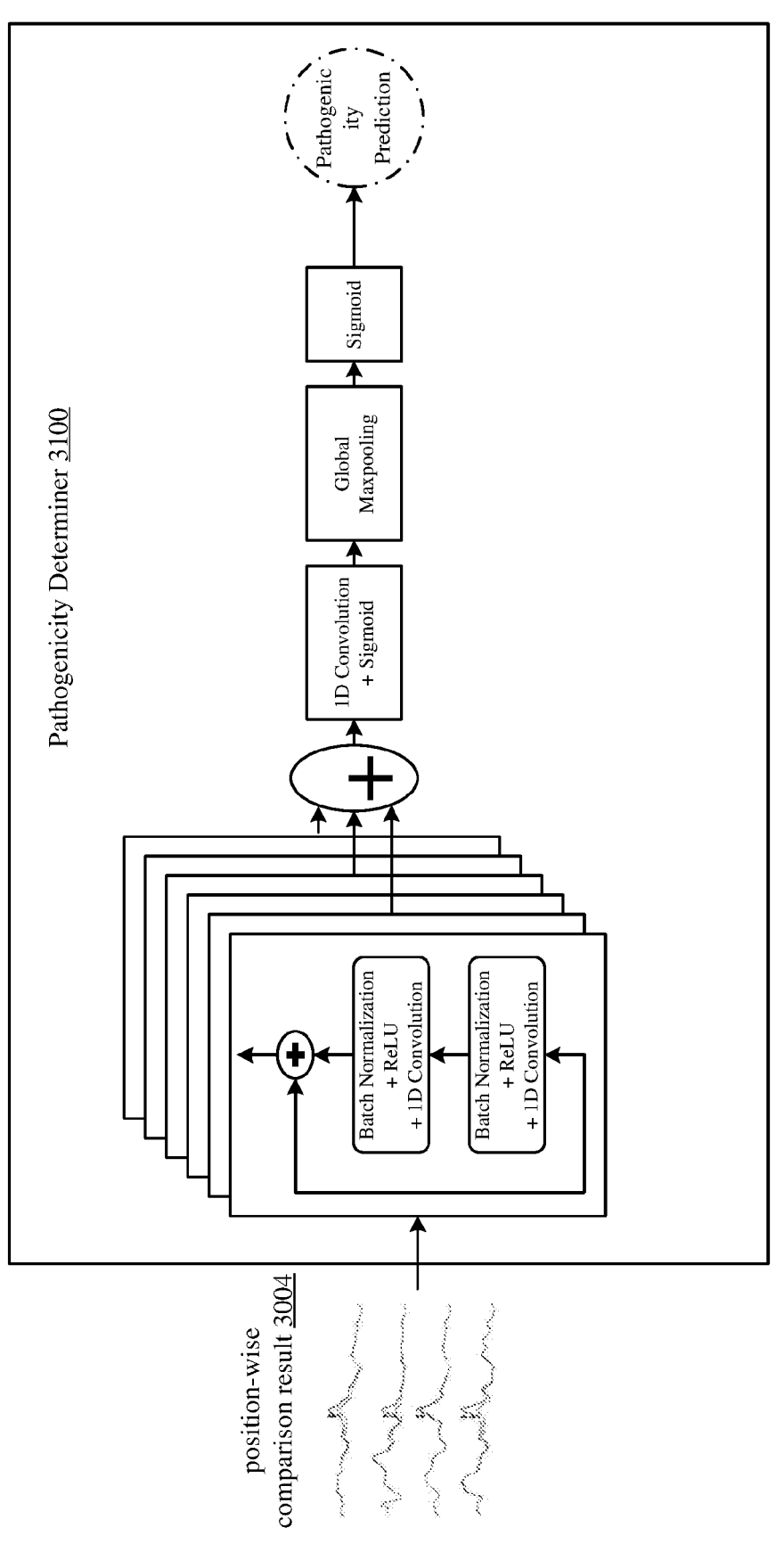
FIG. 31 shows an example pathogenicity classifier.
Figure 32:
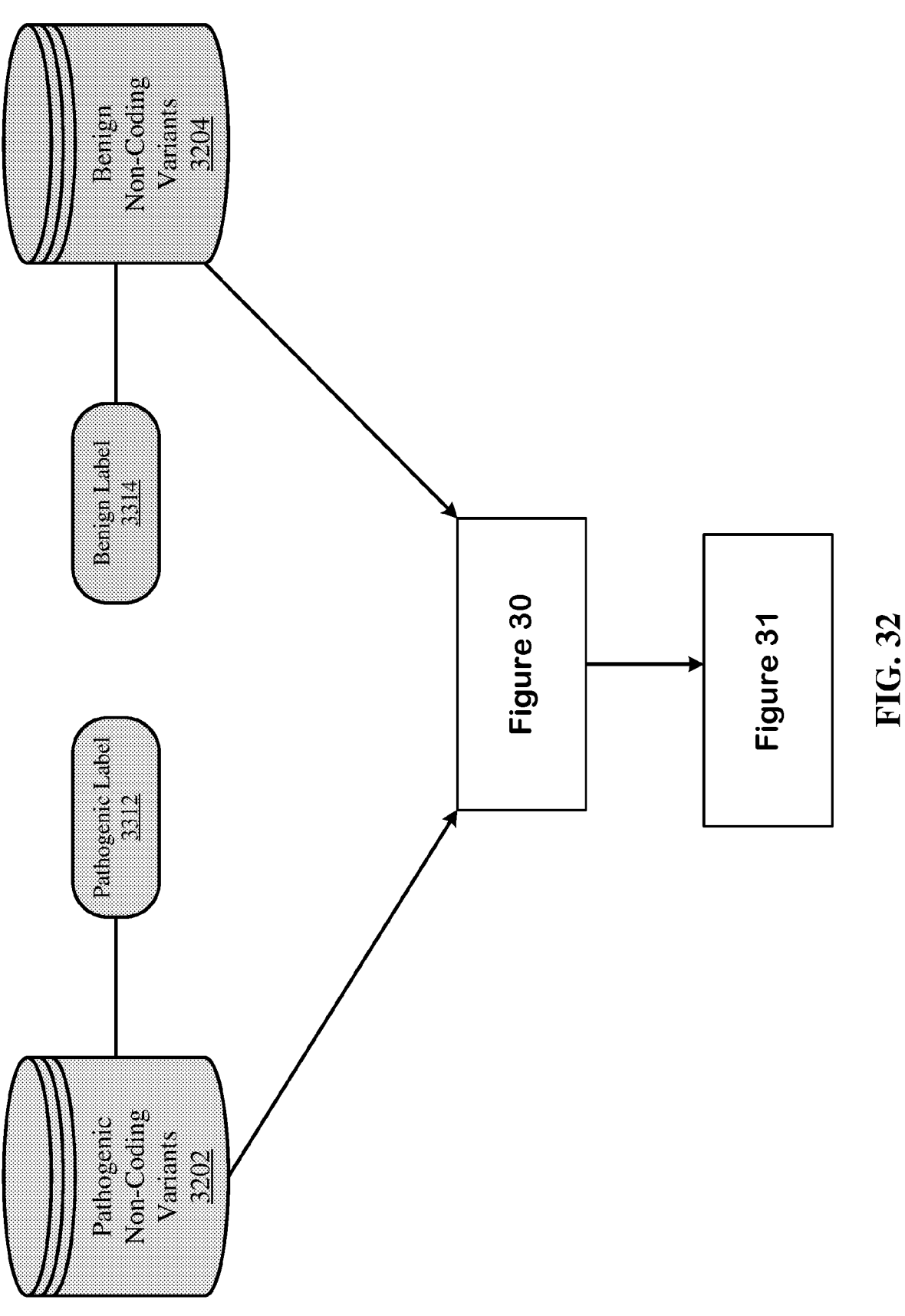
FIG. 32 depicts one implementation of training the pathogenicity classifier using training data that includes a pathogenic set of non-coding variants that are annotated with a pathogenic label (e.g., "1") and a benign set of non-coding variants that are annotated with a benign label (e.g., "0").

FIG. 29 depicts a reference sequence 2902 and an alternative/variant sequence 2912. FIG. 30 illustrates one implementation of generating a position-wise comparison result using the sequence-to-sequence model 2700.

In one implementation, the input preparation module 2610 that accesses a sequence database and generates (i) the reference sequence 2902 that contains, at a target position 2932, a base, wherein the base is flanked by downstream 2942 and upstream context bases 2946, and (ii) the alternative sequence 2912 that contains, at the target position, a variant 2922 of the base, wherein the variant is flanked by the downstream and upstream context bases. The sequence-to-sequence model 2700 processes the reference sequence and generates a reference output 3014, wherein the reference output specifies, for each base in the reference sequence 2902, signal levels of a plurality of epigenetic tracks, and processes the alternative sequence 2912 and generates an alternative output 3024, wherein the alternative output 3024 specifies, for each base in the alternative sequence 2912, the signal levels of the plurality of epigenetic tracks.

A comparator 3002 applies a position-wise deterministic comparison function to the reference output 3014 and the alternative output 3024 generated for bases in the reference sequence 2902 and the alternative sequence 2912, and generates a position-wise comparison result 3004 based on differences, caused by the variant in the alternative sequence 2912, between the signal levels of the reference output 3014 and the signal levels of the alternative output 3024.

The position-wise deterministic comparison function calculates an element-wise difference between the reference output 3014 and the alternative output 3024. The position-wise deterministic comparison function calculates an element-wise sum of the reference output 3014 and the alternative output 3024. The position-wise deterministic comparison function calculates an element-wise ratio between the reference output 3014 and the alternative output 3024.

Pathogenicity Determiner

A pathogenicity determiner 3100 processes the position-wise comparison result 3004 and produces an output which scores the variant in the alternative sequence 2912 as pathogenic or benign. The pathogenicity determiner 3100 processes the position-wise comparison result 3004 and generates an alternative representation of the position-wise comparison result 3004. The position-wise comparison result 3004 is based on differences, caused by a variant in the alternative sequence 2912, between signal levels of a plurality of epigenetic tracks determined for bases in a reference sequence, and signal levels of the plurality of epigenetic tracks determined for bases in the alternative sequence. An output module (e.g., sigmoid) processes the alternative representation of the position-wise comparison result and produces an output which scores the variant in the alternative sequence as pathogenic or benign. In implementation, if the output above a threshold (above 0.5), then the variant is classified as pathogenic.

Gene Expression Based Pathogenicity Label

Figure 34:
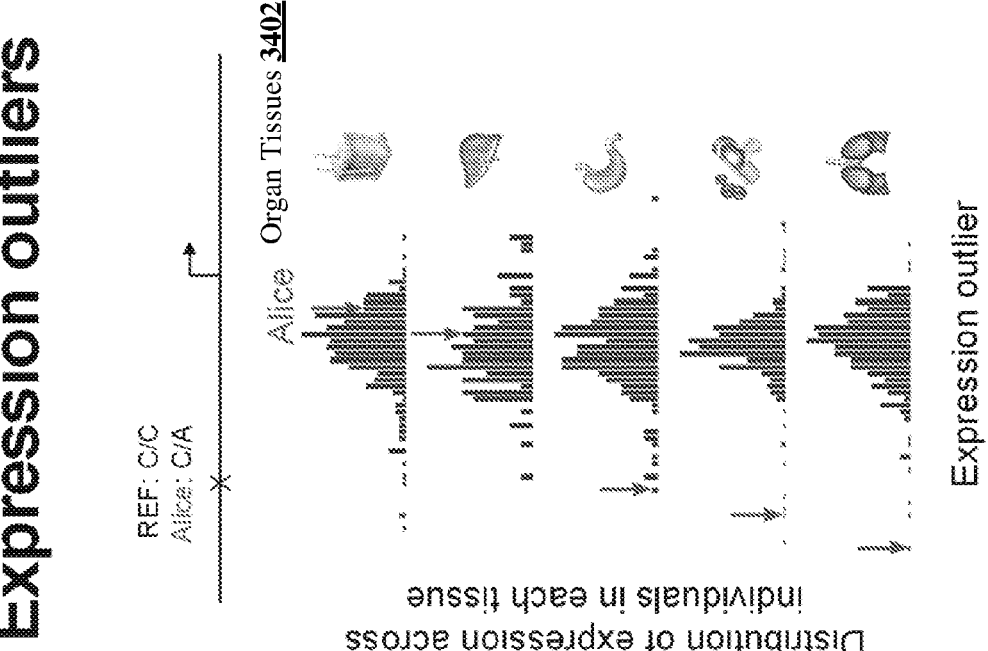
FIG. 34 shows one implementation of how a pathogenic set of non-coding variants is generated.

The pathogenicity determiner 3100 is trained using training data that includes a pathogenic set of non-coding variants 3202 that are annotated with a pathogenic label 3312 (e.g., "1") and a benign set of non-coding variants 3204 that are annotated with a benign label 3314 (e.g., "0");

FIG. 34 shows one implementation of how a pathogenic set of non-coding variants is generated. The pathogenic set of non-coding variants includes singletons that appear only in a single individual among a cohort of individuals, and, for genes adjacent to the non-coding variants in the pathogenic set, the single individual exhibited under-expression across a plurality of tissues/organ tissues 3402. The pathogenic set of non-coding variants are considered "expression outliers" in FIG. 34.

The benign set of non-coding variants are singletons that appear only in a single individual among the cohort of individuals and, for genes adjacent to the non-coding variants in the benign set, the single individual did not exhibit the under-expression across the plurality of tissues.

The under-expression is determined by analyzing distributions of expressions exhibited by the cohort of individuals for each of the genes across each of the plurality of tissues, and calculating a median z-score for the single individual based on the distributions.

In each tissue, we compute the z-scores for each individual. That is, if x_i is the value for individual i, m is the mean of x_i values across all individuals, and s is the standard deviation, then the z-score for individual i, is going to be (x_i−m)/s. Then we test whether z_i is below some threshold (e.g., −1.5 as mentioned in the claim). We also require that this happens for the same individual in multiple tissues (e.g., at least two tissues where z_i<−1.5).

Additional details about gene expression-based pathogenic labelling can be found in Appendix B, which is bodily incorporated in the Priority Provisional Application No. 62/903,700.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

Other implementations may include a non-transitory computer readable storage medium storing instructions executable by a processor to perform actions of the system described above. Yet another implementation may include a method performing actions of the system described above.

Additional details about the technology disclosed can be found in Appendix A, which is bodily incorporated in the Priority Provisional Application No. 62/903,700.

Model Architecture

We trained several ultra-deep convolutional neural network-based models for the sequence-to-sequence epigenetic model 2700 and/or the pathogenicity determiner 3100. We designed four architectures, namely, Model-80nt, Model-400nt, Model-2k and Model-10k, which use 40, 200, 1,000 and 5,000 nucleotides on each side of a position of interest as input respectively, the input to the models is a sequence of one-hot encoded nucleotides, where A, C, G and T (or equivalently U) are encoded as [1, 0, 0, 0], [0, 1, 0, 0], [0, 0, 1, 0] and [0, 0, 0, 1].

The model architectures can be used for the sequence-to-sequence epigenetic model 2700 and/or the pathogenicity determiner 3100.

The model architectures have a modified WaveNet-style architecture that iterating over particular locations in an input promoter sequence and over three base variations from a reference base found at a particular location. The modified WaveNet-style architecture can calculate up to 9,000 outputs for 3,000 locations in the input, as each location has up to three single base variations. The modified WaveNet-style architecture scales relatively well, because intermediate calculations are reused. The pathogenicity classifiers determine in a single invocation of the modified WaveNet-like architecture pathogenicity likelihood scores for at least one of the three base variations at a multiplicity of the particular locations in the input promoter sequence and store the pathogenicity likelihood scores determined in the single invocation. The determining of at least one of the three base variations further includes determining all of the three variations. The multiplicity of the particular locations is at least 500 or 1,000, or 1500, or 2000, or ninety percent of the input promoter sequence.

The basic unit of the model architectures is a residual block (He et al., 2016b), which consists of batch-normalization layers (Ioffe and Szegedy, 2015), rectified linear units (ReLU), and convolutional units organized in a specific manner (FIGS. 21, 22, 23, and 24). Residual blocks are commonly used when designing deep neural networks. Prior to the development of residual blocks, deep neural networks consisting of many convolutional units stacked one after the other were very difficult to train due to the problem of exploding/vanishing gradients (Glorot and Bengio, 2010), and increasing the depth of such neural networks often resulted in a higher training error (He et al., 2016a). Through a comprehensive set of computational experiments, architectures consisting of many residual blocks stacked one after the other were shown to overcome these issues (He et al., 2016a).

The complete model architectures are provided in FIGS. 21, 22, 23, and 24. The architectures consist of K stacked residual blocks connecting the input layer to the penultimate layer, and a convolutional unit with softmax activation connecting the penultimate layer to the output layer. The residual blocks are stacked such that the output of the $i^{th}$ residual block is connected to the input of the $i+1^{th}$ residual block. Further, the output of every fourth residual block is added to the input of the penultimate layer. Such "skip connections" are commonly used in deep neural networks to increase convergence speed during training (Oord et al., 2016).

Each residual block has three hyper-parameters N, W and D, where N denotes the number of convolutional kernels, W denotes the window size and D denotes the dilation rate (Yu and Koltun, 2016) of each convolutional kernel. Since a convolutional kernel of window size W and dilation rate D extracts features spanning (W−1)D neighboring positions, a residual block with hyper-parameters N, W and D extracts features spanning 2(W−1)D neighboring positions. Hence, the total neighbor span of the Model architectures is given by $$S = \sum_{i=1}^{K} 2(W_i - 1)D_i,$$

where $N_i$, $W_i$ and $D_i$ are the hyper-parameters of the $i^{th}$ residual block. For Model-80nt, Model-400nt, Model-2k and Model-10k architectures, the number of residual blocks and the hyper-parameters for each residual block were chosen so that S is equal to 80, 400, 2,000 and 10,000, respectively.

The model architectures only have normalization and non-linear activation units in addition to convolutional units. Consequently, the models can be used in a sequence-to-sequence mode with variable sequence length (Oord et al., 2016). For example, the input to the Model-10k model (S=10,000) is a one-hot encoded nucleotide sequence of length S/2+1+S/2, and the output is an 1×3 matrix, corresponding to the three scores of the/central positions in the input, i.e., the positions remaining after excluding the first and last S/2 nucleotides. This feature can be leveraged to obtain a tremendous amount of computational saving during training as well as testing. This is due to the fact that most of the computations for positions which are close to each other are common, and the shared computations need to be done only once by the models when they are used in the sequence-to-sequence epigenetic model 2700 and/or the pathogenicity determiner 3100.

Our models adopted the architecture of residual blocks, which has become widely adopted due to its success in image classification. The residual blocks comprise repeating units of convolution, interspersed with skip connections that allow information from earlier layers to skip over residual blocks. In each residual block, the input layer is first batch normalized, followed by an activation layer using rectified linear units (ReLU). The activation is then passed through a 1D convolution layer. This intermediate output from the 1D convolution layer is again batch normalized and ReLU activated, followed by another 1D convolution layer. At the end of the second 1D convolution, we summed its output with the original input into the residual block, which acts as a skip connection by allowing the original input information to bypass the residual block. In such an architecture, termed a deep residual learning network by its authors, the input is preserved in its original state and the residual connections are kept free of nonlinear activations from the model, allowing effective training of deeper networks.

Following the residual blocks, the softmax layer computes probabilities of the three states for each amino acid, among which the largest softmax probability determines the state of the amino acid. The model is trained with accumulated categorical cross entropy loss function for the whole protein sequence using the ADAM optimizer.

Atrous/dilated convolutions allow for large receptive fields with few trainable parameters. An atrous/dilated convolution is a convolution where the kernel is applied over an area larger than its length by skipping input values with a certain step, also called atrous convolution rate or dilation factor. Atrous/dilated convolutions add spacing between the elements of a convolution filter/kernel so that neighboring input entries (e.g., nucleotides, amino acids) at larger intervals are considered when a convolution operation is performed. This enables incorporation of long-range contextual dependencies in the input. The atrous convolutions conserve partial convolution calculations for reuse as adjacent nucleotides are processed.

The illustrated example uses 1D convolutions. In other implementations, the model can use different types of convolutions such as 2D convolutions, 3D convolutions, dilated or atrous convolutions, transposed convolutions, separable convolutions, and depthwise separable convolutions. Some layers also use ReLU activation function which greatly accelerates the convergence of stochastic gradient descent compared to saturating nonlinearities such as sigmoid or hyperbolic tangent. Other examples of activation functions that can be used by the technology disclosed include parametric ReLU, leaky ReLU, and exponential linear unit (ELU).

Some layers also use batch normalization (Ioffe and Szegedy 2015). Regarding batch normalization, distribution of each layer in a convolution neural network (CNN) changes during training and it varies from one layer to another. This reduces the convergence speed of the optimization algorithm. Batch normalization is a technique to overcome this problem. Denoting the input of a batch normalization layer with x and its output using z, batch normalization applies the following transformation on x:

$$z = \frac{x - \mu}{\sqrt{\sigma^2 + \varepsilon}} \gamma + \beta$$

Batch normalization applies mean-variance normalization on the input x using $\mu$ and $\sigma$ and linearly scales and shifts it using $\gamma$ and $\beta$. The normalization parameters $\mu$ and $\sigma$ are computed for the current layer over the training set using a method called exponential moving average. In other words, they are not trainable parameters. In contrast, $\gamma$ and $\beta$ are trainable parameters. The values for $\mu$ and $\sigma$ calculated during training are used in forward pass during inference.

Figure 19:
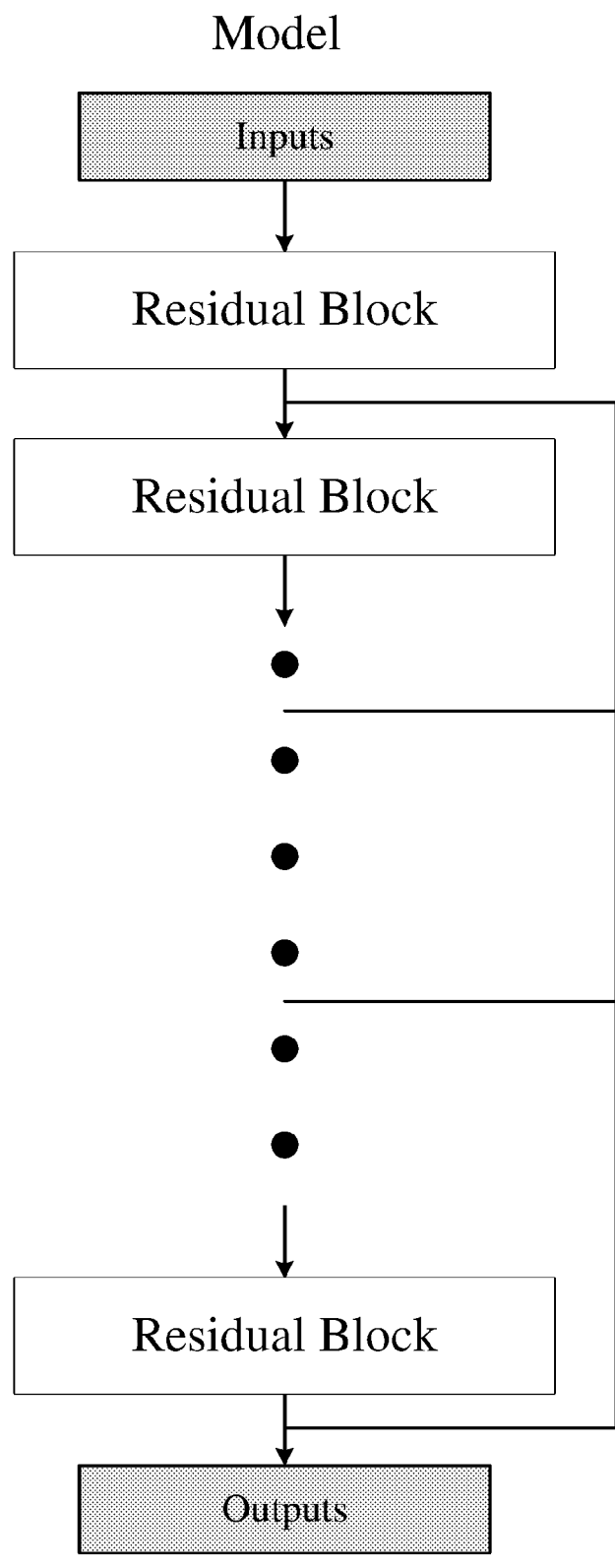
FIG. 19 depicts one implementation of the architecture of a model that can be used a sequence-to-sequence epigenetic model and/or a pathogenicity determiner.

As shown in FIG. 19, the model can comprise groups of residual blocks arranged in a sequence from lowest to highest. Each group of residual blocks is parameterized by a number of convolution filters in the residual blocks, a convolution window size of the residual blocks, and an atrous convolution rate of the residual blocks.

Figure 20:
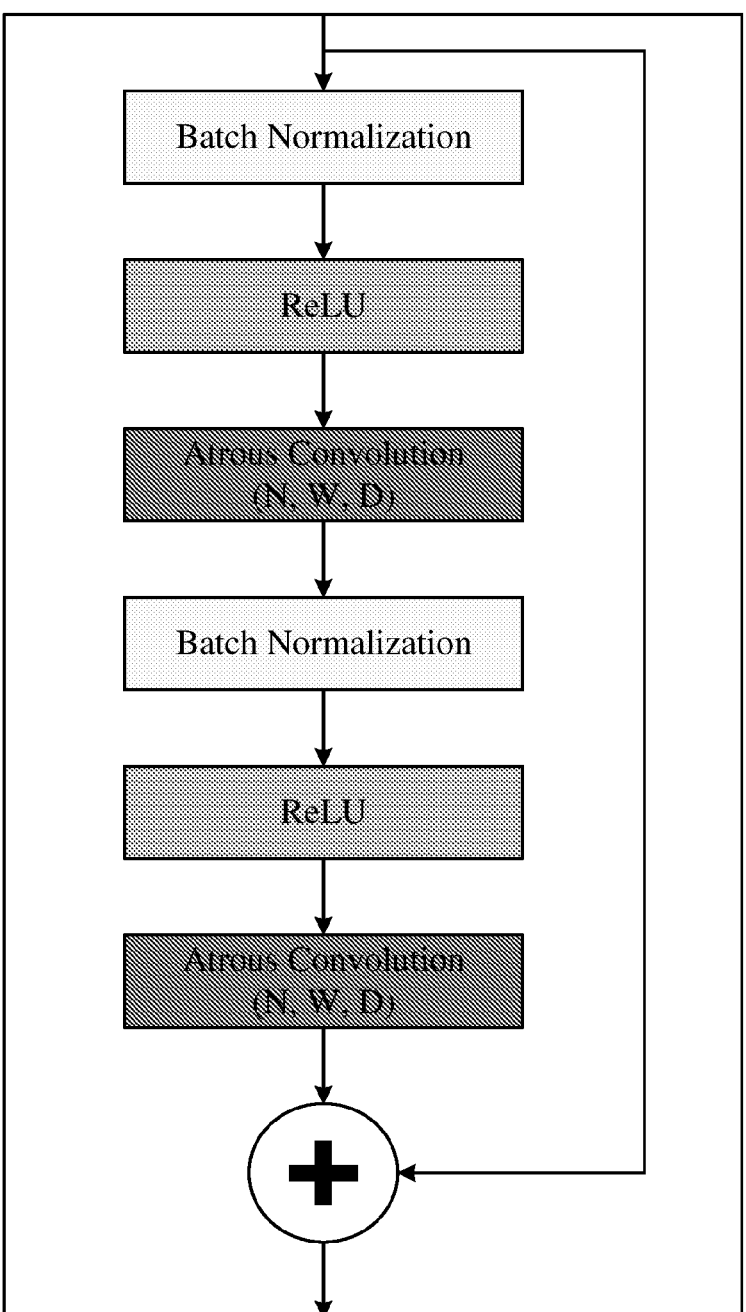
FIG. 20 shows one implementation of a residual block that can used by the sequence-to-sequence epigenetic model and/or the pathogenicity determiner.

As shown in FIG. 20, each residual block can comprise at least one batch normalization layer, at least one rectified linear unit (abbreviated ReLU) layer, at least one atrous convolution layer, and at least one residual connection. In such an implementation, each residual block comprises two batch normalization layers, two ReLU non-linearity layers, two atrous convolution layers, and one residual connection.

As shown in FIGS. 21, 22, 23, and 24, in the model, the atrous convolution rate progresses non-exponentially from a lower residual block group to a higher residual block group.

As shown in FIGS. 21, 22, 23, and 24, in the model, the convolution window size varies between groups of residual blocks.

Figure 21:
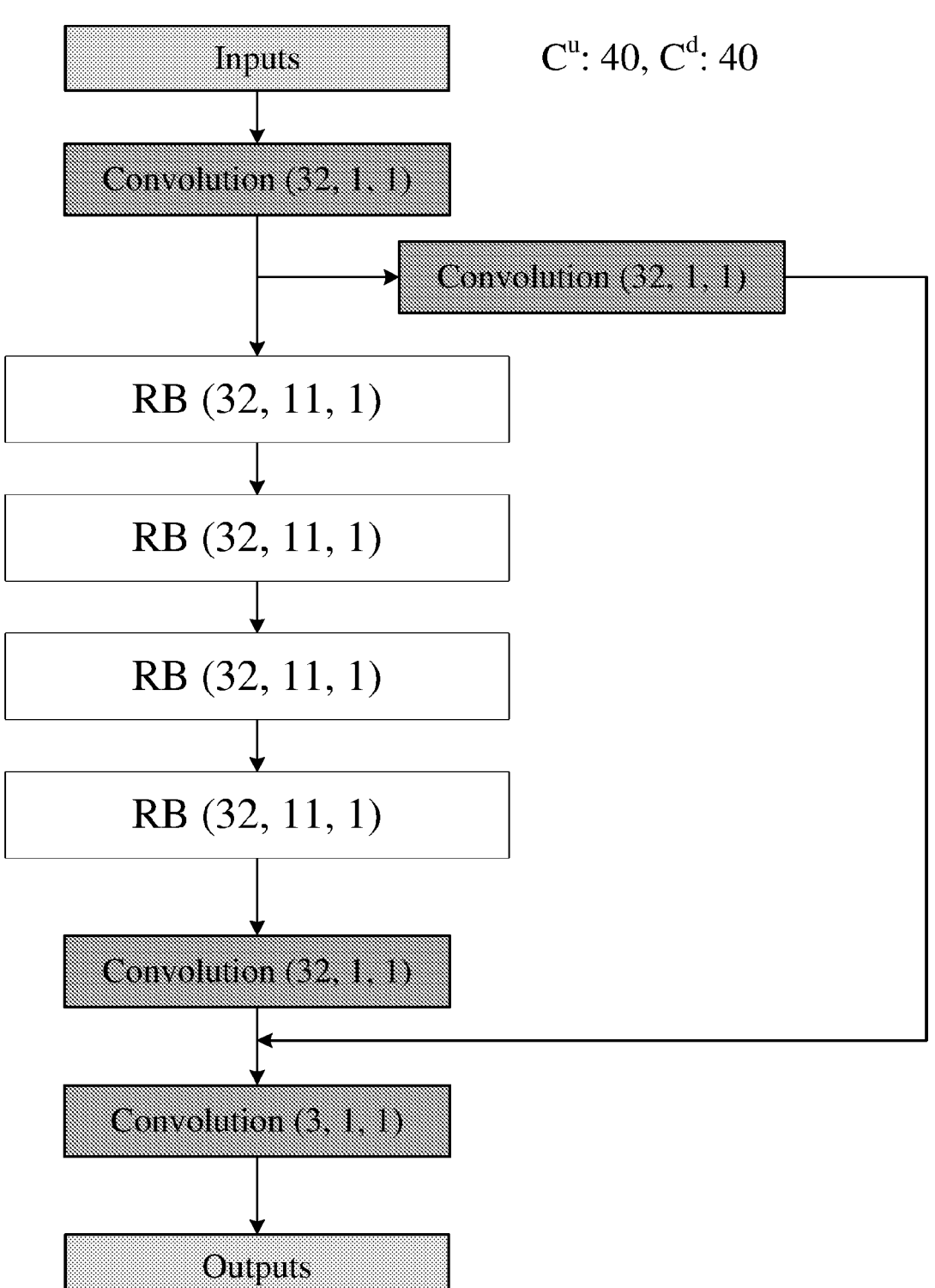
FIG. 21 depicts another implementation of the architecture of the sequence-to-sequence epigenetic model and/or the pathogenicity determiner, referred to herein as "Model80".

The model can be configured to evaluate an input that comprises a target nucleotide sequence further flanked by 40 upstream context nucleotides and 40 downstream context nucleotides. In such an implementation, the model includes one group of four residual blocks and at least one skip connection. Each residual block has 32 convolution filters, 11 convolution window size, and 1 atrous convolution rate. This implementation of the model is referred to herein as "SpliceNet80" and is shown in FIG. 21.

Figure 22:
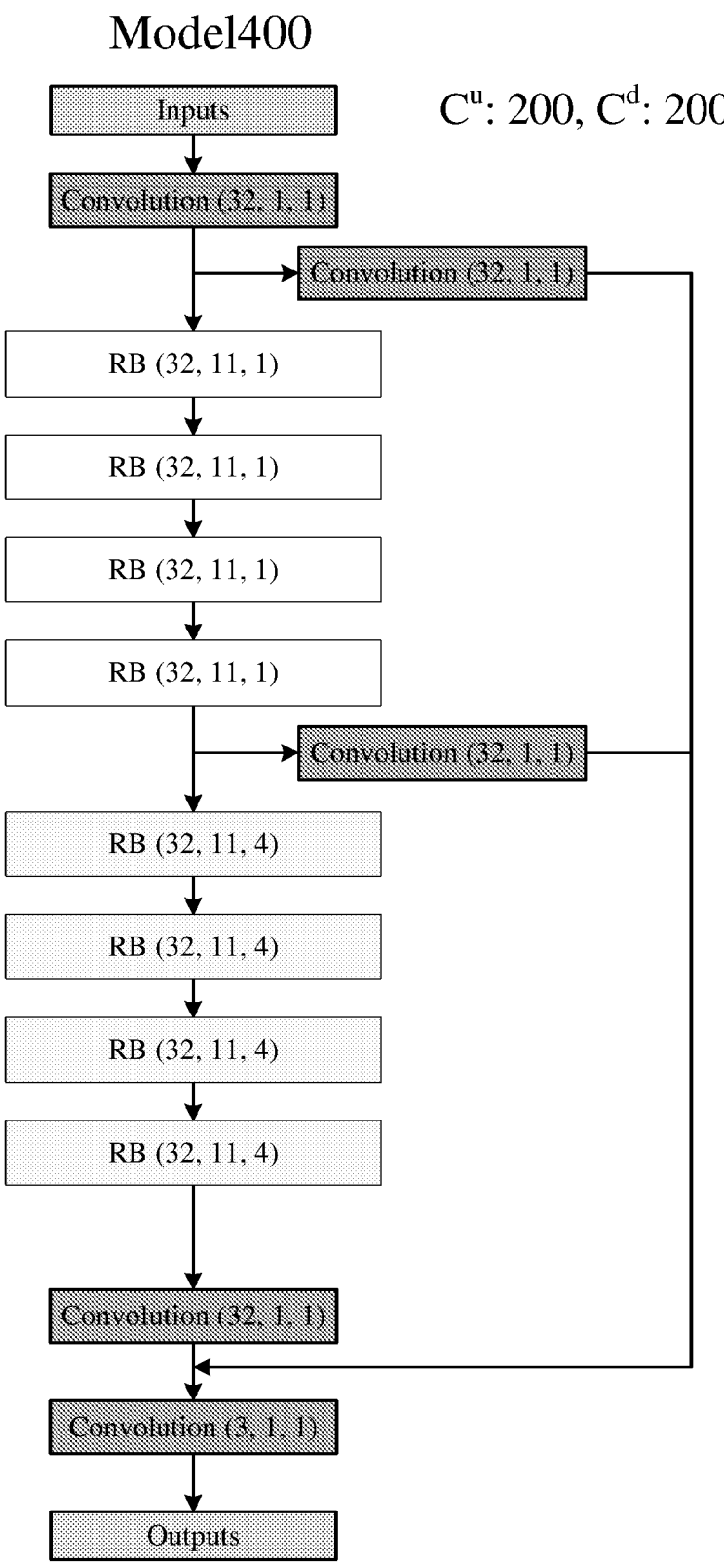
FIG. 22 depicts yet another implementation of the architecture of the sequence-to-sequence epigenetic model and/or the pathogenicity determiner, referred to herein as "Model400".

The model can be configured to evaluate an input that comprises the target nucleotide sequence further flanked by 200 upstream context nucleotides and 200 downstream context nucleotides. In such an implementation, the model includes at least two groups of four residual blocks and at least two skip connections. Each residual block in a first group has 32 convolution filters, 11 convolution window size, and 1 atrous convolution rate. Each residual block in a second group has 32 convolution filters, 11 convolution window size, and 4 atrous convolution rate. This implementation of the model is referred to herein as "SpliceNet400" and is shown in FIG. 22.

Figure 23:
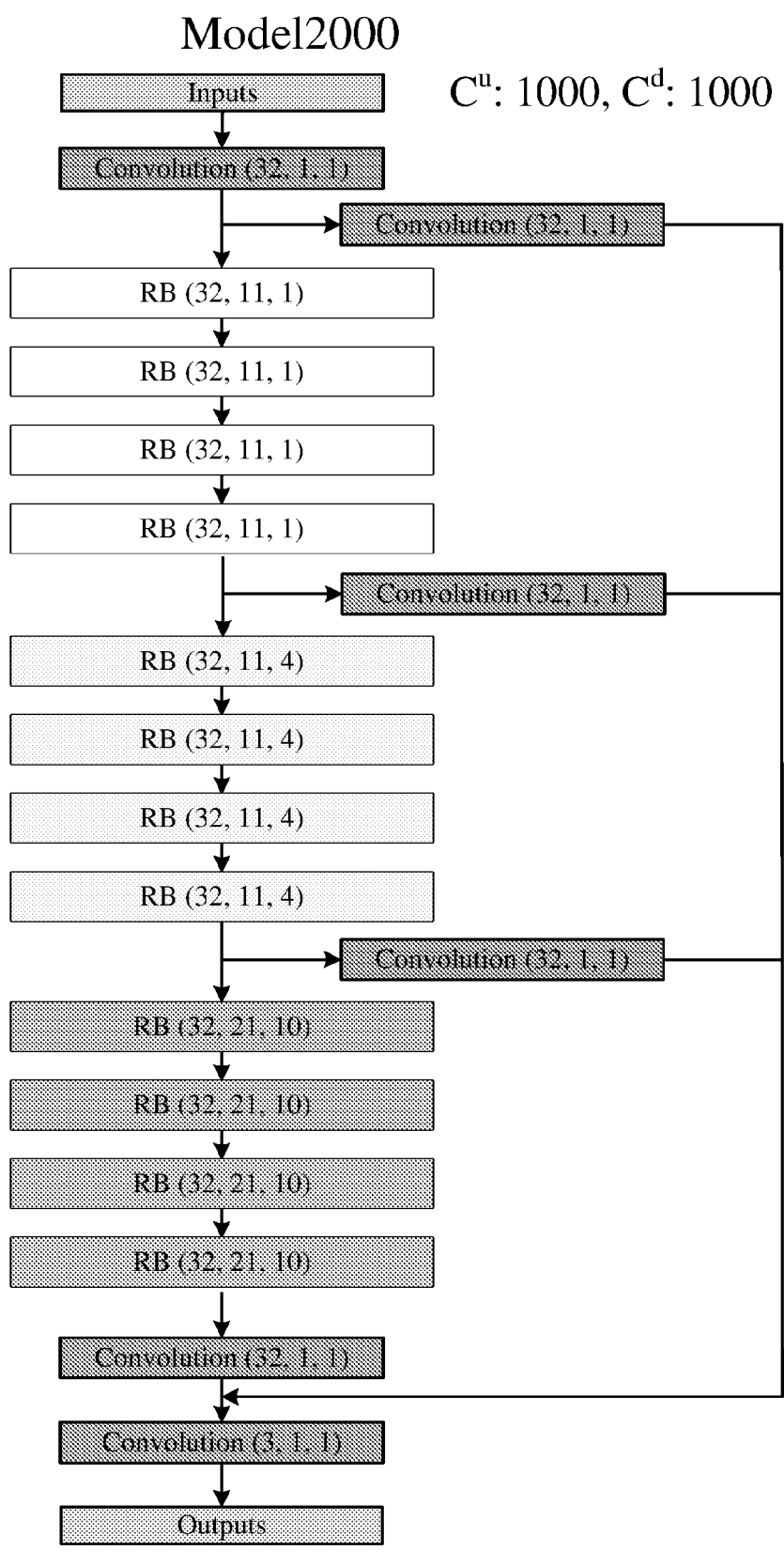
FIG. 23 depicts yet further implementation of the architecture of the sequence-to-sequence epigenetic model and/or the pathogenicity determiner, referred to herein as "Model2000".

The model can be configured to evaluate an input that comprises a target nucleotide sequence further flanked by 1000 upstream context nucleotides and 1000 downstream context nucleotides. In such an implementation, the model includes at least three groups of four residual blocks and at least three skip connections. Each residual block in a first group has 32 convolution filters, 11 convolution window size, and 1 atrous convolution rate. Each residual block in a second group has 32 convolution filters, 11 convolution window size, and 4 atrous convolution rate. Each residual block in a third group has 32 convolution filters, 21 convolution window size, and 19 atrous convolution rate. This implementation of the model is referred to herein as "SpliceNet2000" and is shown in FIG. 23.

Figure 24:
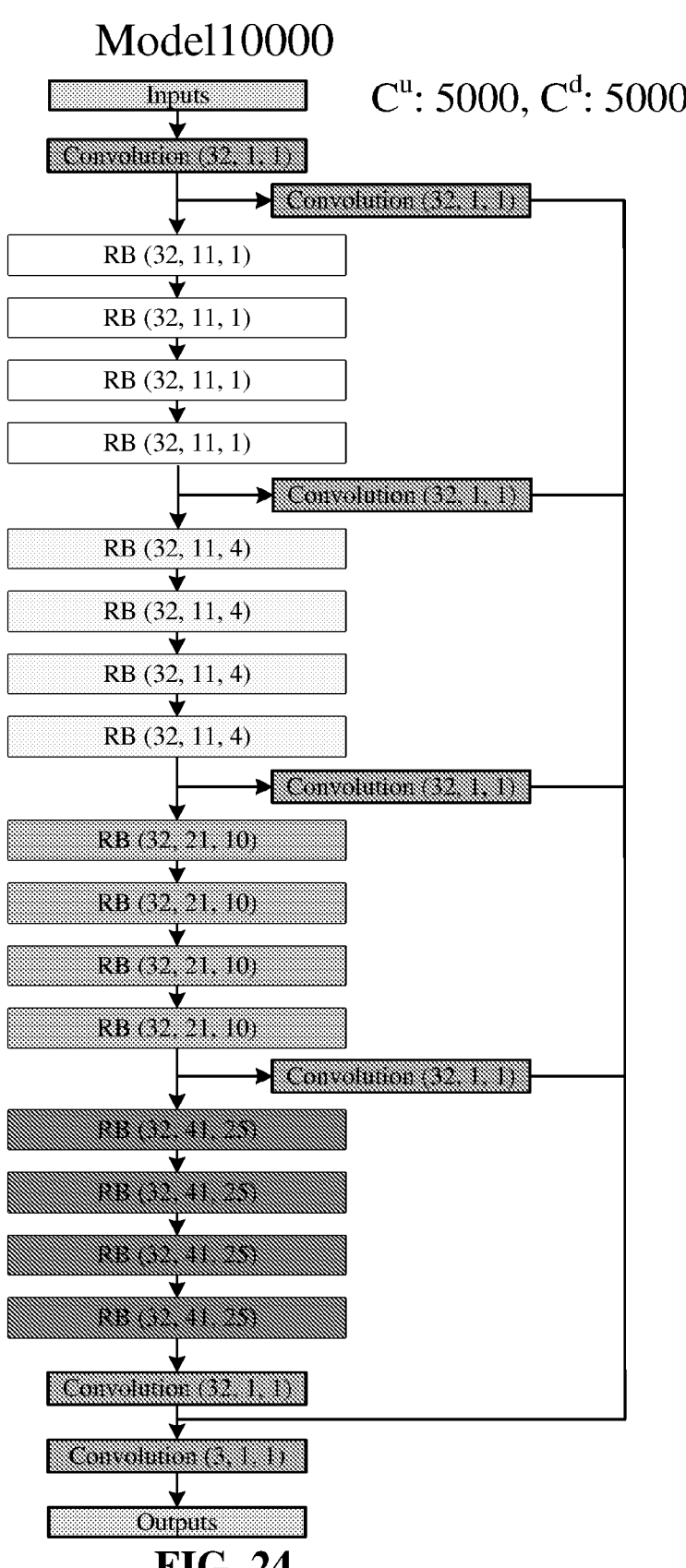
FIG. 24 depicts yet another implementation of the architecture of the sequence-to-sequence epigenetic model and/or the pathogenicity determiner, referred to herein as "Model10000".

The model can be configured to evaluate an input that comprises a target nucleotide sequence further flanked by 5000 upstream context nucleotides and 5000 downstream context nucleotides. In such an implementation, the model includes at least four groups of four residual blocks and at least four skip connections. Each residual block in a first group has 32 convolution filters, 11 convolution window size, and 1 atrous convolution rate. Each residual block in a second group has 32 convolution filters, 11 convolution window size, and 4 atrous convolution rate. Each residual block in a third group has 32 convolution filters, 21 convolution window size, and 19 atrous convolution rate. Each residual block in a fourth group has 32 convolution filters, 41 convolution window size, and 25 atrous convolution rate. This implementation of the model is referred to herein as "SpliceNet10000" and is shown in FIG. 24

Figure 18:
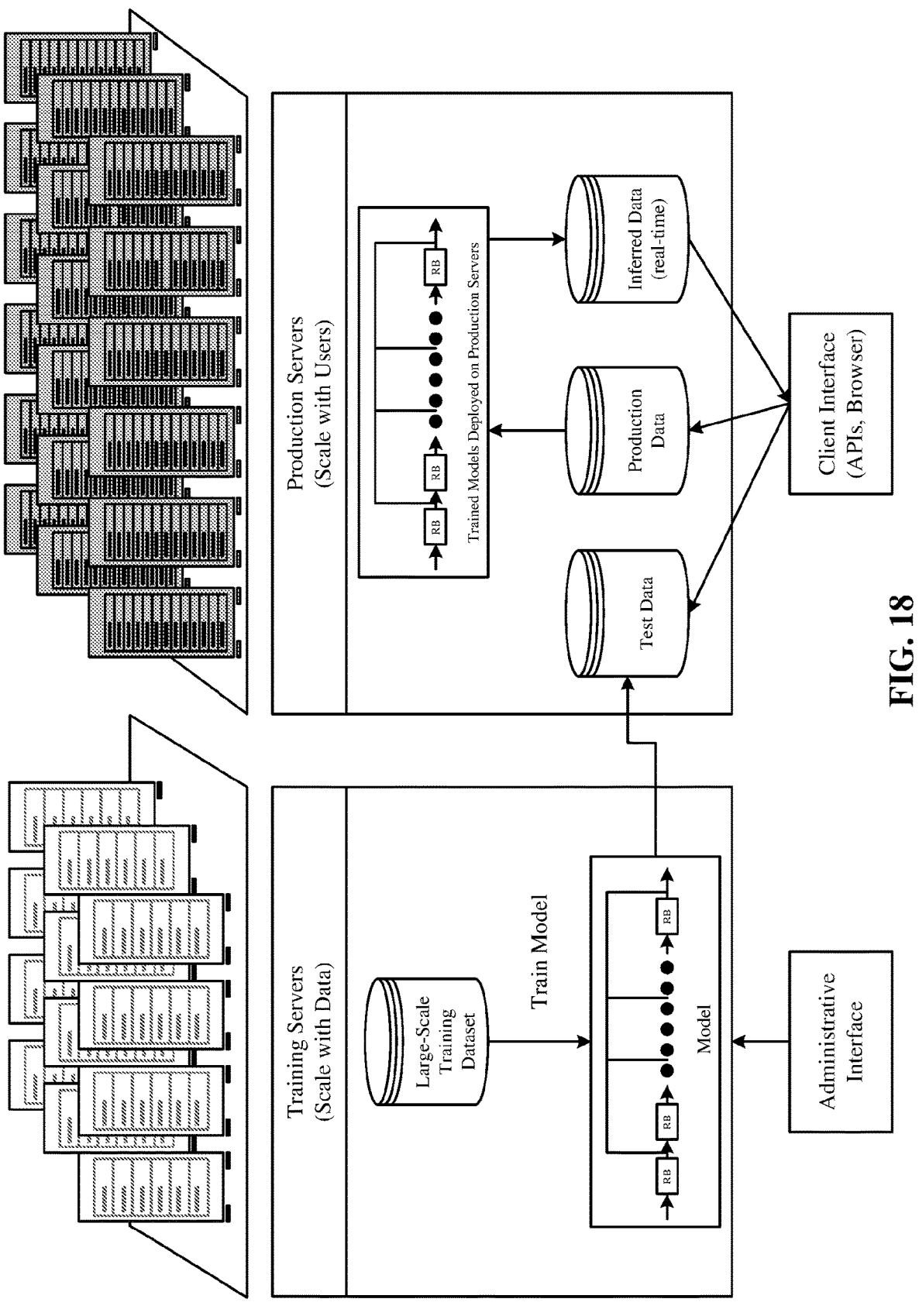
FIG. 18 illustrates one implementation of a computing environment with training servers and production servers that can be used to implement the technology disclosed.

The trained model can be deployed on one or more production servers that receive input sequences from requesting clients, as shown in FIG. 18. In such an implementation, the production servers process the input sequences through the input and output stages of the model to produce outputs that are transmitted to the clients, as shown in FIG. 18.

Figure 35:
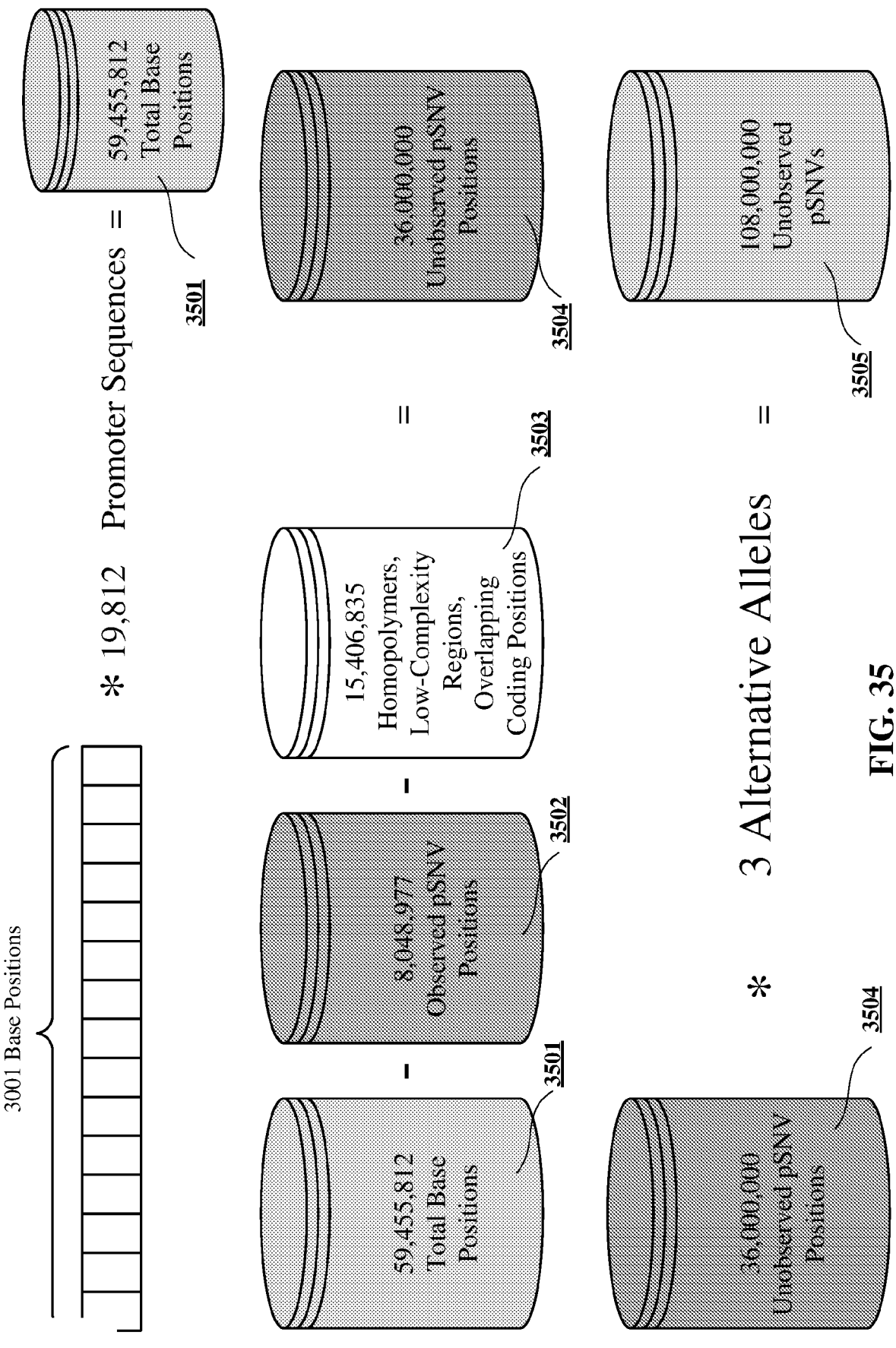
FIG. 35 depicts how training datasets are generated for the technology disclosed.

FIG. 35 depicts how training datasets are generated for the technology disclosed. First, promoter sequences in 19,812 genes are identified, according to one implementation. In some implementations, each of the 19,812 promoter sequences has 3001 base positions (not including the flanking contexts outside the promoter region), which produces 59,455,812 total base positions 3501 (in grey).

In one implementation, from the 59,455,812 total base positions 3501, 8,048,977 observed pSNV positions 3502 are qualified as benign positions. 8,048,977 benign positions 3502 yield 8,701,827 observed pSNVs, which form a final benign set, according to one implementation. In some implementations, the benign pSNVs are observed in human and non-human primate species such as chimpanzee, bonobo, gorilla, orangutan, rhesus, and marmoset.

In some implementations, the criterion for inclusion in the benign set is that the minor allele frequency of an observed pSNV should be greater than 0.1%. Such a criterion produces 600,000 observed pSNVs, according to one implementation. In other implementations, the inclusion criterion does not take into account the minor allele frequencies of observed pSNVs. That is, as long as a pSNV is observed in human and the non-human primate species, it is included in the benign set and thus labeled as benign. The second inclusion strategy produces the much larger benign set of 8,701,827 observed pSNVs, according to one implementation.

Further, from the 59,455,812 total base positions 3501, 15,406,835 unobserved pSNV positions 3503 are removed that belong to homopolymer regions, low-complexity regions, and overlapping coding positions (e g, start or stop codons), which are considered either unreliable due to sequence-specific errors or irrelevant to the analysis of non-coding variants.

Thus, in some implementations, what results is 36,000,000 unobserved pSNV positions 3504, from which a total of 108,000,000 unobserved pSNVs 3505 are derived by mutating each of the 36,000,000 loci to the three alternative single-base alleles. These 108,000,000 unobserved pSNVs form the final pool 3505 of substitutionally generated unobserved pSNVs, according to one implementation.

Computer System

Figure 33:
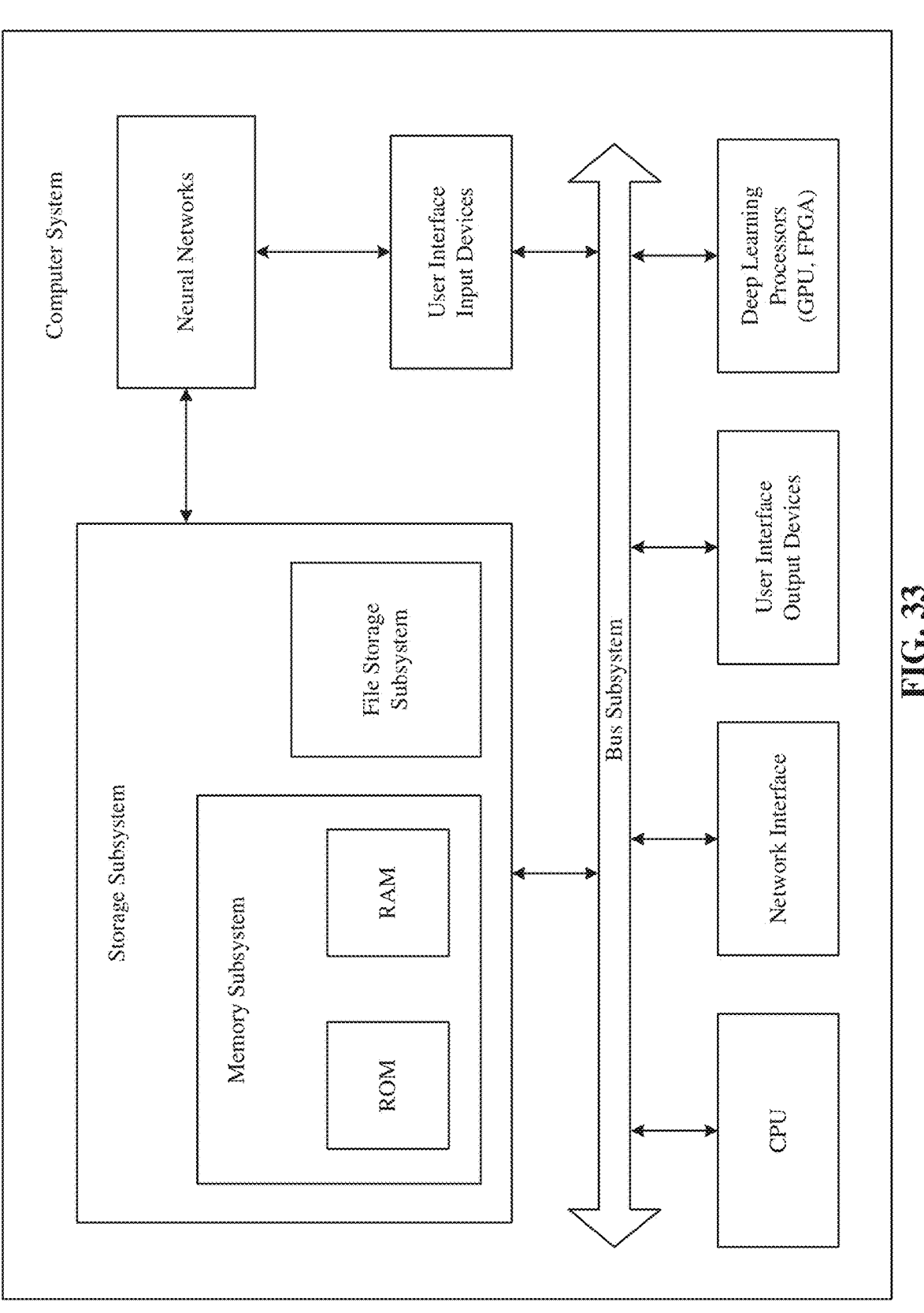
FIG. 33 is a simplified block diagram of a computer system that can be used to implement the technology disclosed.

FIG. 33 is a simplified block diagram of a computer system that can be used to implement the technology disclosed. Computer system typically includes at least one processor that communicates with a number of peripheral devices via bus subsystem. These peripheral devices can include a storage subsystem including, for example, memory devices and a file storage subsystem, user interface input devices, user interface output devices, and a network interface subsystem. The input and output devices allow user interaction with computer system. Network interface subsystem provides an interface to outside networks, including an interface to corresponding interface devices in other computer systems.

In one implementation, the neural networks such as ACNN and CNN are communicably linked to the storage subsystem and user interface input devices.

User interface input devices can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system.

User interface output devices can include a display subsystem, a printer, a fax machine, or non-visual displays such as audio output devices. The display subsystem can include a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system to the user or to another machine or computer system.

Storage subsystem stores programming and data constructs that provide the functionality of some or all of the modules and methods described herein. These software modules are generally executed by processor alone or in combination with other processors.

Memory used in the storage subsystem can include a number of memories including a main random access memory (RAM) for storage of instructions and data during program execution and a read only memory (ROM) in which fixed instructions are stored. A file storage subsystem can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem in the storage subsystem, or in other machines accessible by the processor.

Bus subsystem provides a mechanism for letting the various components and subsystems of computer system communicate with each other as intended. Although bus subsystem is shown schematically as a single bus, alternative implementations of the bus subsystem can use multiple busses.

Computer system itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system depicted in FIG. 33 is intended only as a specific example for purposes of illustrating the technology disclosed. Many other configurations of computer system are possible having more or less components than the computer system depicted in FIG. 33.

The deep learning processors can be GPUs or FPGAs and can be hosted by a deep learning cloud platforms such as Google Cloud Platform, Xilinx, and Cirrascale. Examples of deep learning processors include Google's Tensor Processing Unit (TPU), rackmount solutions like GX4 Rackmount Series, GX8 Rackmount Series, NVIDIA DGX-1, Microsoft' Stratix V FPGA, Graphcore's Intelligent Processor Unit (IPU), Qualcomm's Zeroth platform with Snapdragon processors, NVIDIA's Volta, NVIDIA's DRIVE PX, NVIDIA's JETSON TX1/TX2 MODULE, Intel's Nirvana, Movidius VPU, Fujitsu DPI, ARM's DynamicIQ, IBM TrueNorth, and others.

The preceding description is presented to enable the making and use of the technology disclosed. Various modifications to the disclosed implementations will be apparent, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein. The scope of the technology disclosed is defined by the appended claims.

CLAUSES

The following clauses are included herein.
Artificial Intelligence-Based Pathogenicity Classification of Noncoding Variants 1. An artificial intelligence-based system, comprising:
an input preparation module that accesses a sequence database and generates an input base sequence, wherein the input base sequence comprises
(i) a target base sequence with target bases, wherein the target base sequence is flanked by
(ii) a right base sequence with downstream context bases, and
(iii) a left base sequence with upstream context bases;
a sequence-to-sequence model that processes the input base sequence and generates an alternative representation of the input base sequence; and
an output module that processes the alternative representation of the input base sequence and produces at least one per-base output for each of the target bases in the target base sequence;
wherein the per-base output specifies, for a corresponding target base, signal levels of a plurality of epigenetic tracks.

2. The artificial intelligence-based system of clause 1, wherein the per-base output uses continuous values to specify the signal levels of the plurality of epigenetic tracks.

3. The artificial intelligence-based system of clause 1, wherein the output module further comprises a plurality of per-track processors, with each per-track processor corresponds to a respective epigenetic track in the plurality of epigenetic tracks and produces a signal level for a corresponding epigenetic track.

4. The artificial intelligence-based system of clause 3, wherein each per-track processor in the plurality of per-track processors processes the alternative representation of the input base sequence, generates a further alternative representation that is specific to a particular per-track processor, and produces the signal level for the corresponding epigenetic track based on the further alternative representation.

5. The artificial intelligence-based system of clause 4, wherein each per-track processor further comprises at least one residual block and a linear module and/or rectified linear unit (ReLU) module, and
wherein the residual block generates the further alternative representation and the linear module and/or the ReLU module processes the further alternative representation and produces the signal level for the corresponding epigenetic track.

6. The artificial intelligence-based system of clause 3, wherein each per-track processor in the plurality of per-track processors processes the alternative representation of the input base sequence and produces the signal level for the corresponding epigenetic track based on the alternative representation.

7. The artificial intelligence-based system of clause 6, wherein each per-track processor further comprises a linear module and/or a ReLU module.

8. The artificial intelligence-based system of clause 1, wherein the plurality of epigenetic tracks includes deoxyribonucleic acid (DNA) methylation changes (e.g., CpG), histone modifications, noncoding ribonucleic acid (ncRNA) expression, and chromatin structural changes (e.g., nucleosome positioning).

9. The artificial intelligence-based system of clause 1, wherein the plurality of epigenetic tracks includes deoxyribonuclease (DNase) tracks.

10. The artificial intelligence-based system of clause 1, wherein the plurality of epigenetic tracks includes histone 3 lysine 27 acetylation (H3K27ac) tracks.

11. The artificial intelligence-based system of clause 1, wherein the sequence-to-sequence model is a convolutional neural network.

12. The artificial intelligence-based system of clause 11, wherein the convolutional neural network further comprises groups of residual blocks.

13. The artificial intelligence-based system of clause 12, wherein each group of residual blocks is parameterized by a number of convolution filters in the residual blocks, a convolution window size of the residual blocks, and an atrous convolution rate of the residual blocks.

14. The artificial intelligence-based system of clause 12, wherein the convolutional neural network is parameterized by a number of residual blocks, a number of skip connections, and a number of residual connections.

15. The artificial intelligence-based system of clause 12, wherein each group of residual blocks produces an intermediate output by processing a preceding input, wherein dimensionality of the intermediate output is $(I-[\{(W-1)*D\}*A])\times N$, where
I is dimensionality of the preceding input,
W is convolution window size of the residual blocks,
D is atrous convolution rate of the residual blocks,
A is a number of atrous convolution modules in the group, and
N is a number of convolution filters in the residual blocks.

16. The artificial intelligence-based system of clause 15, wherein the atrous convolution rate progresses non-exponentially from a lower residual block group to a higher residual block group.

17. The artificial intelligence-based system of clause 16, wherein atrous convolutions conserve partial convolution calculations for reuse as adjacent bases are processed.

18. The artificial intelligence-based system of clause 13, wherein the size of convolution window varies between groups of residual blocks.

19. The artificial intelligence-based system of clause 1, wherein dimensionality of the input base sequence is $(Cu+L+Cd)\times4$, where

US 12,646,589 B2

25

Cu is a number of upstream context bases in the left base sequence;

Cd is a number of downstream context bases in the right base sequence, and

L is a number of target base in the target base sequence.

20. The artificial intelligence-based system of clause 11, wherein the convolutional neural network further comprises dimensionality altering convolution modules that reshape spatial and feature dimensions of a preceding input.

21. The artificial intelligence-based system of clause 12, wherein each residual block further comprises at least one batch normalization module, at least ReLU module, at least one atrous convolution module, and at least one residual connection.

22. The artificial intelligence-based system of clause 21, wherein each residual block further comprises two batch normalization modules, two ReLU non-linearity modules, two atrous convolution modules, and one residual connection.

23. The artificial intelligence-based system of clause 1, wherein the sequence-to-sequence model is trained on training data that includes both coding and non-coding bases.

24. An artificial intelligence-based system, comprising:

a sequence-to-sequence model;

a plurality of per-track processors corresponding to a respective epigenetic track in a plurality of epigenetic tracks, wherein each per-track processor further comprises at least one processing module (e.g., a residual block) and an output module (e.g., a linear module, a rectified linear unit (ReLU) module);

the sequence-to-sequence model processes an input base sequence and generates an alternative representation of the input base sequence;

each per-track processor's processing module processes the alternative representation and generates a further alternative representation that is specific to a particular per-track processor; and each per-track processor's output module processes the further alternative representation generated by its corresponding processing module and produces, as output, a signal level for a corresponding epigenetic track and for each base in the input base sequence.

Other implementations may include a non-transitory computer readable storage medium storing instructions executable by a processor to perform actions of the system described above. Yet another implementation may include a method performing actions of the system described above.

Artificial Intelligence-Based Pathogenicity Classification of Noncoding Variants 1. An artificial intelligence-based system, comprising:

an input preparation module that accesses a sequence database and generates (i) a reference sequence that contains, at a target position, a base, wherein the base is flanked by downstream and upstream context bases, and (ii) an alternative base sequence that contains, at the target position, a variant of the base, wherein the variant is flanked by the downstream and upstream context bases;

a sequence-to-sequence model that processes the reference sequence and generates a reference output, wherein the reference output specifies, for each base in the reference sequence, signal levels of a plurality of epigenetic tracks, and processes the alternative sequence and generates an alternative output, wherein the alternative output specifies, for each base in the alternative sequence, the signal levels of the plurality of epigenetic tracks;

a comparator that applies a position-wise deterministic comparison function to the reference output and the alternative output generated for bases in the reference sequence and the alternative sequence, and generates a position-wise comparison result based on differences, caused by the variant in the alternative sequence, between the signal levels of the reference output and the signal levels of the alternative output; and a pathogenicity determiner that processes the position-wise comparison result and produces an output which scores the variant in the alternative sequence as pathogenic or benign.

2. The artificial intelligence-based system of clause 1, wherein the position-wise deterministic comparison function calculates an element-wise difference between the reference output and the alternative output.

3. The artificial intelligence-based system of clause 1, wherein the position-wise deterministic comparison function calculates an element-wise sum of the reference output and the alternative output.

4. The artificial intelligence-based system of clause 1, wherein the position-wise deterministic comparison function calculates an element-wise ratio between the reference output and the alternative output.

5. The artificial intelligence-based system of clause 1, further comprises a post-processing module that processes the reference output and produces a further reference output; and processes the alternative output and produces a further alternative output.

6. The artificial intelligence-based system of clause 5, wherein the comparator applies the position-wise deterministic comparison function to the further reference output and the further alternative output for elements in the reference output and the alternative output, and generates the position-wise comparison result.

7. The artificial intelligence-based system of clause 5, wherein the post-processing module is a convolutional neural network with one or more convolution layers.

8. The artificial intelligence-based system of clause 1, wherein the sequence-to-sequence model further comprises a plurality of intermediate layers, and one of the intermediate layers processes the reference sequence and generates an intermediate reference output;

processes the alternative sequence and generates an intermediate alternative output; and the comparator applies the position-wise deterministic comparison function to the intermediate reference output and the intermediate alternative output for elements in the intermediate reference sequence and the intermediate alternative sequence, and generates the position-wise comparison result.

9. The artificial intelligence-based system of clause 1, wherein the reference sequence is further flanked by right and left flanking base sequences, and the sequence-to-sequence model processes the reference sequence along with the right and left flanking base sequences.

10. The artificial intelligence-based system of clause 1, wherein the alternative sequence is further flanked by right and left flanking base sequences, and the sequence-tosequence model processes the alternative sequence along with the right and left flanking base sequences.

11. The artificial intelligence-based system of clause 1, wherein the reference sequence and the alternative sequence are non-coding base sequences.

12. The artificial intelligence-based system of clause 11, wherein the reference sequence and the alternative sequence are promoter sequences, and the variant is a promoter sequence.

13. The artificial intelligence-based system of clause 1, wherein the input feeding module further includes in the input to the pathogenicity determiner, in addition to the position-wise comparison result, the reference sequence and the alternative sequence.

14. The artificial intelligence-based system of clause 13, wherein the reference sequence and the alternative sequence are one-hot encoded.

15. The artificial intelligence-based system of clause 1, wherein the sequence-to-sequence model is a convolutional neural network.

16. The artificial intelligence-based system of clause 15, wherein the convolutional neural network further comprises groups of residual blocks.

17. The artificial intelligence-based system of clause 16, wherein each group of residual blocks is parameterized by a number of convolution filters in the residual blocks, a convolution window size of the residual blocks, and an atrous convolution rate of the residual blocks.

18. The artificial intelligence-based system of clause 16, wherein the convolutional neural network is parameterized by a number of residual blocks, a number of skip connections, and a number of residual connections.

19. The artificial intelligence-based system of clause 1, wherein the pathogenicity determiner further comprises an output module that produces the output as a pathogenicity score.

20. The artificial intelligence-based system of clause 19, wherein the output module is a sigmoid processor and the pathogenicity score is between zero and one.

21. The artificial intelligence-based system of clause 20, further comprising identifying whether the variant in the alternative sequence is pathogenic or benign based on whether the pathogenicity score is above or below a preset threshold.

22. The artificial intelligence-based system of clause 1, further comprising jointly training the sequence-to-sequence model and the pathogenicity determiner using contiguous backpropagation.

23. The artificial intelligence-based system of clause 1, further comprising using transfer learning to initialize weights of the pathogenicity determiner during its training based on weights of the sequence-to-sequence model learned during its training.

24. An artificial intelligence-based system, comprising:
   a pathogenicity determiner that processes a position-wise comparison result and generates an alternative representation of the position-wise comparison result,
      wherein the position-wise comparison result is based on differences, caused by a variant in an alternative sequence, between
         signal levels of a plurality of epigenetic tracks determined for bases in a reference sequence, and
         signal levels of the plurality of epigenetic tracks determined for bases in the alternative sequence; and
   an output module that processes the alternative representation of the position-wise comparison result and produces an output which scores the variant in the alternative sequence as pathogenic or benign.

25. The artificial intelligence-based system of clause 24, further comprising providing the reference sequence as input to the pathogenicity determiner.

26. The artificial intelligence-based system of clause 24, further comprising providing the alternative sequence as input to the pathogenicity determiner.

Other implementations may include a non-transitory computer readable storage medium storing instructions executable by a processor to perform actions of the system described above. Yet another implementation may include a method performing actions of the system described above.

Gene Expression-Based Labeling of Non-Coding Variants for Artificial Intelligence-Based Training 1. An artificial intelligence-based method of training a pathogenicity determiner, including:
   training the pathogenicity determiner using training data that includes a pathogenic set of non-coding variants that are annotated with a pathogenic label (e.g., "1") and a benign set of non-coding variants that are annotated with a benign label (e.g., "0");
   wherein the pathogenic set of non-coding variants are singletons that appear only in a single individual among a cohort of individuals, and, for genes adjacent to the non-coding variants in the pathogenic set, the single individual exhibited under-expression across a plurality of tissues;
   wherein the benign set of non-coding variants are singletons that appear only in a single individual among the cohort of individuals and, for genes adjacent to the non-coding variants in the benign set, the single individual did not exhibit the under-expression across the plurality of tissues; and
   for a particular non-coding variant in the training data,
      generating (i) an alternative sequence that contains, at a target position, the particular non-coding variant flanked by downstream and upstream context bases, and (ii) a reference sequence that contains, at the target position, a reference base flanked by the downstream and upstream context bases;
      processing the alternative and reference sequences through an epigenetic model and determining, for each base in the alternative and reference sequences, signal levels of a plurality of epigenetic tracks;
      generating a position-wise comparison result based on differences, caused by the particular non-coding variant, between the signal levels determined for bases in the reference sequence and the alternative sequence;
      processing the position-wise comparison result through the pathogenicity determiner and producing a pathogenicity prediction for the particular non-coding variant; and
      modifying weights of the pathogenicity determiner using backpropagation based on an error computed between the pathogenicity prediction and the pathogenic label when the particular non-coding variant is from the pathogenic set, and between the pathogenicity prediction and the benign label when the particular non-coding variant is from the benign set.

2. The artificial intelligence-based method of clause 1, wherein the under-expression is determined by analyzing distributions of expressions exhibited by the cohort of individuals for each of the genes across each of the plurality of tissues, and calculating a median z-score for the single individual based on the distributions.

3. The artificial intelligence-based method of clause 1, wherein adjacency of the genes adjacent to the non-coding variants in the pathogenic set is measured based on a number of bases between transcription start sites (TSSs) on the genes and the non-coding variants.

4. The artificial intelligence-based system of clause 3, wherein the number of bases is 1500 bases.

5. The artificial intelligence-based system of clause 1, further comprising, when the median z-score is below a threshold, inferring the under-expression.

6. The artificial intelligence-based system of clause 5, wherein the threshold is −1.5.

Other implementations may include a non-transitory computer readable storage medium storing instructions executable by a processor to perform actions of the system described above. Yet another implementation may include a method performing actions of the system described above.

The invention claimed is:

1. An artificial intelligence-based system, comprising:
one or more processors configures to execute processor-executable code; and
one or more memory structures configured to store processor-executable code, wherein the processor executable code, when executed, causes implementation of:
an input preparation module that accesses a sequence database and generates an input base sequence, wherein the input base sequence comprises
(i) a target base sequence with target bases, wherein the target base sequence is flanked by
(ii) a right base sequence with downstream context bases, and
(iii) a left base sequence with upstream context bases;
a sequence-to-sequence model that processes the input base sequence and generates an alternative representation of the input base sequence; and
an output module that processes the alternative representation of the input base sequence and produces at least one per-base output for each of the target bases in the target base sequence,
wherein the per-base output specifies, for a corresponding target base, signal levels of a plurality of epigenetic tracks.

2. The artificial intelligence-based system of claim 1, wherein the per-base output uses continuous values to specify the signal levels of the plurality of epigenetic tracks.

3. The artificial intelligence-based system of claim 1, wherein the output module further comprises a plurality of per-track processors, with each per-track processor corresponds to a respective epigenetic track in the plurality of epigenetic tracks and produces a signal level for a corresponding epigenetic track.

4. The artificial intelligence-based system of claim 3, wherein each per-track processor in the plurality of per-track processors processes the alternative representation of the input base sequence, generates a further alternative representation that is specific to a particular per-track processor, and produces the signal level for the corresponding epigenetic track based on the further alternative representation.

5. The artificial intelligence-based system of claim 4, wherein each per-track processor further comprises at least one residual block and a linear module and/or rectified linear unit (ReLU) module, and
wherein the residual block generates the further alternative representation and the linear module and/or the ReLU module processes the further alternative representation and produces the signal level for the corresponding epigenetic track.

6. The artificial intelligence-based system of claim 3, wherein each per-track processor in the plurality of per-track processors processes the alternative representation of the input base sequence and produces the signal level for the corresponding epigenetic track based on the alternative representation.

7. The artificial intelligence-based system of claim 6, wherein each per-track processor further comprises a linear module and/or a ReLU module.

8. The artificial intelligence-based system of claim 1, wherein the plurality of epigenetic tracks includes deoxyribonucleic acid (DNA) methylation changes (e.g., CpG), histone modifications, noncoding ribonucleic acid (ncRNA) expression, and chromatin structural changes (e.g., nucleosome positioning).

9. The artificial intelligence-based system of claim 1, wherein the plurality of epigenetic tracks includes deoxyribonuclease (DNase) tracks.

10. The artificial intelligence-based system of claim 1, wherein the plurality of epigenetic tracks includes histone 3 lysine 27 acetylation (H3K27ac) tracks.

11. The artificial intelligence-based system of claim 1, wherein the sequence-to-sequence model is a convolutional neural network.

12. The artificial intelligence-based system of claim 11, wherein the convolutional neural network further comprises groups of residual blocks.

13. The artificial intelligence-based system of claim 12, wherein each group of residual blocks is parameterized by a number of convolution filters in the residual blocks, a convolution window size of the residual blocks, and an atrous convolution rate of the residual blocks.

14. The artificial intelligence-based system of claim 13, wherein the size of convolution window varies between groups of residual blocks.

15. The artificial intelligence-based system of claim 12, wherein the convolutional neural network is parameterized by a number of residual blocks, a number of skip connections, and a number of residual connections.

16. The artificial intelligence-based system of claim 12, wherein each group of residual blocks produces an intermediate output by processing a preceding input, wherein dimensionality of the intermediate output is $(I-[\{(W-1)*D\}*A])\times N$, where
I is dimensionality of the preceding input,
W is convolution window size of the residual blocks,
D is atrous convolution rate of the residual blocks,
A is a number of atrous convolution modules in the group, and
N is a number of convolution filters in the residual blocks.

17. The artificial intelligence-based system of claim 16, wherein the atrous convolution rate progresses non-exponentially from a lower residual block group to a higher residual block group.

18. The artificial intelligence-based system of claim 17, wherein atrous convolutions conserve partial convolution calculations for reuse as adjacent bases are processed.

19. The artificial intelligence-based system of claim 12, wherein each residual block further comprises at least one batch normalization module, at least ReLU module, at least one atrous convolution module, and at least one residual connection.

20. The artificial intelligence-based system of claim 19, wherein each residual block further comprises two batch normalization modules, two ReLU non-linearity modules, two atrous convolution modules, and one residual connection.

21. The artificial intelligence-based system of claim 11, wherein the convolutional neural network further comprises dimensionality altering convolution modules that reshape spatial and feature dimensions of a preceding input.

22. The artificial intelligence-based system of claim 1, wherein dimensionality of the input base sequence is (Cu+1+Cd)×4, where Cu is a number of upstream context bases in the left base sequence, Cd is a number of downstream context bases in the right base sequence, and L is a number of target base in the target base sequence.

23. The artificial intelligence-based system of claim 1, wherein the sequence-to-sequence model is trained on training data that includes both coding and non-coding bases.

24. An artificial intelligence-based system, comprising:

one or more processors configures to execute processor-executable code; and one or more memory structures configured to store processor-executable code, wherein the processor executable code, when executed, causes implementation of:

a sequence-to-sequence model;

a plurality of per-track processors corresponding to a respective epigenetic track in a plurality of epigenetic tracks, wherein each per-track processor further comprises at least one processing module (e.g., a residual block) and an output module (e.g., a linear module, a rectified linear unit (ReLU) module);

wherein the sequence-to-sequence model processes an input base sequence and generates an alternative representation of the input base sequence;

wherein each per-track processor's processing module processes the alternative representation and generates a further alternative representation that is specific to a particular per-track processor; and wherein each per-track processor's output module processes the further alternative representation generated by its corresponding processing module and produces, as output, a signal level for a corresponding epigenetic track and for each base in the input base sequence.

* * * * *